US012806254B2

(12) United States Patent
Kim et al.

(10) Patent No.: US 12,806,254 B2
(45) Date of Patent: Nov. 24, 2026

(54) VACCINE FOR TREATING MULTIPLE SCLEROSIS

(71) Applicant: RESEARCH & BUSINESS FOUNDATION SUNGKYUNKWAN UNIVERSITY, Gyeonggi-do (KR)

(72) Inventors: Jaeyun Kim, Gyeonggi-do (KR); Thanh Loc Nguyen, Gyeonggi-do (KR)

(73) Assignee: RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 683 days.

(21) Appl. No.: 18/157,484

(22) Filed: Jan. 20, 2023

(65) Prior Publication Data

US 2023/0241190 A1 Aug. 3, 2023

(30) Foreign Application Priority Data

Jan. 21, 2022 (KR) ........................ 10-2022-0009549

(51) Int. Cl.
*A61K 39/00* (2006.01)
*A61K 9/16* (2006.01)
*A61P 25/28* (2006.01)

(52) U.S. Cl.
CPC ........ *A61K 39/0007* (2013.01); *A61K 9/1611* (2013.01); *A61P 25/28* (2018.01)

(58) Field of Classification Search
CPC .... A61K 39/0007; A61K 9/1611; A61P 25/28
See application file for complete search history.

(56) References Cited

U.S. PATENT DOCUMENTS

2020/0246441 A1* 8/2020 Koyakutty .............. A61P 37/00

FOREIGN PATENT DOCUMENTS

| | | | | | |
|---|---|---|---|---|---|
| AU | 2020201037 | B1 | * | 2/2021 | ......... A61K 49/1824 |
| CN | 109607554 | A | * | 4/2019 | ............. C01B 33/18 |
| KR | 1020150028293 | | | 3/2015 | |
| KR | 1020160137109 | | | 11/2016 | |
| KR | 101724142 | B | * | 4/2018 | ........... A61K 9/2086 |

OTHER PUBLICATIONS

KIPO, Notice of Allowance of KR 10-2022-0009549 dated May 13, 2025, total 3 pages.

Delaram Poormoghadam et al., "The particle size of drug nanocarriers dictates the fate of neurons; critical points in neurological therapeutics", Nanotechnology, vol. 31, No. 33, pp. 1-12, May 28, 2020.

Mehrdad Gholamzad et al., "Prophylactic and Therapeutic Effects of MOG-Conjugated PLGA Nanoparticles in C57Bl/6 Mouse Model of Multiple Sclerosis", Advanced pharmaceutical bulletin, vol. 11, No. 3, pp. 505-513, Jul. 26, 2020.

(Continued)

*Primary Examiner* — Jianfeng Song
(74) *Attorney, Agent, or Firm* — LEX IP MEISTER, PLLC

(57) ABSTRACT

The present disclosure relates to a vaccine composition for treating multiple sclerosis. The vaccine composition of the present disclosure induces immune tolerance and suppresses autoimmune response itself, thus can be usefully applied to the treatment of multiple sclerosis.

7 Claims, 61 Drawing Sheets

(56) References Cited

OTHER PUBLICATIONS

Karin L. Heckman et al., "Custom Cerium Oxide Nanoparticles Protect Against a Free Radical Mediated Autoimmune Degenerative Disease in the Brain", ACS nano, vol. 7, No. 12, pp. 10582-10596, Nov. 22, 2013.

Kwon, D. et al. Extra-large pore mesoporous silica nanoparticles for directing in vivo M2 macrophage polarization by delivering IL-4. Nano Lett. 17,2747-2756 (2017).

Nguyen, T. L., Cha, B. G., Choi, Y., Im, J. & Kim, J. Injectable dual-scale mesoporous silica cancer vaccine enabling efficient delivery of antigen/adjuvant-loaded nanoparticles to dendritic cells recruited in local macroporous scaffold. Biomaterials 239, 119859 (2020).

Croissant, J.G., Fatieiev, Y. & Khashab, N.M. Degradability and clearance of silicon, organosilica, silsesquioxane, silica mixed oxide, and mesoporous silica nanoparticles. Adv. Mater. 29, 1604634 (2017).

Bindini, E. et al. Following in situ the degradation of mesoporous silica in biorelevant conditions: at last, a good comprehension of the structure influence. ACS Appl. Mater. Interfaces 12, 13598-13612 (2020).

Jeong, H. G. et al. Ceria Nanoparticles Fabricated with 6-Aminohexanoic Acid that Overcome Systemic Inflammatory Response Syndrome. Adv. Healthc. Mater. 8, 1-10 (2019).

Sadanandan, Prashant, et al. "Exploiting the preferential phagocytic uptake of nanoparticle-antigen conjugates for the effective treatment of autoimmunity." Nanomedicine: Nanotechnology, Biology and Medicine 40 (2022): 102481., (13 pages).

Korean Office Action issued on Aug. 28, 2024, in counterpart Korean Patent Application No. 10-2022-0009549 (4 pages in English, 5 pages in Korean).

* cited by examiner

FIG. 9

| | MSN | MSN-MOG (1xMSN-MOG) | MSN-OVA | MOG |
|---|---|---|---|---|
| Loading efficiency (%) | N/A | 22.76 ± 0.42 | 17.50 ± 3.09 | N/A |
| Loading peptide (μg) per mg MSNs | N/A | 113.80 ± 2.08 | 87.49 ± 15.44 | N/A |
| Amount of peptide per injection (μg) | N/A | 10 ± 0.18 | 10 ± 1.76 | 10 |
| Amount of MSN per injection (μg) | 87.87 | 87.87 | 114.30 | N/A |

VACCINE FOR TREATING MULTIPLE SCLEROSIS

CROSS-REFERENCE TO RELATED APPLICATION(S)

This application is based on and claims priority under 35 U.S.C. 119 to Korean Patent Application No. 10-2022-0009549, filed on Jan. 21, 2022, in the Korean Intellectual Property Office, the disclosure of which is herein incorporated by reference in its entirety.

FIELD

The present disclosure has been made with the support of the Ministry of Science and ICT of the Republic of Korea, under Project Number 2019R1A2C2004765, wherein the research management institution for the above project is the National Research Foundation of Korea, the research project name is “Individual Basic Research (the Ministry of Science and ICT of the Republic of Korea)(R& D)”, the research task name is “Development of an immunosuppressive autoimmune disease vaccine based on redox catalytic inorganic nanoparticles”, the responsible institution is Sungkyunkwan University, and the research period is 2020.03.01-2021.02.28.

In addition, the present disclosure has been made with the support of the Ministry of Science and ICT of the Republic of Korea, under Project Number 2020M3A9D3039720, wherein the research management institution for the above project is the National Research Foundation of Korea, the research project name is “Development of Bio. Medical Technology (R& D)”, the research task name is “Development of allergic disease treatment technology based on regulatory T cell induction mechanism through control of reactive oxygen species in dendritic cells”, the responsible institution is Sungkyunkwan University (Natural Sciences Campus), and the research period is 2021.03.01-2021.12.31.

Furthermore, the present disclosure has been made with the support of the Korea Forest Service of the Republic of Korea, under Project Number 2020209B10-2122-BA01, wherein the research management institution for the above project is the National Research Foundation of Korea, the research project name is “Research on discovery of forest bioresource materials (R&D)”, the research task name is “Development of antioxidant lignin nanoparticle-based vaccine for multiple sclerosis treatment”, the responsible institution is Research & Business Foundation SUNGKYUNKWAN UNIVERSITY, and the research period is 2021.01.01-2021.12.31.

This application claims the benefit of Korean Patent Application No. 10-2022-0009549 filed on Jan. 21, 2022, with the Korean Intellectual Property Office, the entire contents of which are incorporated herein by reference.

BACKGROUND

Multiple sclerosis (MS) is a chronic inflammatory disease that occurs in the central nervous system, such as the brain, spinal cord, and optical nerve, and 80% or more of multiple sclerosis cases are clinically relapsing-remitting multiple sclerosis with repeated relapses and remittances. Approximately 2.3 million people (as of 2018) are estimated as being multiple sclerosis patients all over the world. The incidence of multiple sclerosis is rapidly increasing among young adults of 20 to 40 years old, and a large-scale market is formed for multiple sclerosis among central nervous system diseases since multiple sclerosis patients have a similar average life expectancy to normal person and thus should take medicines in their entire lives. The initial symptoms at onset begin sensory impairment symptoms or sudden weaken eyesight caused by optic neuritis, followed by motor disabilities, such as hemiplegia, paraplegia, and quadriplegia, as well as dysarthria and cognitive dysfunction.

Central nervous system diseases are anticipated to increase due to the accelerated aging over the world, and neurological diseases correspond to a group of diseases, for which socioeconomic costs are likely to increase to the highest levels in the future.

In the neurons of the central nervous system, axons are surrounded by an insulating material called myelin sheaths. Multiple sclerosis is a neurodegenerative disease in which myelin is stripped away from axons, resulting in dysfunctions in neuronal signal transduction of neurons.

The cause of multiple sclerosis is an autoimmune disease, in which “$CD4^+$ helper T cells”, self-reactive immune cells, penetrate the blood-brain barrier and infiltrate the central nervous system to stimulate nearby macrophages, thereby releasing inflammatory cytokines that destroy myelin, resulting in myelin damage and demyelination.

The current treatment for multiple sclerosis involves a combination of medication therapy (symptomatic relief medicines and disease-modifying medicines) and rehabilitation therapy (exercise therapy for muscle enhancement and stiffness relief). The symptomatic relief medicines include steroid prescriptions for treating acute inflammation, muscle relaxants, and antidepressants. The disease-modifying medicines mainly employ drugs that lower autoimmune responses by regulating the increase in IgG and the blood-brain barrier penetration of T cells.

However, the efficacies and targets of existing medicines are limited, and medicines for severe patients are insufficient and thus there are still various unmet needs. There is no treatment based on the mechanism of immune cells attacking myelin in the central nervous system.

SUMMARY

The present inventors have made intensive research efforts to develop a vaccine composition for treating multiple sclerosis, which suppresses an autoimmune response itself by inducing immune tolerance that inhibits self-reactive immune cells, which are a factor of multiple sclerosis. As a result, the present inventors established that biocompatible porous nanoparticles comprising myelin-derived self-antigen loaded in larger pore size than that of the conventional porous nanoparticles. The composition can be used to treat multiple sclerosis very effectively, and specifically, for example, biocompatible porous nanoparticles comprising three-dimensional radial pores with a mesopore size can be used to treat multiple sclerosis effectively, and thus completed the present disclosure.

Therefore, it is an object of the present disclosure to provide a vaccine composition for treating multiple sclerosis.

It is another object of the present disclosure to provide a method for preparing a vaccine composition for treating multiple sclerosis.

It is another object of the present disclosure to provide a pharmaceutical composition for inducing immune tolerance.

It is yet another object of the present disclosure to provide a method for preventing or treating multiple sclerosis, the method comprising administering to a subject the above-described vaccine composition or pharmaceutical composition for inducing immune tolerance for treating multiple sclerosis.

In accordance with an aspect of the present disclosure, there is provided a vaccine composition for treating multiple sclerosis, the vaccine composition comprising biocompatible porous nanoparticles; and myelin-derived self-antigen loaded in the nanoparticles.

The present inventors have made intensive research efforts to develop a vaccine composition for treating multiple sclerosis, which suppresses an autoimmune response itself by inducing immune tolerance that inhibits self-reactive immune cells, which are a factor of multiple sclerosis. As a result, the present inventors established that biocompatible porous nanoparticles comprising myelin-derived self-antigen loaded thereon and comprising three-dimensional radial pores can be used to treat multiple sclerosis.

In an embodiment of the present disclosure, the biocompatible porous nanoparticles of the present disclosure have mesopores with a diameter of 5 nm to 40 nm. Pores formed in conventionally known drug-loading porous nanoparticles generally have a diameter of about 3 nm or less, whereas the biocompatible porous nanoparticles of the present disclosure comprise pores with a diameter of 5 nm to 40 nm. More specifically, the biocompatible porous nanoparticles of the present disclosure comprise pores with a diameter of 5 nm to 35, and more specifically, a diameter of 10 nm to 30 nm. A smaller pore size than that of the porous nanoparticles of the present disclosure has difficulty in intensive loading of drugs, but the use of porous particles having the same pore size as in the present disclosure enables the intensive loading of drugs, thereby increasing the efficiency of drug delivery.

In an embodiment of the present disclosure, the biocompatible porous nanoparticles of the present disclosure comprise three-dimensional radial pores. The three-dimensional radial pores, which is in contrast to conventional typical two-dimensional pores of typical porous nanoparticles, enable more intensive loading of a predetermined drug. The three-dimensional radial pores of the present disclosure are formed as nanoparticles grow radially from the center thereof, and this can be understood with reference to FIG. 2A.

In an embodiment of the present disclosure, the biocompatible porous nanoparticles of the present disclosure are inorganic nanoparticles. The inorganic nanoparticles of the present disclosure are composed of silica, a metal oxide, or the like and have a nano size of several tens of nanometers to several hundreds of nanometers.

The inorganic nanoparticles of the present disclosure are characterized by having properties of loading an antigen in a porous structure thereof, and any material can be selected without particular limitation as long as the material is a biocompatible material and has a negative influence on the exhibition of efficacy of the vaccine of the present disclosure.

In an embodiment of the present disclosure, the inorganic nanoparticles of the present disclosure may be at least one selected from the group consisting of silica nanoparticles, iron oxide nanoparticles, cerium oxide nanoparticles, manganese oxide nanoparticles, platinum nanoparticles, selenium nanoparticles, and carbon nanoparticles.

In an embodiment of the present disclosure, the biocompatible porous nanoparticles may be organic nanoparticles.

In a specific embodiment of the present disclosure, the organic nanoparticles may be at least one selected from the group consisting of poly(D,L-lactic-co-glycolic acid), polylactic acid, polyglycolic acid, poly(caprolactone), poly(valerolactone), poly(hydroxybutyrate) and poly(hydroxyvalerate), heparin, alginate, hyaluronic acid, chitosan, chondroitin sulfate, dermatan 5-sulfate, keratan sulfate, dextran, dextran sulfate, polyethylene glycol, polyethylene oxide, polyvinyl alcohol, polyethylene oxide-polypropylene oxide block copolymer, alkyl cellulose, and hydroxyalkyl cellulose, but is not limited thereto.

In an embodiment of the present disclosure, the vaccine composition of the present disclosure induces immune tolerance to treat multiple sclerosis. The term immune tolerance refers to the non-responsiveness of the immune system to a specific antigen, which means that T cells or B cells do not provoke an immune response to a specific antigen.

In an embodiment of the present disclosure, the vaccine composition of the present disclosure can increase regulatory T cells. As used herein, the term "regulatory T cells" refers to a type of T cells that regulates an inflammatory response of abnormally activated immune cells, and regulatory T cells is also denoted by Tregs. The regulatory T cells may be roughly classified into natural Treg and adaptive Treg. $CD4^+$ $CD25^+$ T cells, which is natural Treg, are endowed with immunosuppressive functions since when newly produced from the thymus gland and constitutes 5 to 10% of peripheral $CD4^+$ T lymphocyte in a normal individual. Although the immunosuppressive mechanism of natural Treg has not been accurately revealed so far, a factor of controlling the expression of a gene called Foxp3 has been recently found to play a critical role in the differentiation and activation of the natural Treg. Moreover, peripheral natural T cells can be differentiated into cells which exert an immunosuppressive effect when stimulated by self-antigen or foreign antigen under a specific environment. These cells are called adaptive Treg or inducible Treg. Tr1 secreting IL-10, Th3 secreting TGF-β, CD8 Ts, and the like correspond to adaptive Treg.

In an embodiment of the present disclosure, the myelin-derived self-antigen of the present disclosure may include myelin oligodendrocyte glycoprotein peptide or a fragment thereof, myelin proteolipid protein peptide or a fragment thereof, myelin basic protein peptide or a fragment thereof, and αβ-crystalline peptide (CRYAB) or a fragment thereof.

In an embodiment of the present disclosure, the fragment of the at least one peptide selected from the group consisting of myelin oligodendrocyte glycoprotein peptide, myelin proteolipid protein peptide, myelin basic protein peptide, and αβ-crystalline peptide (CRYAB), may be 5 to 25 amino acids in length. More specifically, the fragment of the peptide maybe 6 to 24 amino acids in length, 7 to 23 amino acids in length, or 8 to 22 amino acids in length, but is not limited thereto.

In an embodiment of the present disclosure, the fragment of the myelin oligodendrocyte glycoprotein peptide may be a myelin oligodendrocyte glycoprotein (MOG) fragment with 5 to 30 amino acids in length or an MOG fragment with 10 to 25 amino acids in length. More specifically, the fragment of the myelin oligodendrocyte glycoprotein peptide may be $MOG_{1-20}$, $MOG_{35-55}$, $MOG_{38-50}$, or $MOG_{40-55}$, but is not limited thereto.

In an embodiment of the present disclosure, the fragment of the myelin proteolipid protein peptide may be a PLP fragment with 5 to 30 amino acids in length or a PLP fragment with 10 to 25 amino acids in length. More specifically, the fragment of the myelin proteolipid protein peptide may be $PLP_{139-151}$, $PLP_{139-155}$, or $PLP_{180-199}$, but is not limited thereto.

In an embodiment of the present disclosure, the fragment of the myelin basic protein peptide may be an MBP fragment with 5 to 30 amino acids in length or an MBP fragment with 10 to 25 amino acids in length. More specifically, the fragment of the myelin basic protein peptide may be $MBP_{1-9}$, $MBP_{13-32}$, $MBP_{30-44}$, $MBP_{82-92}$, $MBP_{83-99}$, $MBP_{85-99}$, $MBP_{84-102}$, $MBP_{131-145}$, $MBP_{139-154}$, $MBP_{140-154}$, or $MBP_{146-170}$, but is not limited thereto.

In an embodiment of the present disclosure, the fragment of the αB-crystalline peptide (CRYAB) may be a CRYAB fragment with 5 to 30 amino acids in length or a CRYAB fragment with 10 to 25 amino acids in length.

In an embodiment of the present disclosure, the myelin-derived self-antigen of the present disclosure may be myelin oligodendrocyte glycoprotein (MOG) peptide 35-55 ($MOG_{35-55}$). $MOG_{35-55}$ of the present disclosure is a glycoprotein peptide molecule having the peptide sequence as set forth in SEQ ID NO: 1 (MEVGWYRSPFSRWHLYRNGK).

As used herein, the terms "polypeptide", "peptide", and "protein" are defined to mean biomolecules composed of amino acids linked by peptide bonds.

More specifically, the term "peptide" is a chain of amino acids (typically L-amino acids), of which alpha carbons are linked through a peptide bond formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminal" (N-terminal) indicates the free alpha-amino group on the amino acid at the amino terminal of the peptide, or the alpha-amino group (amino group when participating in a peptide bond) of an amino acid at any other location within the peptide. Similarly, the term "carboxy terminal" (C-terminal) indicates the free carboxyl group on the amino acid at the carboxy terminal of a peptide, or the carboxyl group of an amino acid at any other location within the peptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics).

The above-described peptides of the present disclosure may include individual substitutions which alter, add or delete a single amino acid or a small percentage of amino acids (typically less than 5%, more typically less than 1%) in an encoded sequence, and conservatively modified variations where the alterations result in the substitution of a single or multiple amino acids with chemically similar amino acids. Conservative substitution tables providing functionally similar amino acids are well known in the art. The following six groups each show amino acids that are conservative substitutions for one another:

(1) Alanine (A), Serine (S), Threonine (T);
(2) Aspartic acid (D), Glutamic acid (E);
(3) Asparagine (N), Glutamine (Q);
(4) Arginine (R), Lysine (K);
(5) Isoleucine (I), Leucine (L), Methionine (M), Valine (V); and
(6) Phenylalanine (F), Tyrosine (Y), Tryptophan (W).

When the immunogenic peptides are relatively short in length (i.e., less than about 50 amino acids), the peptides are often synthesized using standard chemical peptide synthesis. The myelin oligodendrocyte glycoprotein (MOG) peptide 35-55 of the present disclosure corresponds to a relatively short immunogenic peptide and thus may be synthesized using standard chemical peptide synthesis, but is not limited thereto.

The immunogenic peptides described herein may be synthesized using recombinant nucleic acid methodology. Generally, this involves creating a nucleic acid sequence that encodes a peptide, placing the nucleic acid in an expression cassette under the control of a particular promoter, expressing the peptide in a host, isolating the expressed peptide or polypeptide and, if required, renaturing the peptide. The above-described processes are often well known.

In an embodiment of the present disclosure, the vaccine composition of the present disclosure further comprises ceria nanoparticles bound to the surface of the porous nanoparticles. The ceria nanoparticles mean cerium oxide nanoparticles. When the vaccine composition of the present disclosure is delivered to antigen-presenting cells, the ceria nanoparticles bound to the porous nanoparticles of the vaccine composition of the present disclosure can increase regulatory T cell induction by scavenging intracellular reactive oxygen species to further suppress the activation of the antigen-presenting cells, and thus can enhance the therapeutic effect for multiple sclerosis. In particular, the ceria nanoparticles bound to the surface of the porous nanoparticles of the vaccine composition of the present disclosure can enhance the therapeutic effect for multiple sclerosis in the late treatment for multiple sclerosis. The ceria nanoparticles of the present disclosure are positively charged and the antigen-loaded porous nanoparticles have negative charge characteristics, so that the ceria nanoparticles are bound to the surface of the porous nanoparticles by electrostatic interaction, thereby producing a nanocomposite.

The vaccine composition of the present disclosure may further comprise a solvent, a vehicle, and the like. Examples of the solvent include, but are not limited to, saline and distilled water, and examples of the vehicle include, but are not limited to, aluminum phosphate, aluminum hydroxide, and aluminum potassium sulfate. The vaccine composition of the present disclosure may further comprise substances that are commonly used for vaccine production in the art to which the present disclosure pertains.

The vaccine composition of the present disclosure may be prepared by a method commonly used in the art to which the present disclosure belongs. The vaccine composition of the present disclosure may be prepared as an oral or parenteral formulation, preferably prepared as an injection solution, which is a parenteral formulation, and may be administered by intradermal, intramuscular, intraperitoneal, intravenous, subcutaneous, intranasal, inhaled, or epidural routes.

The vaccine composition of the present disclosure may be administered to a subject in an immunologically effective amount. The term "immunologically effective amount" refers to an amount sufficient to exhibit the effect of preventing or treating multiple sclerosis and an amount that does not cause side effects or serious or excessive immune responses. The exact dose of the vaccine composition of the present disclosure may vary depending on the specific immunogen to be administered, and may be easily determined by those skilled in the art depending on factors well known in the medical field, including the age, body weight, health and sex of a subject to be prevented or treated, the drug sensitivity of the subject, the route of administration, and the mode of administration. The vaccine composition of the present disclosure may be administered once or several times.

The therapeutic vaccine composition of the present disclosure may be administered in combination with other biologically active substances and procedures for the treatment of diseases. The other biologically active substances may be part of the same composition already containing the therapeutic vaccine according to the disclosure, in form of a mixture, wherein the therapeutic vaccine and the other biologically active substance are intermixed in or with the same pharmaceutically acceptable solvent and/or carrier or may be provided separately as part of a separate compositions, which may be offered separately or together in form a kit of parts.

The vaccine composition of the present disclosure may be provided as a pharmaceutical composition and may comprise a pharmaceutically acceptable carrier. The pharmaceutically acceptable carrier contained in the composition of the present disclosure is conventionally used for the formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further comprise a lubricant, a wetting agent, a sweetening agent, a flavoring agent, an emulsifier, a suspending agent, a preservative, and the like, in addition to the above ingredient. Suitable pharmaceutically acceptable carriers and agents are described in detail in Remington's Pharmaceutical Sciences (19th ed., 1995).

The appropriate dose of the pharmaceutical composition of the present disclosure varies depending on factors, such as the formulating method, manner of administration, patient's age, body weight, gender, and severity of disease, time of administration, route of administration, excretion rate, and response sensitivity. Meanwhile, the dose of the pharmaceutical composition of the present disclosure is preferably 0.0001-1000 mg/kg (body weight) per day.

The pharmaceutical composition of the present disclosure may be administered orally, parenterally, or inhalation, and in the case of parenteral administration, it may be administered by intravenous injection, subcutaneous injection, intramuscular injection, intraperitoneal injection, transdermal administration, or the like. Considering that the pharmaceutical composition of the present invention is applied for the treatment of multiple sclerosis, administration is preferably through intravenous injection.

The pharmaceutical composition of the present disclosure is formulated using a pharmaceutically acceptable carrier and/or excipient, according to the method that is easily conducted by person having ordinary skills in the art to which the present disclosure pertains, and the pharmaceutical composition may be prepared into a unit dosage form or may be inserted into a multidose container. Here, the dosage form may be a solution in an oily or aqueous medium, a suspension, an emulsion, an extract, a powder, granules, a tablet, or a capsule, and may further comprise a dispersant or a stabilizer.

The therapeutic vaccine composition of the present disclosure may be administered with the other biologically active substances, simultaneously, intermittently, or sequentially. For example, the therapeutic vaccine composition of the present disclosure may be administered simultaneously with a first additional biologically active substance or sequentially after or before administration of the therapeutic vaccine. If an application scheme is chosen where one or more additional biologically active substances are administered together with the at least one therapeutic vaccine of the present disclosure, the compounds or substances may partially be administered simultaneously, partially sequentially in various combinations.

In accordance with another aspect of the present disclosure, there is provided a method for preparing a vaccine composition for treating multiple sclerosis, the method comprising loading a myelin-derived self-antigen in biocompatible porous nanoparticles.

The loading of the myelin-derived self-antigen in the biocompatible porous nanoparticles according to the preparation method of the present disclosure may be performed by physical adsorption, electrostatic bonding, hydrogen bonding, or covalent bonding, but is not limited thereto.

In an embodiment of the present disclosure, the biocompatible porous nanoparticles of the present disclosure have mesopores with a diameter of 5 nm to 40 nm. Pores formed in conventionally known drug-loading porous nanoparticles generally have a diameter of about 3 nm or less, whereas the biocompatible porous nanoparticles of the present disclosure comprise pores with a diameter of 5 nm to 40 nm. More specifically, the biocompatible porous nanoparticles of the present disclosure comprise pores with a diameter of 5 nm to 35, and more specifically, a diameter of 10 nm to 30 nm.

In an embodiment of the present disclosure, the biocompatible porous nanoparticles of the present disclosure are silica nanoparticles comprising three-dimensional radial pores. The present inventors attain high antigen-loading capacity by using silica nanoparticles comprising three-dimensional radial pores, and thus reduce the delivery amount of the carrier while achieving the sufficient delivery of antigens, thereby deriving an effective immunosuppressive vaccine.

In an embodiment of the present disclosure, the myelin-derived self-antigen of the present disclosure may be at least one peptide selected from the group consisting of myelin oligodendrocyte glycoprotein peptide, myelin proteolipid protein peptide, myelin basic protein peptide, and αB-crystalline peptide (CRYAB), or a fragment thereof.

In an embodiment of the present disclosure, the fragment of the at least one peptide selected from the group consisting of myelin oligodendrocyte glycoprotein peptide, myelin proteolipid protein peptide, myelin basic protein peptide, and αB-crystalline peptide (CRYAB), may be 5 to 25 amino acids in length. More specifically, the fragment of the peptide maybe 6 to 24 amino acids in length, 7 to 23 amino acids in length, or 8 to 22 amino acids in length, but is not limited thereto.

In an embodiment of the present disclosure, the myelin-derived self-antigen of the present disclosure may be myelin oligodendrocyte glycoprotein (MOG) peptide 35-55 ($MOG_{35}$-55).

In an embodiment of the present disclosure, the preparation method of the present disclosure further comprises binding ceria nanoparticles to the myelin-derived self-antigen-loaded biocompatible porous nanoparticles. Due to the antioxidant properties possessed by ceria nanoparticles per se, reactive oxygen species in antigen-presenting cells can be scavenged, leading to an introduction of immune tolerance of antigen-presenting cells, thereby inducing T-cell immunosuppression.

Since the method for preparing a vaccine composition for treating multiple sclerosis according to the present disclosure is a method preparing the vaccine composition for treating multiple sclerosis according to an aspect of the present disclosure, duplicate contents are omitted to avoid excessive complication of the present specification.

In accordance with another aspect of the present disclosure, there is provided a pharmaceutical composition for inducing immune tolerance, the pharmaceutical composition comprising biocompatible porous nanoparticles, a myelin-derived self-antigen loaded in the biocompatible porous nanoparticles, and ceria nanoparticles bound to the surface of the porous nanoparticles.

In an embodiment of the present disclosure, the myelin-derived self-antigen of the present disclosure may be a fragment of at least one peptide selected from the group consisting of myelin oligodendrocyte glycoprotein peptide, myelin proteolipid protein peptide, myelin basic protein peptide, and αB-crystalline peptide (CRYAB), wherein the peptide fragment may be 5 to 25 amino acids in length.

In an embodiment of the present disclosure, the myelin-derived self-antigen of the present disclosure may be myelin oligodendrocyte glycoprotein peptide 35-55 ($MOG_{35-55}$), but is not limited thereto.

In an embodiment of the present disclosure, the biocompatible porous nanoparticles of the present disclosure comprise three-dimensional radial pores.

In an embodiment of the present disclosure, the inducing of the immune tolerance of the present disclosure is an autoimmune suppression in a multiple sclerosis patient. The present disclosure established that the pharmaceutical composition of the present disclosure can suppress the activation of antigen-presenting cells and induce and enhance immune tolerance by intracellular ROS-scavenging activity.

As for the overlapping contents of the pharmaceutical composition for inducing immune tolerance according to an aspect of the present disclosure when compared with the above-described vaccine composition according to another aspect of the present disclosure, the corresponding contents are used in the original form thereof, and the description thereof is omitted to avoid the excessive complexity of the present description.

In accordance with another aspect of the present disclosure, there is provided a method for preventing or treating multiple sclerosis, the method comprising administering to a subject the above-described vaccine composition for treating multiple sclerosis, wherein the vaccine composition comprises biocompatible porous nanoparticles and a myelin-derived self-antigen loaded in the nanoparticles.

As used herein, the term "administration" or "administer" refers to the direct administration of a therapeutically effective amount of the composition of the present disclosure to a subject (i.e., an object) undergoing multiple sclerosis, thereby forming the same amount thereof in the body of the subject.

The term "therapeutically effective amount" of the composition refers to the content of the composition, which is sufficient to provide a therapeutic or preventive effect to a subject to which composition is administered, and thus the term has a meaning encompassing "prophylactically effective amount."

As used herein, the term "subject" is a mammal including a human, a mouse, a rat, a guinea pig, a dog, a cat, a horse, a cow, a pig, a monkey, a chimpanzee, a baboon, or a rhesus monkey. Most specifically, the subject of the present disclosure is a human.

As for the overlapping contents of the method for preventing or treating multiple sclerosis according to an aspect of the present disclosure when compared with the above-described vaccine composition according to another aspect of the present disclosure, the corresponding contents are used in the original form thereof, and the description thereof is omitted to avoid the excessive complexity of the present description.

In accordance with still another aspect of the present disclosure, there is provided a method for preventing or treating multiple sclerosis, the method comprising administering to a subject the above-described pharmaceutical composition for inducing immune tolerance, wherein the pharmaceutical composition comprises biocompatible porous nanoparticles, a myelin-derived self-antigen loaded in the biocompatible porous nanoparticles, and ceria nanoparticles bound to the surface of the porous nanoparticles.

As used herein, the term "administration" or "administer" refers to the direct administration of a therapeutically effective amount of the composition of the present disclosure to a subject (i.e., an object) undergoing multiple sclerosis, thereby forming the same amount thereof in the body of the subject.

The term "therapeutically effective amount" of the composition refers to the content of the composition, which is sufficient to provide a therapeutic or preventive effect to a subject to which composition is administered, and thus the term has a meaning encompassing "prophylactically effective amount."

As used herein, the term "subject" is a mammal including a human, a mouse, a rat, a guinea pig, a dog, a cat, a horse, a cow, a pig, a monkey, a chimpanzee, a baboon, or a rhesus monkey. Most specifically, the subject of the present disclosure is a human.

As for the overlapping contents of the method for preventing or treating multiple sclerosis according to an aspect of the present disclosure when compared with the above-described pharmaceutical composition according to another aspect of the present disclosure, the corresponding contents are used in the original form thereof, and the description thereof is omitted to avoid the excessive complexity of the present description.

Advantageous Effects

The features and advantages of the present disclosure are summarized as follows:

(a) The present disclosure provides a vaccine composition for treating multiple sclerosis.

(b) The present disclosure provides a method for preparing a vaccine composition for treating multiple sclerosis.

(c) The vaccine composition of the present disclosure induces immune tolerance and suppresses autoimmune response itself, thus can be usefully applied to the treatment of multiple sclerosis.

BRIEF DESCRIPTION OF THE DRAWINGS

FIG. 2*a* shows transmission electron microscopy (TEM) image of MSNs, scale bar: 200 nm; the experiment was repeated independently at least three times. FIG. 2*b*. shows representative histograms of rhodamine B isothiocyanate (RITC) signal from splenocytes of C57BL/6 mice that were left untreated (no injection) or intravenously injected with RITC-MSNs 24 h before flow cytometry analysis. FIG. 2*c* shows the percentage of immune cells that engulfed RITC-MSNs in spleens, n=4 biologically independent animals. FIG. 2*d* shows the schematics for MOG loading in MSNs. FIG. 2*e* shows that EAE was induced in C57BL/6 mice before being injected intravenously with bare MSNs (MSN), $MOG_{35-55}$ peptide-loaded MSNs (MSN-MOG), $OVA_{323-339}$ peptide-loaded MSNs (MSN-OVA), soluble MOG (MOG), or left untreated on days 4, 7, and 10 (n=6). FIG. 2*f* shows EAE clinical score for different groups of mice. FIG. 2*g* shows Kaplan-Meier curves demonstrating the percentage of EAE-free mice over time, P values were calculated using log-rank (Mantel-Cox) test. Data in FIG. 2*c* are represented as mean±standard deviation (SD). Data in FIG. 2*f* are represented as mean±standard error (SE). Data in FIG. 2*f* were subjected to one-way analysis of variance (ANOVA) with Dunnett's multiple comparisons test. $P<0.05$ was considered significant.

FIGS. 3*a*, 3*b*, 3*c*, 3*d*, 3*e*, 3*f*, 3*g*, 3*h*, 3*i*, 3*j*, 3*k*, 31, 3*m*, 3*n*, 3*o*, 3*p*, 3*q*, 3*r*, 3*s*, 3*t*, and 3*u* show experimental data indicating that MSN-MOG induced peripheral tolerance in the spleen and MSN-MOG vaccine suppressed CNS-infiltrating APCs and $CD4^+$ cells. FIG. 3*a* shows that EAE-induced mice were intravenously injected with MSN-OVA, MSN-MOG, or left untreated on days 4, 7, and 10 after EAE induction. Splenocytes were isolated and analyzed by flow cytometry on day 20 after EAE induction. FIG. 3*b* and FIG. 3*c* shows CD86 and MHC (major histocompatibility complex)-II expression on $CD11c^+$DCs, $F4/80^+$ macrophages, and $B220^+$ B cells, respectively. FIG. 3*d* shows the frequency of $CD4^+$ T cells. FIG. 3*e* and FIG. 3*f* show percentage of forkhead box $P3^+$ ($Foxp3^+$) among $CD4^+$ T cells and their representative pseudocolor plots, respectively. FIG. 3*g* shows the number of $Foxp3^+$ regulatory T cells (Treg). FIG. 3*h*, FIG. 3*i*, FIG. 3*j* and FIG. 3*k* shows the levels of IL-17A, TNF-α, GM-CSF, and IL-10 secreted by splenocytes stimulated ex vivo with $MOG_{35-55}$, respectively. In FIG. 3*b*-3*e* and FIG. 3*g*-3*k*, n=4 (untreated and MSN-OVA) or 5 (MSN-MOG) biologically independent animals. FIG. 3*l* shows the percentage of $CD11c^+$ DC, $F4/80^+$ macrophages, and $B220^+$ B cells in the spinal cords and FIG. 3*m* shows their representative pseudocolor plots, respectively. FIG. 3*n* shows the number of $CD11c^+$ DCs, $F4/80^+$ macrophages, and $B220^+$ B cells in spinal cords. FIG. 3*o* shows the percentage of APCs expressing MHC-II in spinal cords. FIG. 3*p* shows the number of $CD4^+$ T-cells infiltrating spinal cords. FIG. 3*q* and FIG. 3*r* show the percentage of Iba1 expressed in spinal cord cells and representative pseudocolor plots, respectively. FIG. 3*j* shows EAE mean clinical score of EAE mice that were injected with MSN-MOG, MSN-MOG and control antibody (MSN-MOG+Ctrl Ab), MSN-MOG and anti-CD25 antibody (MSN-MOG+αCD25), or left untreated (n=4). FIG. 3*t* and FIG. 3*u* show the percentage of APCs and $CD4^+$ T cells in the spinal cord on day 20 after disease induction, respectively. Data in FIG. 3*b*-3*e*, 3*g*-31, 3*n*-3*q*, 3*t* and 3*u*, are represented as mean±SD and were subjected to a one-way ANOVA with Dunnett's multiple comparisons tests. $P<0.05$ was considered significant, ns=not significant.

FIG. 4*a* shows the experiment schedule; EAE was induced in mice before administering three MSN-MOG injections starting from day 12 (early therapeutics), day 15 (late therapeutics), or left untreated. FIG. 4*b*, FIG. 4*c*, and FIG. 4*d* show the clinical score, body weight of the mice, and incidence of complete paralysis, respectively, measured over time. n=5 (untreated) or 6 (early therapeutics, late therapeutics) biologically independent animals. FIG. 4*e* is a photograph of an EAE-induced mouse from the late therapeutic group before receiving an injection on day 15 (left) and after 3 MSN-MOG injections on day 22. FIG. 4*f* and FIG. 4*g* shows the EAE clinical score and body weight of mice that received additional MSN-MOG injections on days 28 and 35, respectively; n=5 (untreated) or 6 (early therapeutics, late therapeutics) biologically independent animals. FIG. 4*h* is images of Hematoxylin and eosin (H&E)-stained thoracic vertebrae cross sections of EAE-induced mice on day 50, the experiment was repeated independently at least twice. The discontinuous lines indicate the border between the gray matter (on the lower part) and the ventral white matter of the spinal cord (scale bar: 100 μm). The data in FIG. 4*b*, FIG. 4*c*, FIG. 4*f*, and FIG. 4*g* are represented as mean±SE and were analyzed by one-way ANOVA. Dunnett's multiple comparisons tests were performed in FIG. 4*b*, FIG. 4*c*, and FIG. 4*f*. Tukey's multiple comparisons test was performed in FIG. 4*g*. $P<0.05$ was considered significant, ns=not significant.

FIG. 5*a* shows a scheme demonstrating the catalytic property of CeNPs to scavenge intracellular ROS for the suppression of APCs activation. FIG. 5*b* TEM images of CeNPs (scale bar: 20 nm), the experiment was repeated independently at least three times. FIG. 5*c* Hydrodynamic size distribution of CeNPs and pegylated CeNPs in complete RPMI 1640 medium. FIG. 5*d* Apoptosis of BMDCs after 48 h incubation with various cerium concentrations. BMDCs were incubated with pegylated CeNPs (Ce, 50 μM cerium), $OVA_{323-339}$ (OVA, 1 μg/mL), pegylated CeNPs plus $OVA_{323-339}$ (Ce+OVA), or left untreated for 24 h; following by LPS treatment (1 μg/mL) for the next 24 h; control is the bare BMDCs; n=3 biologically independent samples. FIG. 5*e*, FIG. 5*f* and FIG. 5*g* show expressions of CD86, CD40, and MHC-II on BMDCs, respectively; n=4 biologically independent samples. FIG. 5*h* BMDCs were incubated with pegylated CeNPs (Ce, 50 μM cerium), $OVA_{323-339}$ (OVA, 1 μg/mL), pegylated CeNPs plus $OVA_{323-339}$ (Ce+OVA), or left untreated for 24 h; following by LPS treatment (1 μg/mL) for the next 24 h before being co-cultured with OT-II $CD4^+$ T cells for 72 h. FIG. 5*i*, FIG. 5*j*, FIG. 5*k*, and FIG. 5*l* show the percentage of $CD25^{high}$Foxp3, IL-10, IFN-γ, and IL-17A expression in the gate of $V\alpha2^+$ $CD4^+$ T cells, respectively. FIG. 5*m*, FIG. 5*n*, FIG. 5*o* and FIG. 5*p* show ratios of $CD25^{high}Foxp3^+$ to $IL\text{-}17A^+$ T cells, of $IL\text{-}10^+$ to $IL\text{-}17A^+$ T cells, of $CD25^{high}Foxp3^+$ to $IFN\text{-}\gamma^+$ T cells, and of $IL\text{-}10^+$ to $IFN\text{-}\gamma^+$ T cells, respectively. In FIG. 5*i*-5*p*, n=5 biologically independent samples. The data in FIG. 5*d*-5*g*, FIG. 5*i*-5*p* are represented as mean±SD and were analyzed by one-way ANOVA with Tukey's multiple comparisons test. $P<0.05$ was considered significant, ns=not significant.

FIG. 6*a* shows the TEM image of MSN-MOG-Ce vaccine, scale bar: 50 nm; the experiment was repeated independently at least twice. BMDCs were treated with MSN-MOG, MSN-MOG-Ce, or left untreated for 24 h, followed by stimulation with LPS (100 ng/mL) for the next 12 h. FIG. 6*b* shows intracellular ROS levels in BMDCs, as measured by $H_2$DCFDA assay, n=4 biologically independent samples. FIG. 6*c* shows the percentage of CD11c+ BMDCs expressing CD86, n=4 biologically independent samples. FIG. 6*d* shows EAE clinical scores of mice that were intravenously injected with MSN-MOG, MSN-MOG-Ce, or left untreated on days 15, 18, and 21 after disease induction; n=5 biologically independent animals. FIG. 6*e* and FIG. 6*f* show the expression levels of CD86 and CD40 on APCs in spleens on day 31, respectively. FIG. 6*g* and FIG. 6*h* show the percentage of $Foxp3^+$ cells among $CD3^+$ $CD4^+$ T cells in spleens on day 31 and their representative contour plots, respectively. FIG. 6*i* and FIG. 6*j* show the number and frequency of $CD3^+$ $CD4^+$ T cells infiltrating the spinal cords on day 31. FIG. 6*k* shows the representative pseudocolor plots showing the frequency of $CD3^+$ $CD4^+$ T cells in the spinal cord of the indicated groups. FIG. 6*l* shows the number of MOG-specific $CD4^+$ T cells infiltrating to the spinal cord on day 31. FIG. 6*m* and FIG. 6*n* show the percentage of APCs in the spinal cord and MHC-II expression on these cells on day 31, respectively. FIG. 6*o* shows the frequency of $CD3^+$ $CD4^+$ T cells in cervical lymph nodes on day 31. In FIG. 6*e*-6*g*, 6*i*, 6*k*, 6*m*-6*p*, n=5 biologically independent animals. The data in FIG. 6*b*, 6*c*, 6*e*-6*g*, 6*i*, 6*j*, 6*l*-6*o* are represented as mean±SD and were analyzed by one-way ANOVA. Tukey's multiple comparisons tests were performed in FIG. 6*b* and FIG. 6*c*. Dunnett's multiple comparisons tests were performed in FIG. 6*e*-6*g*, 6*i*, 6*j*, 6*l*-6*o*. The data in FIG. 6*d* are represented as mean±SE and were subjected to a one-way ANOVA with Dunnett's multiple comparisons test. $P<0.05$ was considered significant, ns=not significant.

FIG. 7*a* shows the scanning electron microscope (SEM) image of MSNs, scale bar: 200 nm; the experiment was repeated independently at least three times. FIG. 7*b* shows Nitrogen adsorption/desorption isotherms of MSNs, P/Po indicates the ratio between equilibrium (P) and saturation (Po) pressure of nitrogen at the adsorption temperature. The graph inside shows the distribution of desorption pore-size of MSNs. FIG. 7*c* shows Cell Counting Kit (CCK)-8 viability assay of RAW 264.7 cells incubated for 24 h with various concentrations of MSNs (n=6 biologically independent samples). Data in FIG. 7*c* are represented as mean±standard deviation (SD).

FIG. 9 shows the amounts of loaded MOG peptide and OVA peptide per 1 mg MSNs and the administration doses of each peptide and MSNs used in the present disclosure.

FIG. 10*a* shows that EAE was induced in C57BL/6 mice before intravenous injection with different amounts of MSNs on day 7. The amount of $MOG_{35-55}$ loaded was unchanged. FIG. 10*b* and FIG. 10*c* show EAE clinical scores and body weights, of mice treated with normal (1×MSN-MOG) and double amount of MSNs (2×MSN-MOG), while maintaining the same dose of the MOG peptide. n=4 (untreated) or 5 (1×MSN-MOG and 2×MSN-MOG) biologically independent animals. The data in FIG. 10*b* and FIG. 10*c* are represented as mean±standard error (SE) and were subjected to one-way ANOVA. Dunnett's multiple comparisons tests were performed in FIG. 10*b* and FIG. 10*c*, ns=not significant.

FIG. 11*a* shows that EAE was induced in C57BL/6 mice on days 0 and 1, which was followed by intravenous injection of MSN-OVA, MSN-MOG, or no treatment; n=4 for untreated and MSN-OVA, n=5 for MSN-MOG. Splenocytes were isolated on day 20 after EAE induction for flow cytometry analysis. FIG. 11*b* and FIG. 11*c* show the percentages and numbers of APCs, namely, $CD11c^+$, $F4/80^+$, and $B220^+$ cells, respectively. The data in FIG. 11*b* and FIG. 11*c* have been represented as mean±SD and were subjected to a two-way ANOVA. Dunnett's post-hoc test was performed in FIG. 11*b* and FIG. 11*c*. $P<0.05$ was considered significant, ns=not significant.

FIG. 12*a* shows that EAE was induced in C57BL/6 mice on days 0 and 1, which was followed by intravenous injection of MSN-OVA, MSN-MOG, or no treatment; n=4 for untreated and MSN-OVA, n=5 for MSN-MOG. Cells were isolated from the spinal cord on day 20 after EAE induction for flow cytometry analysis. FIG. 12*b* shows the numbers of MHC-II molecules expressed by APCs, namely, $CD11c^+$, $F4/80^+$, and $B220^+$ cells. The data in FIG. 12*b* have been represented as mean±SD and were subjected to a two-way ANOVA. Dunnett's post-hoc test was performed in FIG. 12*b*. $P<0.05$ was considered significant, ns=not significant.

FIG. 13*a*. shows the experiment schedule; EAE mice were injected with MSN-MOG, MSN-MOG and control antibody (MSN-MOG+Ctrl Ab), MSN-MOG and anti-CD25 antibody (MSN-MOG+αCD25), or left untreated. FIG. 13*b* shows the number of APCs in the spinal cord on day 20, n=4 biologically independent animals. FIG. 13*c* and FIG. 13*d* show representative plots showing the percentage of APCs ($CD11c^+$ cells and $F4/80^+$ cells) and $CD4^+$ T-cells in the spinal cord on day 20, respectively. Data in FIG. 13*b* are represented as mean±SD and were subjected to a one-way ANOVA with Dunnett's multiple comparisons tests. $P<0.05$ was considered significant, ns=not significant.

FIG. 14*a* shows the cell viability of RAW264.7 cells that were incubated with various concentration of cerium for 24 h. FIG. 14*b* shows the TEM image of the cerium oxide nanoparticles. scale bar: 20 nm.

FIG. 15 shows the representative pseudocolor plots of the expression of $CD25^{high}Foxp3^+$, IL-10, IFN-γ, and IL-17A in the gate of OT-II $CD4^+$ T-cells.

FIG. 18*a* shows the experiment schedule; EAE was induced in C57BL/6 mice, followed by thrice intravenous injection of MSN-MOG or MSN-MOG-Ce, or left untreated, starting from day 15 (late therapeutics); n=5 biologically independent animals. FIG. 18*b* shows the body weights of mice during the study; the arrows indicate the injection time points. The data in FIG. 18*b* are represented as mean±SE and were subjected to a one-way ANOVA with Tukey's multiple comparisons test. $P<0.05$ was considered significant, ns=not significant.

FIG. 19*a* shows the experiment schedule; EAE was induced in C57BL/6 mice, followed by thrice intravenous injection of MSN-MOG or MSN-MOG-Ce, or left untreated, on days 15, 18, and 21 prior to flow cytometry analysis of splenocytes on day 31; n=5 biologically independent animals. FIG. 19*b*, FIG. 19*c* and FIG. 19*d* show the frequencies of $CD11c^+$, $F4/80^+$, and $B220^+$ cells, respectively. FIG. 19*e*, FIG. 19*f* and FIG. 19*g* show the numbers of $CD11c^+$, $F4/80^+$, and $B220^+$ cells, respectively. The data in FIG. 19*b*-19*g* are represented as mean±SD and were subjected to a one-way ANOVA with Dunnett's multiple comparisons tests. $P<0.05$ was considered significant, ns=not significant.

FIG. 20*a* shows the experiment schedule; EAE was induced in C57BL/6 mice, followed by intravenous injection of MSN-MOG, MSN-MOG-Ce, or left untreated, on days 15, 18, and 21 prior to flow cytometry analysis of splenocytes on day 31; n=5 biologically independent animals. FIG. 20*b*, FIG. 20*c* and FIG. 20*d* shows the expression of MHC-II on $CD11c^+$ DCs, $F4/80^+$ macrophages, and $B220^+$ cells, respectively. Data in FIG. 20*b*-20*d* are represented as mean±SD and were subjected to a one-way ANOVA with Dunnett's multiple comparisons tests, ns=not significant.

FIG. 21*a* shows the experiment schedule; EAE was induced in C57BL/6 mice, followed by intravenous injection of MSN-MOG, MSN-MOG-Ce, or left untreated, on days 15, 18, and 21 prior to flow cytometry analysis of splenocytes on day 31; n=5 biologically independent animals. FIG. 21*b* and FIG. 21*c* show the frequency and number of $CD4^+$ T-cells, respectively, in the spleens. Data in FIG. 21*b* and FIG. 21*c* are represented as mean±SD and were subjected to a one-way ANOVA with Dunnett's multiple comparisons tests, ns=not significant.

FIG. 22 is representative pseudocolor plots showing the percentages of $CD11c^+$ cells, $F4/80^+$ cells, $B220^+$ cells, and MHC-II expression on the cells in the CNS of EAE mice on day 31 after late therapeutics study with MSN-MOG and MSN-MOG-Ce. The numbers in the plots depict the percentage.

FIG. 23 is representative plots of frequency of $CD4^+$ T-cell in the cervical lymph node in EAE mice after late therapeutics with MSN-MOG and MSN-MOG-Ce.

DETAILED DESCRIPTION OF THE EXEMPLARY EMBODIMENTS

Figure 1:
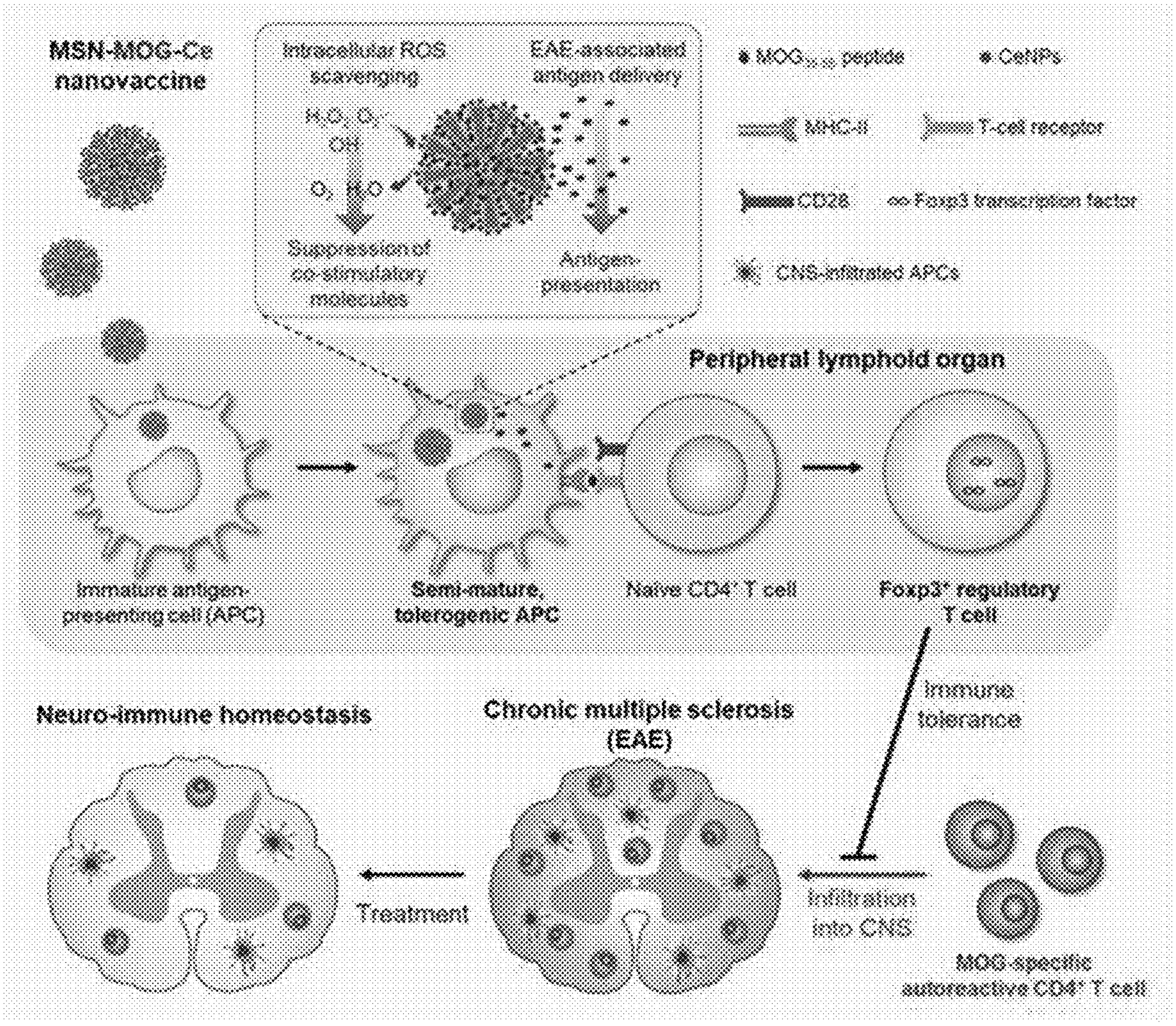
FIG. 1 shows proposed schematics of the immunosuppressive therapeutic nanoparticle vaccine to treat EAE (experimental autoimmune encephalomyelitis) via re-establishing antigen-specific immune tolerance. The accumulation of CeNPs-decorated, MOG-loaded MSNs in the APCs resulted in the reduction of intracellular ROS and expression of costimulatory molecules (CD86, CD40) on APCs, leading to the suppression of APCs activation, thus making APCs more tolerogenic. The interaction between the MOG peptide presented by MHC-II on semi-mature, tolerogenic APCs and T-cell receptor on naive $CD4^{+}$ T cells enables the induction of $Foxp3^{+}$ Tregs. The peripherally induced Tregs subsequently inhibit the infiltration of MOG-specific autoreactive $CD4^+$ T cells to the CNS. Consequently, the reduction of infiltrated $CD4^+$ T cells in CNS hampers neuronal self-destruction and prevents epitope spreading within CNS. Thus, neuro-immune homeostasis can be achieved for the treatment of late, chronic-stage multiple sclerosis.

Hereinafter, the present invention will be described in more detail with reference to examples. It would be obvious to those skilled in the art that these examples are intended to be more concretely illustrative, and the scope of the present disclosure as set forth in the appended claims is not limited to or by the examples.

EXAMPLE

Example 1: Materials

Hexadecyltrimethylammonium bromide (CTAB), ammonium hydroxide solution, phorbol 12-myristate 13-acetate (PMA), ionomycin, 6-aminohexanoic acid, formic acid, tetraethyl orthosilicate (TEOS), lipopolysaccharide from *Escherichia coli*, rhodamine B isothiocyanate (RITC), and RPMI 1640 were purchased from Sigma-Aldrich (St. Louis, MO, USA). Dulbecco's modified Eagle's medium (DMEM) was purchased from Lonza (Basel, Switzerland). 2',7-Dichlorofluorescein diacetate (H2DCFDA) was purchased from Invitrogen (Carlsbad, CA, USA). Cerium (III) nitrate hexahydrate was purchased from Alfa Aesar (Tewksbury, MA, USA). Ethanol, methanol, hydrochloric acid, and ethyl acetate were purchased from Samchun (Seoul, South Korea). Endotoxin free ultra-pure water was purchased from EMD Millipore (MA, USA). MOG35-55 peptide (sequence: MEVGWYRSPFSRWHLYRNGK) and OVA323-339 peptide (sequence: ISQAVHAAHAEINEAGR) were synthesized by Anygen (Gwangju, South Korea). Methoxy poly (ethylene glycol) succinimidyl glutarate (Mw=5000) was purchased from SunBio (Gyeonggi, South Korea). Fluorescein isothiocyanate (FITC)-conjugated anti-CD3, eFluor 450 and R-phycoerythrin (PE)-conjugated anti-F4/80, PE-Cyanine7 (PE-Cy7)-conjugated anti-CD4, APC-conjugated anti-CD11c, eFluor 450-conjugated anti-CD86, FITC-conjugated anti-CD40, PE-Cy7-conjugated anti-B220, FITC-conjugated anti-MHC-II, and APC-conjugated anti-Foxp3 monoclonal antibodies were purchased from eBioscience (CA, USA). PE-conjugated I-Ab $MOG_{35-55}$ tetramer was purchased from MBL (Japan). FcR blocking reagent, APC-conjugated anti-Foxp3, PE-conjugated anti-CD25, FITC-conjugated anti-IFN-γ, PE-Vio770-conjugated anti-CD4, APC-conjugated anti-IL-10, PE-conjugated anti-IL-17A monoclonal antibodies, $CD4^+$ T-cell isolation kit, LS column, and MidiMACS separator were purchased from Miltenyi Biotec (Bergisch Gladbach, Germany). Pacific blue-conjugated anti-mouse TCR Vα2 antibody was purchased from BioLegend (CA, USA). Alexa Fluor 647-conjugated anti-Iba1/AIF-1 monoclonal antibody was purchased from Cell Signaling Technology, Inc.

Example 2: Synthesis of Large-Pore Mesoporous Silica Nanoparticles

MSNs were synthesized according to a previous study (Nguyen, T. L., Cha, B. G., Choi, Y., Im, J. & Kim, J. Injectable dual-scale mesoporous silica cancer vaccine enabling efficient delivery of antigen/adjuvant-loaded nanoparticles to dendritic cells recruited in local macroporous scaffold. Biomaterials 239, 119859 (2020)). First, 500 μL of Fe3O4 (6 mg/mL) nanocrystals, which were prepared from an iron-oleate complex by a heat-up reaction, was mixed with 10 mL of a 0.055 M CTAB aqueous solution with vigorous stirring for 30 min. The mixture was then heated at 60 °C for 15 min before being poured into 95 mL of deionized (DI) water. Subsequently, 3 mL of ammonium hydroxide solution, 5 mL of methanol, 20 mL of ethyl acetate, and 500 μL of TEOS were added to the mixture and allowed to react overnight. The resulting nanoparticles were washed thrice with ethanol. The CTAB template and Fe3O4 nanocrystal core were removed by stirring the MSNs in ethanol containing HCl for 3 h at 60 °C. Finally, the MSNs were washed thrice with ethanol and stored in ethanol until use. To track MSN accumulation in immune cells in vivo, RITC-MSN was prepared by mixing RITC with MSNs in methanol for 48 h under dark conditions. An intensive wash was applied to completely remove the unbound RITC.

Example 3: Synthesis of Cerium Oxide Nanoparticles

6-Aminohexanoic acid (6-AHA) (10 mmol) and cerium (III) nitrate hexahydrate (2.5 mmol) were dissolved in 60 and 50 mL of DI, respectively. The 6-AHA solution was then heated. When the temperature of the solution reached 95 °C under continuous stirring, 70 μL of HCl was added. Thereafter, the cerium (III) salt solution was immediately poured into the heated 6-AHA solution under vigorous stirring. To produce CeNPs with a 3 nm diameter, the mixture was allowed to react for 1 min before washing thrice with excess acetone. The CeNPs were collected under vacuum pressure and re-dispersed in sterile DI water. To pegylate CeNPs, 10 mg CeNPs were allowed to react with 250 mg methoxy poly(ethylene glycol) succinimidyl glutarate in 20 mL ethanol at pH 8. The resulted nanoparticles were washed thrice with excess acetone and collected after being dried under vacuum pressure.

Example 4: MSN and CeNP Characterization

The porous properties of MSNs were measured using the Brunauer-Emmett-Teller (BET) method. The nanoparticle size and morphology were analyzed using transmission electron microscopy (JEM-2100F, JEOL, Akishima, Japan) and scanning electron microscopy (JSM-7000F, JEOL), respectively. Energy dispersive X-ray spectroscopy elemental mapping was conducted using a JEM-2100F field emission electron microscope (JEOL, Akishima, Japan). The concentration of cerium was measured using inductively coupled plasma-optical emission spectrometry (ICP-OES, Varian, CA, USA).

Example 5: Cell Counting Kit (CCK)-8 Cytotoxicity Assay $10^4$ RAW264.7 cells (ATCC) were seeded per well in a 96-well plate and incubated for 24 h at 37 °C. Then, various concentrations of MSNs (25, 50, 100, and 200 μg/mL) and cerium (5, 10, 20, 50, and 100 μg/mL) were incubated with the cells for the next 24 h. Finally, 10 μL of CCK-8 solution (Dojindo, Japan) was added to each well and incubated for 2 h at 37 °C. Absorbance was measured at 450 and 600 nm using a microplate reader (Thermo Fisher Scientific, MA, USA). The cell viability was calculated according to the manufacturer's instructions.

Example 6: Preparation of Peptide-Loaded MSNs

Five hundred microliters of $MOG_{35-55}$ peptide solution (1 μg/μL in DI water) and five hundred microliters $OVA_{323-339}$ peptide solution (1 μg/μL in DI water) were separately mixed with 1 mg MSNs each, and incubated for 3 h at 25 °C. Subsequently, the nanoparticles were washed in DI water three times under sterilized conditions, and the loading efficiency was measured using the Pierce BCA Protein Assay Kit (Thermo Fisher, MA, USA). The peptide-loaded nanoparticles were finally re-dispersed in saline buffer prior to retro-orbital injection using a BD insulin syringe (BD, NJ, USA). To prepare MSN-MOG-Ce, $MOG_{35-55}$-loaded MSNs were mixed with 1 mg CeNPs (2 mg/mL) in DI water and gently shaken for 5 min. The mixture was then centrifuged (10,000×g, 5 min) and washed twice with DI water to remove unbound CeNPs. The loaded CeNPs were measured using the ultraviolet-visible method at 310 nm. Finally, the nano-composition was re-dispersed in saline buffer prior to retro-orbital injection using a BD Insulin Syringe.

Example 7: Animals

Female C57BL/6 mice aged 9 weeks were purchased from OrientBio (Seongnam, South Korea). The experimental and control animals were co-housed under specific pathogen-free condition during the study. Female OT-II (C57BL/6-Tg (TcraTcrb)425Cbn/Crl) mice of 7-9-week age were used for in vitro generation of Tregs. OT-II mice were a kind gift from Prof. Suk-Jo Kang from Korea Advanced Institute of Science and Technology (KAIST). Animals were acclimatized for at least 1 week before immunization. At the end of each study, mice were euthanized by carbon dioxide (flow rate: 3 L/min). All experiments were approved by the Institutional Animal Care and Use Committee of Sungkyunkwan University (SKKUIACUC, No. 2020-01-15-1).

Example 8: In Vivo Cellular Uptake in Spleen

Twenty-four hours prior to intravenous administration of RITC-MSN into C57BL/6 mice, splenocytes were isolated. The cells were stained with FcR blocking reagent for 10 min at 4 °C and washed. Subsequently, cells were stained with antibodies against CD11c, F4/80, B220, and CD3 for 20 min at 4 °C. Positive signals from stained surface markers were gated among the $RITC^+$ cells to determine the cell types that engulfed RITC-MSN.

Example 9: EAE Induction

EAE was induced in female C57BL/6 mice aged 10-11 weeks using a kit (EK-2110) from Hooke Laboratory (Lawrence, MA, USA). Briefly, on day 0, mice were subcutaneously injected with an emulsion containing $MOG_{35-55}$ peptide and complete Freund's adjuvant (CFA), in the lower and upper back. After 2 and 24 h, the animals were intraperitoneally injected with pertussis toxin (PTX) according to the manufacturer's instructions. EAE clinical score was evaluated after day 8, post-EAE induction based on the standard protocol in a blinded manner (0, no obvious symptoms; 0.5, tip of tail was limp; 1, limp tail; 1.5, limp tail and hind leg inhibition; 2, limp tail and weakness of hind legs; 2.5, limp tail and dragging of hind legs; 3, complete paralysis of hind legs; 3.5, complete paralysis of hind legs and hind legs together on one side of the body; 4, full hind leg and partial front leg paralysis; 4.5 full hind leg and partial front leg paralysis, no movement). Paralyzed mice were given easier access to water and food. Mice were euthanized if any of the following conditions were observed unable to eat, unresponsive when scored as 4, when scored as 4 for two consecutive days, both hind limbs and forelimbs were completely paralyzed.

Example 10: Therapeutic Vaccine Studies

For semi-therapeutic treatment (vaccination after disease establishment but before the onset of symptoms), the mice were injected with different formulations of material components (MSN, MOG, MSNMOG, MSN-OVA) on days 4, 7, and 10 after EAE induction or left untreated. FIG. 9 shows the dose for each formulation in detail. To examine the immune responses after semi-therapeutic treatment of MSN-OVA, MSN-MOG, or no treatment in EAE-induced mice, mice from each group were euthanized for spleen and spinal cord collection on day 10 after the final injection (the respective treatments were administered on days 4, 7, and 10 post-EAE induction). For the early therapeutic study, EAE-induced mice were injected with MSN-MOG or left untreated on days 12, 15, and 18. For the late therapeutic study, EAE-induced mice were injected with MSN-MOG or left untreated on days 15, 18, and 21.

Example 11: Histology

The vertebral columns were collected on day 50 post-EAE induction and fixed in 4% buffered formaldehyde solution for 48 h. The tissues were then washed in DI water before decalcification in an aqueous solution containing 4% formic acid and 4% hydrochloric acid for 72 h. The acid solution was replaced daily. Subsequently, the mouse spines were neutralized in an ammonia solution, washed in DI water, and embedded in paraffin. The tissues were cut into 4-μm thick sections. Finally, the spinal cord sections were stained with H&E, and an optical microscope (ECLIPSE Ti-U, Nikon, Japan) was used to visualize them.

Example 12: Tissue Processing

Spleens were excised and processed by mechanical disruption using a 70 μm cell strainer. Cells were then centrifuged for 5 min, 400×g, 4 °C and treated with ammonium-chloride-potassium (ACK) lysing buffer (Lonza) for 4 min to remove red blood cells. Splenocytes were then filtered through a 40 μm cell strainer and washed in cold PBS. Spinal cords were dissociated in PBS containing 1 mg/mL collagenase type IV and 20% EDTA/trypsin and incubated at 37 °C for 20 min. RPMI 1640 containing 10% fetal bovine serum was added to each sample to inhibit enzymatic activity, and the cells were filtered through a 40 μm cell strainer. The cells were collected by centrifugation according to standard protocol.

Example 13: Flow Cytometry

Immediately after stimulation or obtaining single-cell suspensions from tissues, cells were incubated with the FcR blocking reagent for 10 min at 4 °C to prevent non-specific binding. Then, antibodies against surface markers CD11c, B220, F4/80, CD86, CD40, MHC-II were used to stain for APC analysis. For T-cell analysis, I-Ab $MOG_{35-55}$ tetramer was used to stain the cells for 40 min at 4 °C, then antibodies against CD3 and CD4 were used to stain the cells for 20 min at 4 °C before being washed in FACS buffer. After that, the cells were either analyzed immediately or fixed and permeabilized for transcription factor staining. Foxp3/Transcription Factor Staining buffer set (eBioscience 00-5523-00, CA, USA) was used to fix and permeabilize the cells prior to staining with antibody against Foxp3. Suitable isotype control antibodies were used as the negative controls. For the analysis of lba1 expression in CNS cells, the cells were first fixed and permeabilized by Intracellular Fixation & Permeabilization buffer set (eBioscience 88-8824-00, CA, USA) prior to lba1 staining for 1 h. The stained cells were analyzed using a MACSQuant VYB flow cytometer (Miltenyi Biotec, Bergisch Gladbach, Germany).

Figure 16:
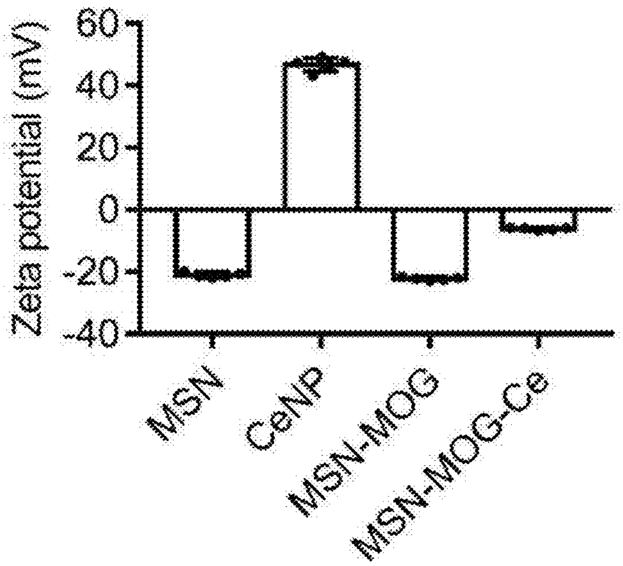
FIG. 16 shows the zeta potential of MSN, CeNPs, MSN-MOG and MSN-MOG-Ce.

All cells were gated based on forward-scatter and side-scatter characteristics to exclude dead cells and debris. Thereafter, the forward-scatter height (FSC-H) and forward-scatter area (FSC-A) parameters were used to determine the single-cell population. Finally, the frequency of positively stained cells for each marker was recorded based on the isotype control antibodies. Examples of the gating strategies are shown in FIG. 16. Data were analyzed using FlowJo X 10.0 (Becton, Dickinson and Company).

Example 14: Cytokine Recall Study

Half the mice from each group were euthanized for splenocyte collection and on day 3, and other half were euthanized for splenocyte collection on day 10 after the final injection. Then, splenocytes ($1\times10^6$) isolated from each mouse were restimulated with 20 μg/mL of $MOG_{35-55}$ peptide for 72 h. The culture supernatant was collected and stored at −80 °C until use. The secreted cytokines IL-10, GM-CSF, TNF-α, and IL-17A were quantified by enzyme-linked immunosorbent assay (ELISA, R&D Systems, Minneapolis, MN, USA) according to the manufacturer's instructions.

Example 15: BMDC Culture

Bone marrow cells from the femurs of C57BL/6 mice were isolated and filtered using a 70 μm cell strainer. The cells were then cultured in complete RPMI 1640 supplemented with 10% heat-inactivated fetal bovine serum, 1% penicillin/streptomycin (Sigma-Aldrich), 50 μM β-mercaptoethanol (Sigma-Aldrich), and 20 ng/mL GM-CSF (PeproTech, NJ, USA). The culture medium was refreshed on days 3 and 6. Differentiated cells from days 7 to 9 were used for the cell activation study.

Example 16: $CD4^+$ T Cell Isolation and Culture

Spleen and lymph nodes of OT-II mice were first processed to obtain single-cell suspensions. Purified $CD4^+$ T cells were isolated by magnetic activated cell sorting (MACS) using $CD4^+$ T cell isolation kit (Miltenyi Biotec, 130-104-454). OT-II $CD4^+$ T cells were then washed and cultured with BMDCs in complete RMPI 1640 supplemented with 10% heat-inactivated fetal bovine serum (Gibco), 1% penicillin/streptomycin (Sigma-Aldrich), 50 μM β-mercaptoethanol (Sigma-Aldrich) at 37 °C in 5% $CO_2$.

Example 17: Apoptosis Assay

BMDCs were seeded in 6-well culture plates ($1\times10^6$ cells/well). The cells were then co-incubated for 48 h with pegylated CeNPs at different cerium concentrations. Subsequently, the cells were washed with FACS buffer and stained using the FITC Annexin V Apoptosis Kit with PI (BioLegend, CA, USA) according to the manufacturer's instructions before performing flow cytometry analysis.

Example 18: BMDC Activation Study

BMDCs were seeded in 6-well culture plates ($1\times10^6$ cells/well). The cells were then treated with either pegylated CeNPs (Ce, 50 μM cerium), $OVA_{323-339}$ peptide (OVA, 1 μg/m L), pegylated CeNPs and $OVA_{323-339}$ peptide (Ce+OVA), MSN-MOG, MSN-MOG-Ce, or left untreated for 24 h, followed by stimulation with 1 μg/mL or 100 ng/mL LPS for the next 24 or 12 h. Finally, the cells were washed and stained with $H_2DCFDA$ and antibodies against CD11c, CD86, CD40, and MHC-II before flow cytometry analysis.

Example 19: T-Cell Differentiation In Vitro

Day 7 BMDCs were treated with PBS (control), pegylated CeNPs (Ce, 50 μM cerium), $OVA_{323-339}$ peptide (OVA, 1 μg/mL), or pegylated CeNPs plus OVA (Ce+OVA) in 24 h, following by LPS treatment (1 μg/mL) in the next 24 h. Then BMDCs were washed twice and co-cultured with OT-II $CD4^+$ T cells at 1:10 (30,000:300,000) BMDCs to T-cell ratio for 72 h. Subsequently, the cells were stimulated in a culture medium containing PMA (100 ng/mL), ionomycin (1 μg/mL) for 5 h and protein transport inhibitor (GolgiStop, BD Bioscience) in the last 3 h. Finally, cells were fixed, permeabilized, and stained with antibodies against Vα2, CD4, CD25, Foxp3, IL-10, IFN-γ, IL-17A before flow cytometry analysis.

Example 20: ROS-Scavenging Study

BMDCs were seeded in 6-well culture plates ($1\times10^6$ cells/well). The cells were then treated with either MSN-MOG or MSN-MOG-Ce, or left untreated for 24 h, followed by stimulation with 100 ng/mL LPS to induce excessive intracellular ROS for the next 12 h. Subsequently, the cells were stained with 5 μM $H_2DCFDA$ and CD11c antibody for 20 min at 4 °C before being washed and analyzed by flow cytometry.

Example 21: Statistics and Reproducibility

EAE clinical score values were expressed as the mean±standard error (SE). All other values are expressed as mean±standard deviation (SD) unless indicated otherwise. An unpaired two-tailed t-test was performed to compare the statistical significance between the two groups. For multiple comparisons, one-way ANOVA was performed using GraphPad Prism 7.00.

Results

Figure 7A:
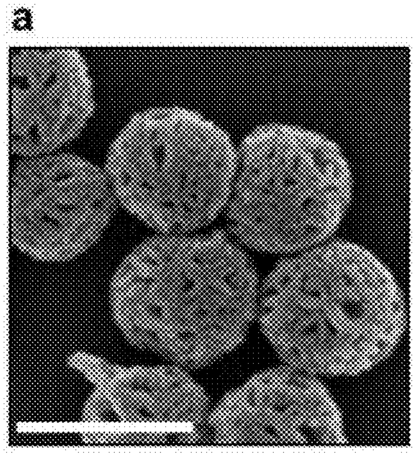
FIGS. 7*a*, 7*b* and 7*c* show the results of MSN characterization.
Figure 7B:
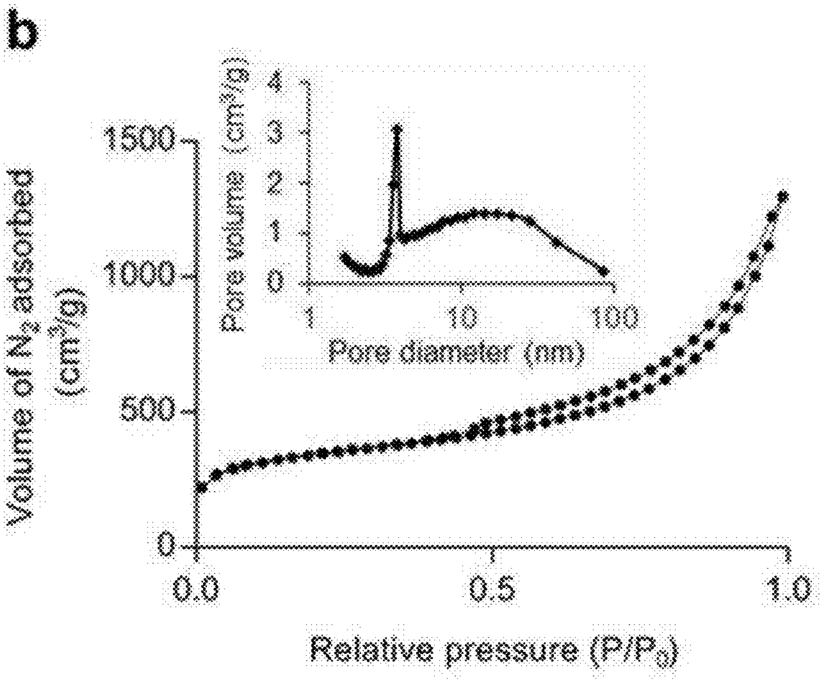
Figure 7C:
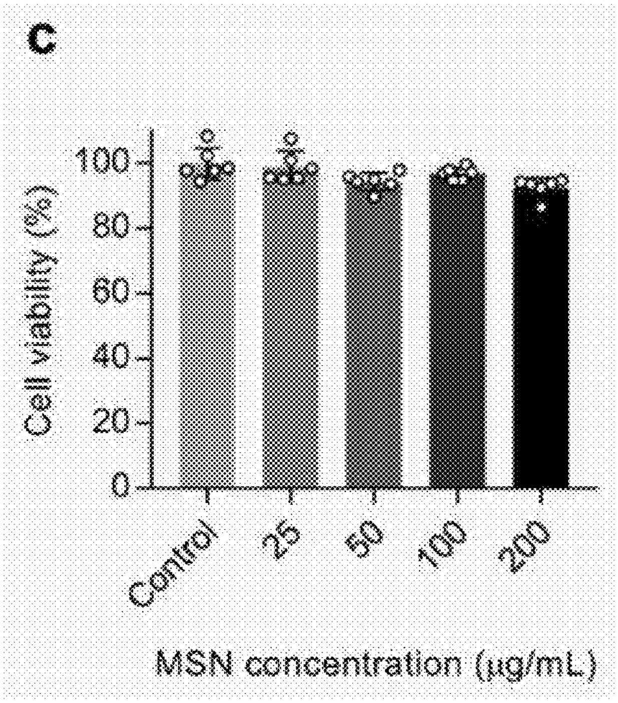
Figure 8:
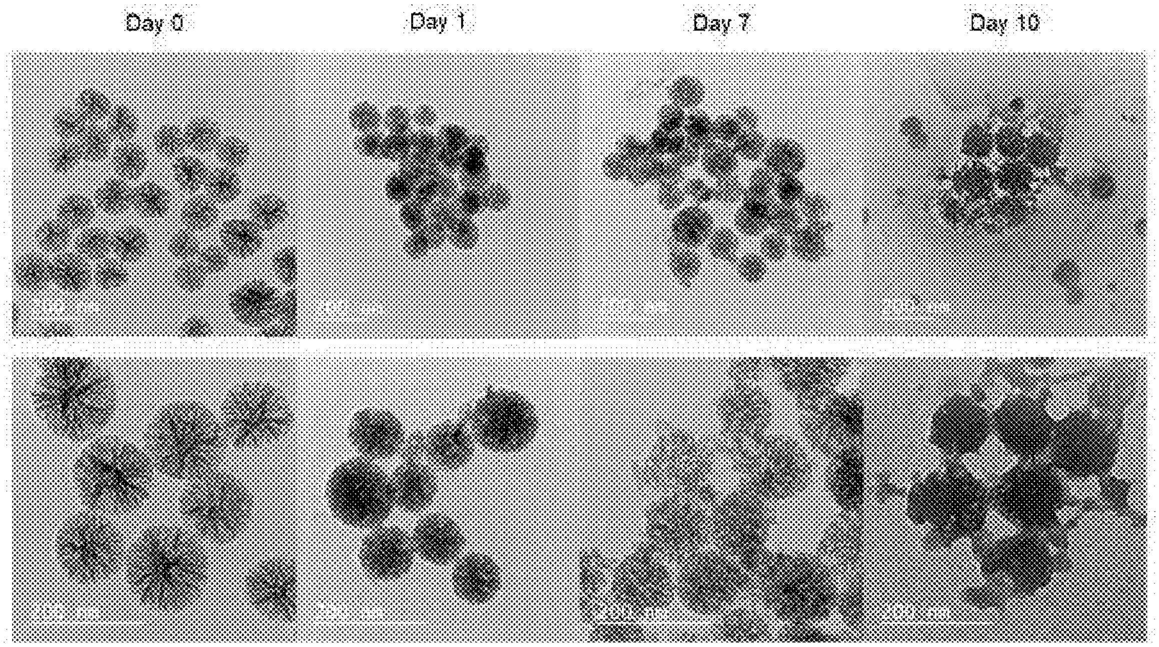
FIG. 8 shows in vitro degradation of MSNs, and shows TEM images demonstrating the degradation of MSNs in phosphate-buffered saline at 37 °C over time.

1. Myelin Oligodendrocyte Glycoprotein (MOG)-Loaded MSNs Suppresses EAE Development in Semi-Therapeutic Study First, MSNs with 10-30-nm large mesopores along with 3-nm conventional mesopores were synthesized according to previous reports (Kwon, D. et al. Extra-large pore mesoporous silica nanoparticles for directing in vivo M2 macrophage polarization by delivering IL-4. Nano Lett. 17, 2747-2756 (2017)., Nguyen, T. L., Cha, B. G., Choi, Y., Im, J. & Kim, J. Injectable dual-scale mesoporous silica cancer vaccine enabling efficient delivery of antigen/adjuvant-loaded nanoparticles to dendritic cells recruited in local macroporous scaffold. Biomaterials 239, 119859 (2020).) (FIG. 2*a*, FIG. 7). Before the in vivo tests, the cytotoxicity of various concentrations of MSNs was examined, showing that the MSNs were highly biocompatible (FIG. 1*d*). The biodegradability of MSNs has been confirmed in phosphate-buffered saline (PBS) at physiological pH (FIG. 8) and under physiological conditions of lysosomes (Croissant, J. G., Fatieiev, Y. & Khashab, N. M. Degradability and clearance of silicon, organosilica, silsesquioxane, silica mixed oxide, and mesoporous silica nanoparticles. Adv. Mater. 29, 1604634 (2017).). In line with previous studies (Kwon, D. et al. Extra-large pore mesoporous silica nanoparticles for directing in vivo M2 macrophage polarization by delivering IL-4. Nano Lett. 17, 2747-2756 (2017)., Bindini, E. et al. Following in situ the degradation of mesoporous silica in biorelevant conditions: at last, a good comprehension of the structure influence. ACS Appl. Mater. Interfaces 12, 13598-13612 (2020).), the present inventors demonstrated that the systemic administration of MSNs led to the accumulation of nanoparticles in the spleen (FIG. 2*b*), which may be attributed to the intrinsic capacity of the mononuclear phagocytic system to massively capture foreign nanoparticles. APCs, including $CD11c^+$ dendritic cells (DCs), $F4/80^+$ macrophages, and $B220^+$ B cells were the major cell populations that engulfed MSNs in the spleen (FIG. 2*c*). Owing to their large pore size, MSNs used in this study exhibited high antigen-loading capacity; thus, large-pore MSNs could carry antigen ($MOG_{35-55}$ peptide), equivalent to that used in previous studies (Hunter, Z. et al. A biodegradable nanoparticle platform for the induction of antigen-specific immune tolerance for treatment of autoimmune disease. ACS Nano 8, 2148-2160 (2014)., Cho, J. J. et al. An antigen-specific semi-therapeutic treatment with local delivery of tolerogenic factors through a dual-sized microparticle system blocks experimental autoimmune encephalomyelitis. Biomaterials, 79-92 (2017). and Saito, E. et al. Design of biodegradable nanoparticles to modulate phenotypes of antigen-presenting cells for antigen-specific treatment of autoimmune disease. Biomaterials, 119432 (2019).) at a substantially lower dose (FIG. 2*d* and FIG. 9).

Figure 2A:
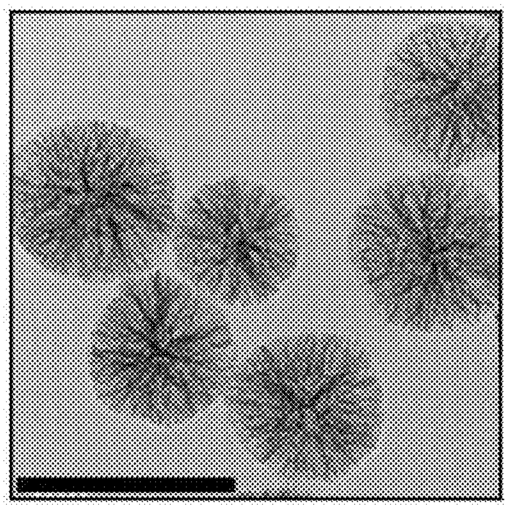
FIGS. 2*a*, 2*b*, 2*c*, 2*d*, 2*e*, 2*f*, and 2*g* show experimental data of intravenous injection of myelin oligodendrocyte glycoprotein (MOG)-loaded MSNs which suppressed EAE development.
Figure 2B:
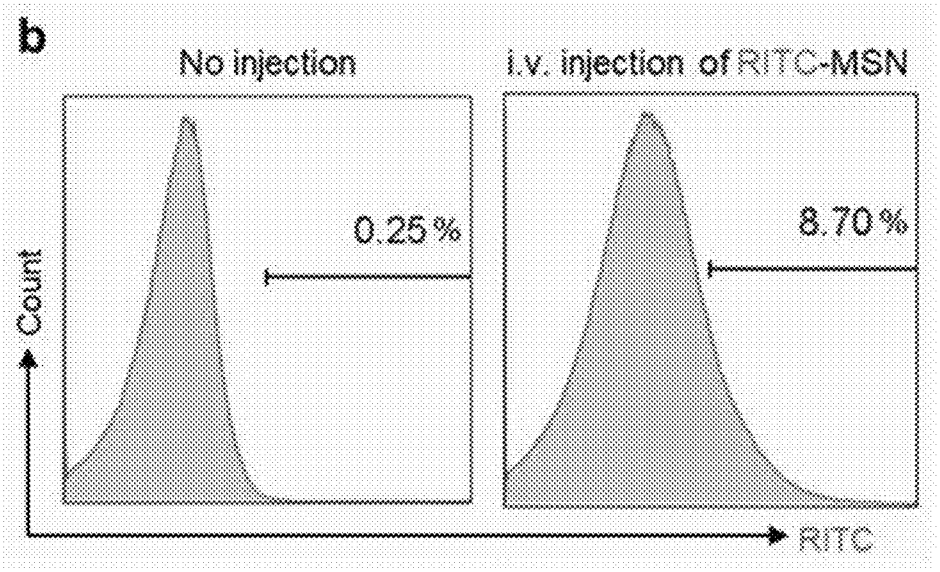
Figure 2C:
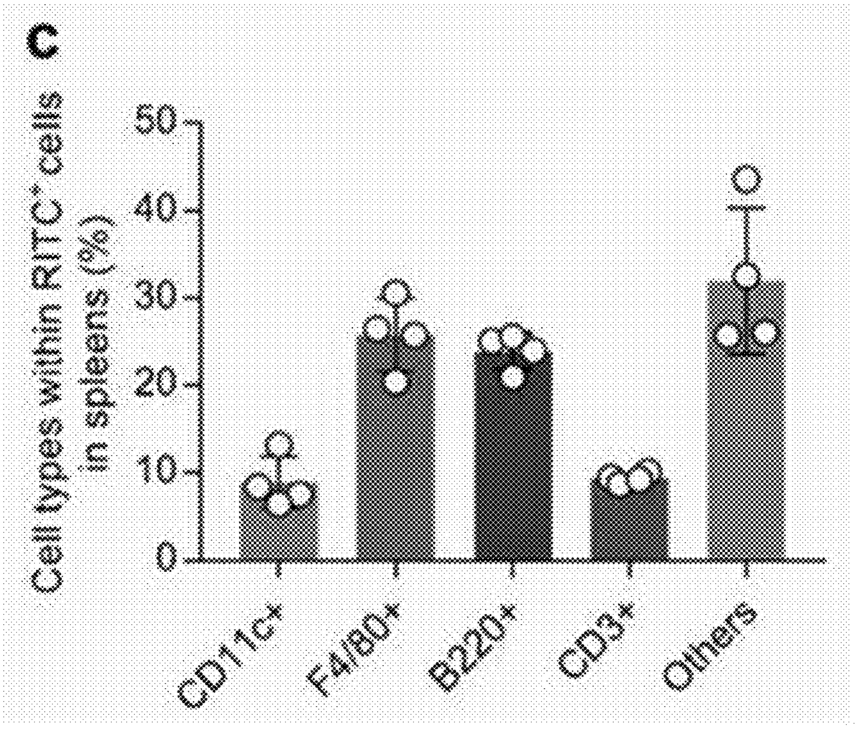
Figure 2D:
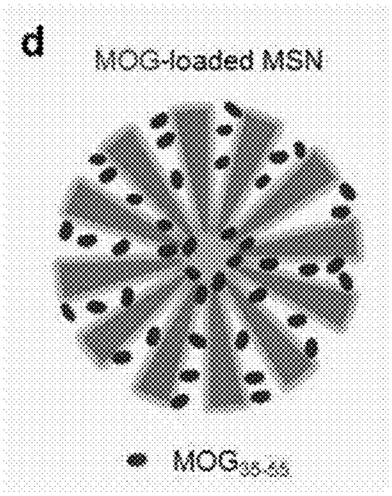
Figure 2E:
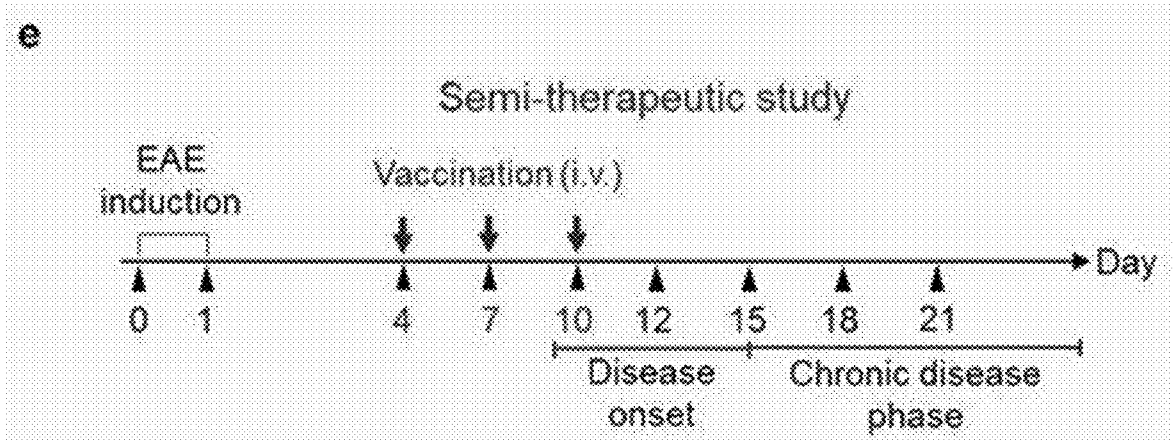
Figure 2F:
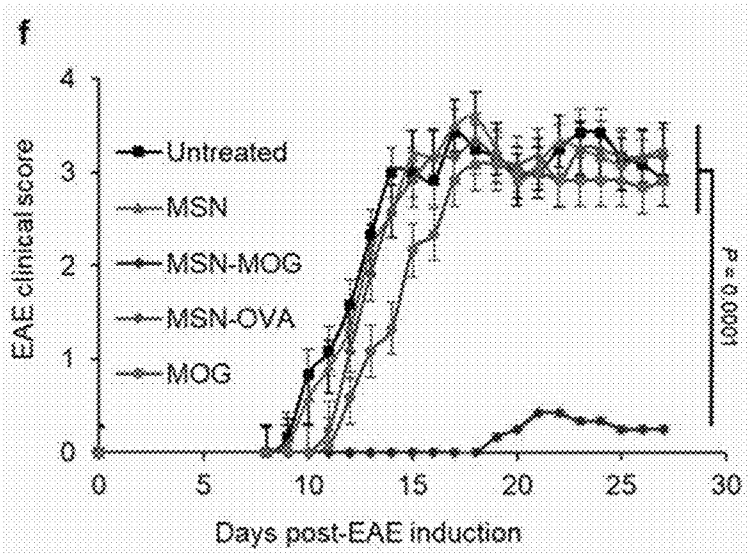
Figure 2G:
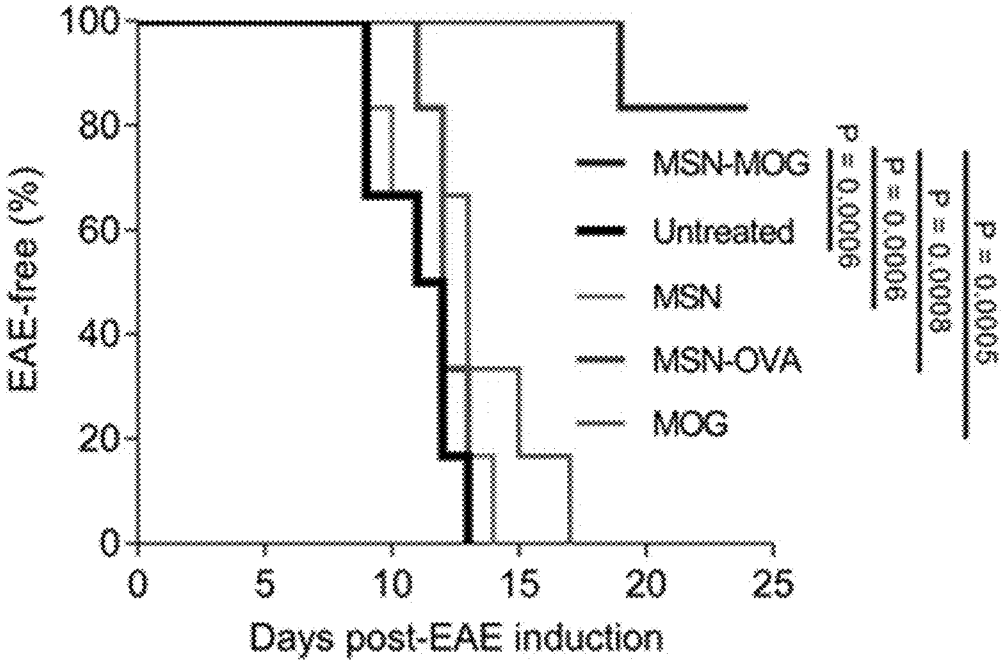
Figure 10A:
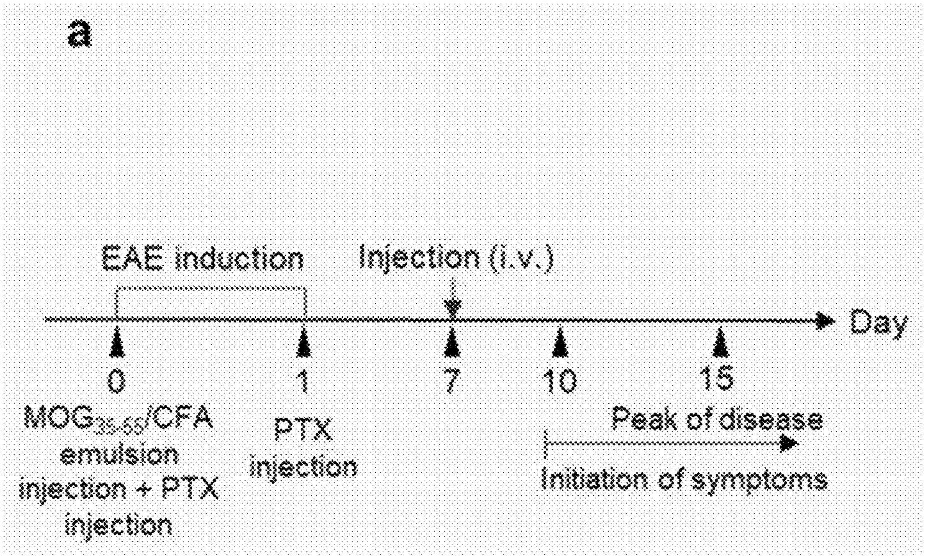
FIGS. 10*a*, 10*b*, and 10*c* show the effect of MSN amount on semi-therapeutic efficacy.
Figure 10B:
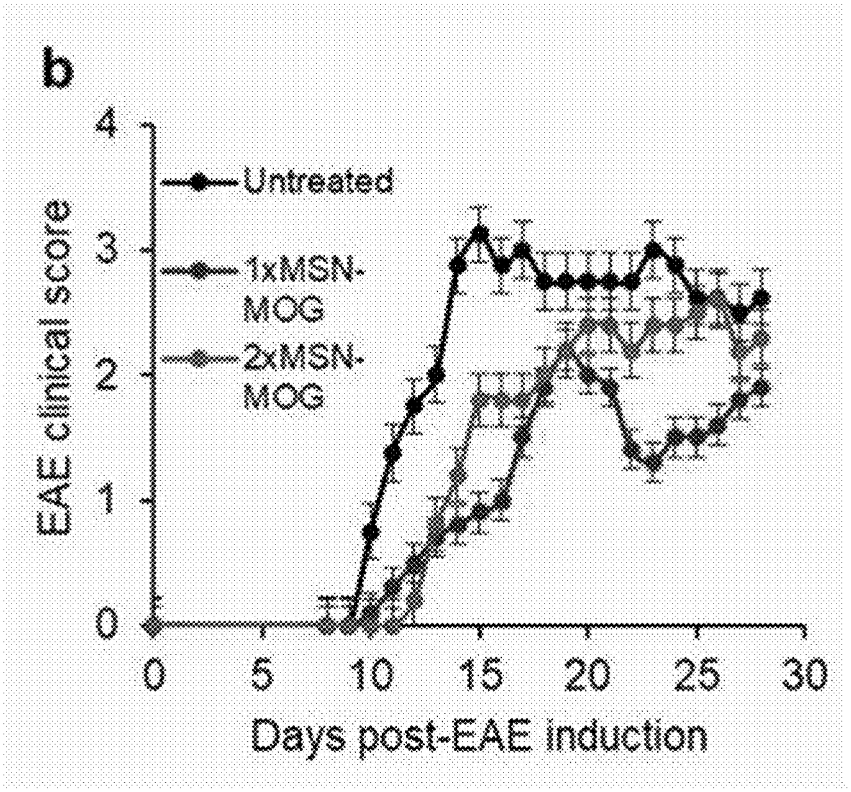
Figure 10C:
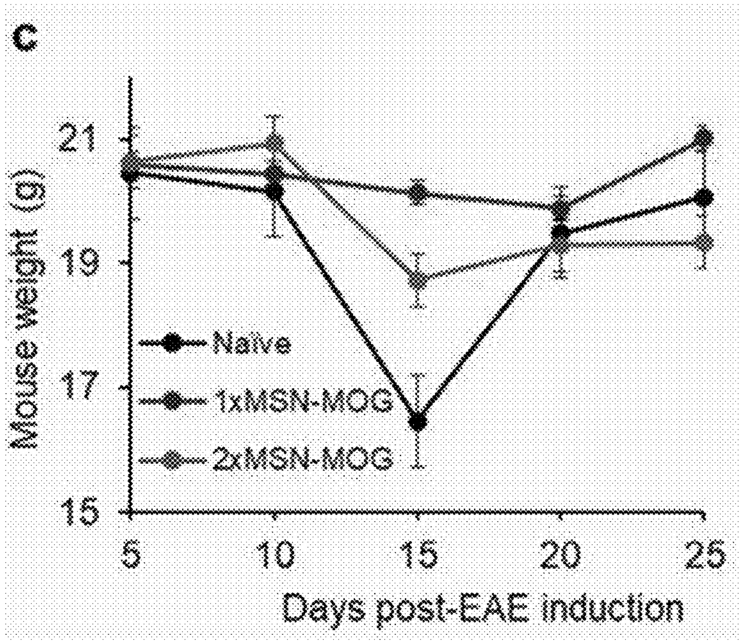

The present inventors tested the hypothesis of the present disclosure in EAE-induced C57BL/6 mice (FIG. 2*e*). Intravenous injection of bare MSNs into EAE-induced mice prior to disease onset (days 4, 7, and 10; semi-therapeutics) was unable to prevent typical EAE progression (FIG. 2*f*). Injecting soluble MOG slightly delayed EAE progression, whereas MOG-loaded MSNs (MSNMOG) markedly impeded EAE development, resulting in a high percentage of healthy animals (FIG. 2*g*). These results indicate that loading antigens on MSNs is critical for suppressing EAE development. Conversely, the $OVA_{323-339}$ peptide (unrelated peptide antigen from ovalbumin)-loaded MSNs (MSN-OVA) did not suppress EAE development, indicating that the reduction in disease severity induced by MSN-MOG was antigen-specific. Meanwhile, the increase in nanoparticle amount when maintaining MOG peptide dose was unable to show comparable benefits (FIG. 10).

Figure 3A:
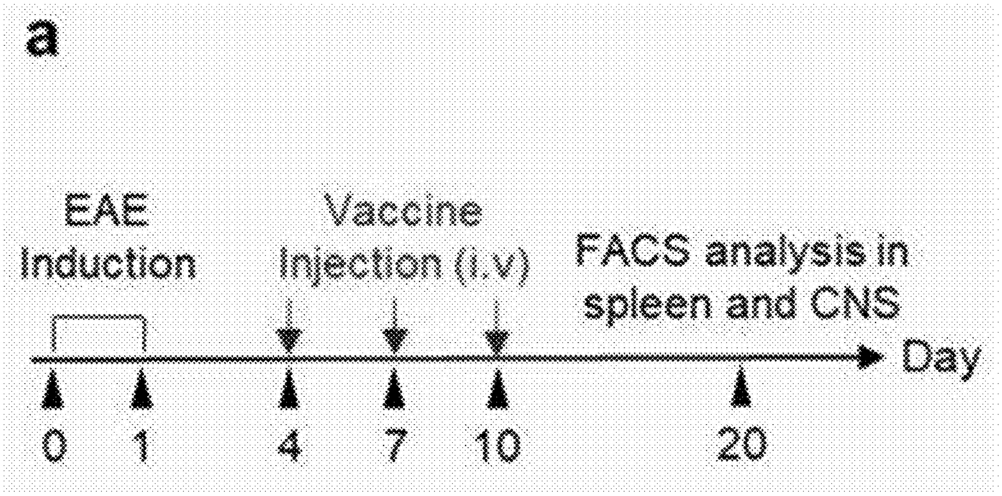
Figure 3B:
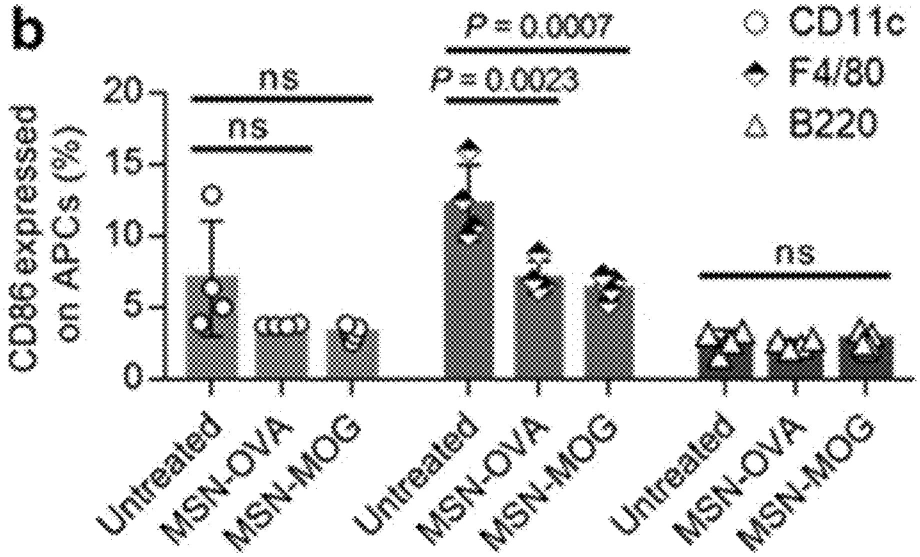
Figure 3C:
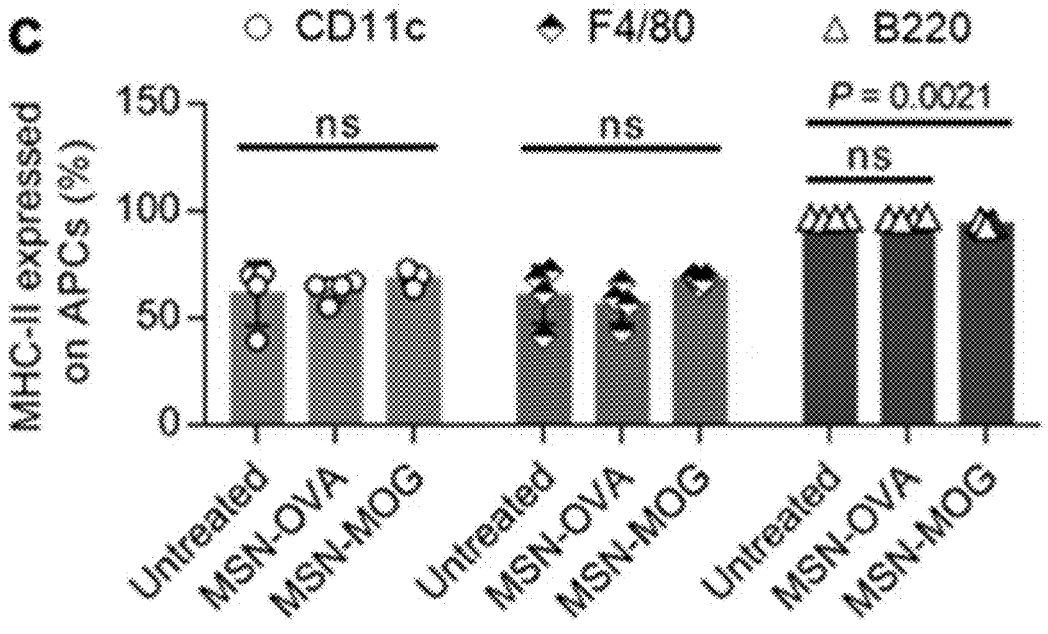
Figure 11A:
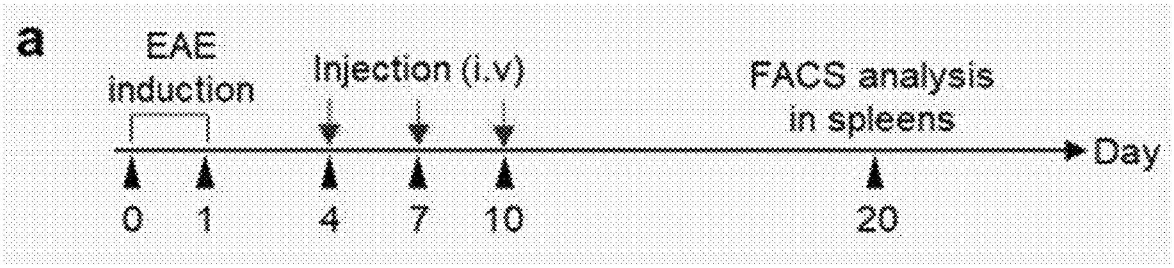
FIGS. 11*a*, 11*b*, and 11*c* show the analysis of APCs in spleens after administering semi-therapeutics.
Figure 11B:
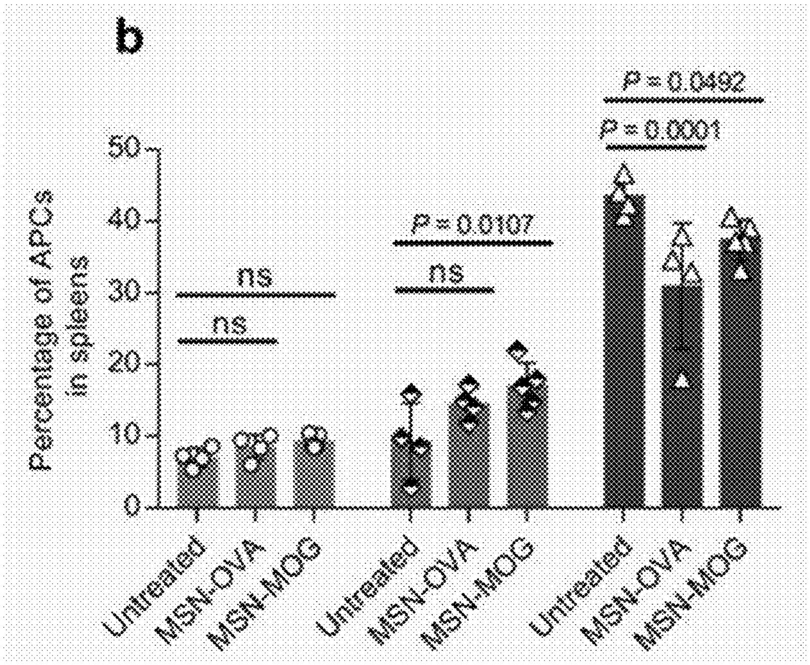
Figure 11C:
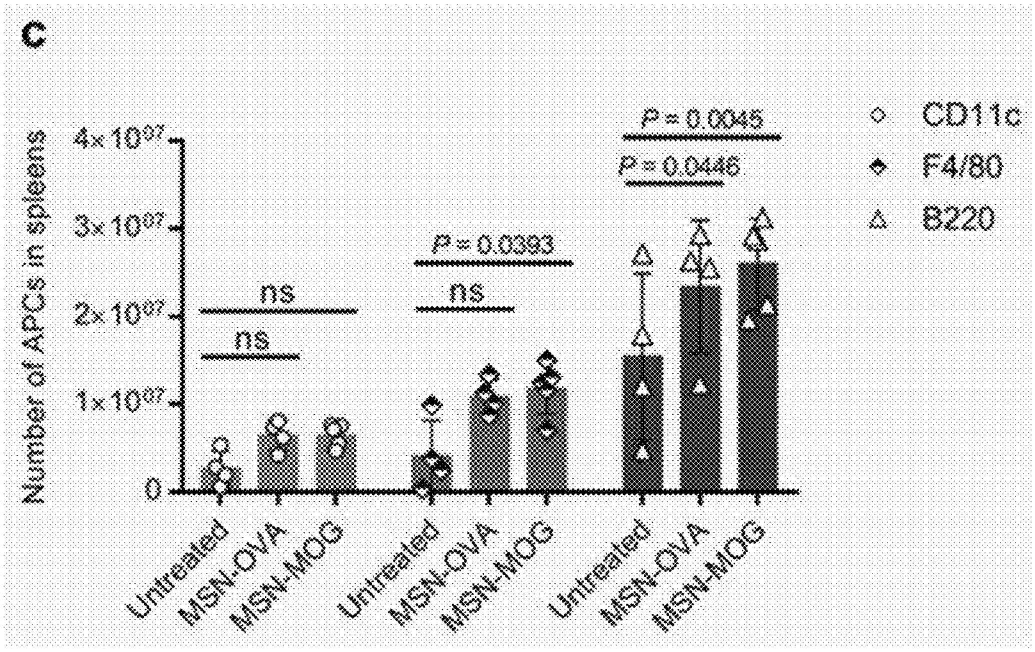

2. MOG-Loaded MSN Vaccine Generates Induced Tregs and Antigen-Specific Tolerogenic Immune Responses The present inventors evaluated cellular responses in EAE-induced mice after MSN-MOG injection to gain a better insight into the mechanism underlying immune tolerance. Phenotypic alterations in $CD11c^+$ DCs, $F4/80^+$ macrophages, and $B220^+$ B cells in the spleen, were examined by flow cytometry after vaccination (FIG. 3*a*). CD86 expressions on $F4/80^+$ macrophages were significantly lower in the MSN-MOG group than those in the untreated group (FIG. 3*b*). No significant difference in the activation of MHC class II (MHC-II) on APCs between the three groups was observed (FIG. 3*c*); indicating that antigen presentation by MHC-II was not affected by immunization. The number of APCs increased (FIG. 11), while the expression of activation markers on APCs did not increase significantly. These data suggest that systemic administration of peptide antigen (MOG)-loaded MSNs did not promote APC maturation in the lymphoid organ in EAE mice, which is necessary for the polarization of naive T cells into Tregs and/or anergic T cells.

Figure 3D:
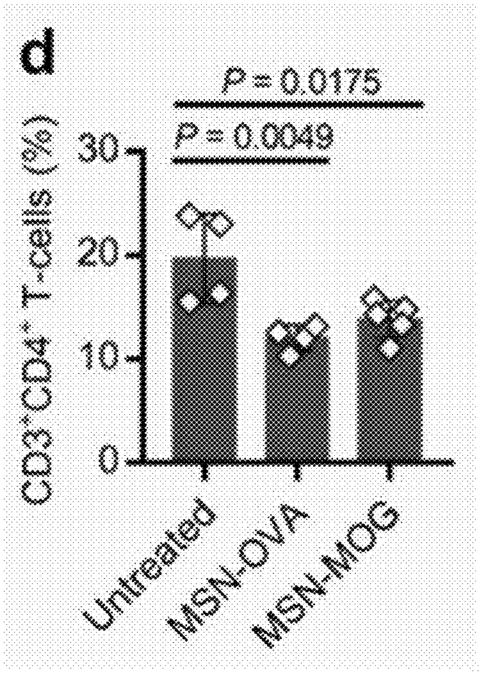
Figure 3E:
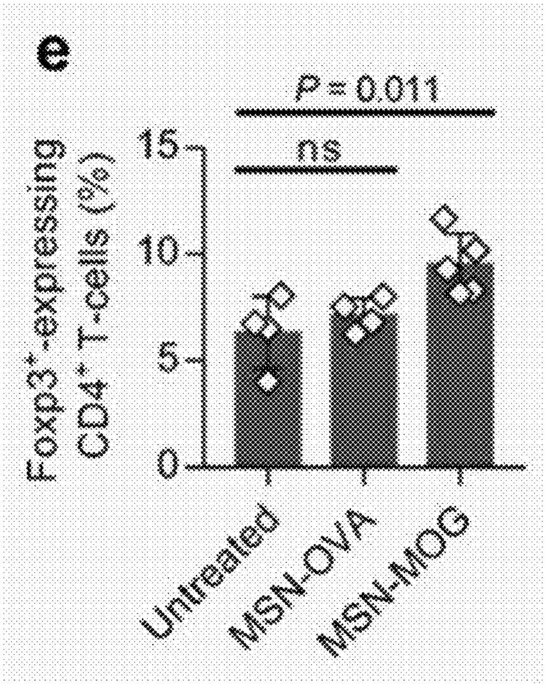
Figure 3F:
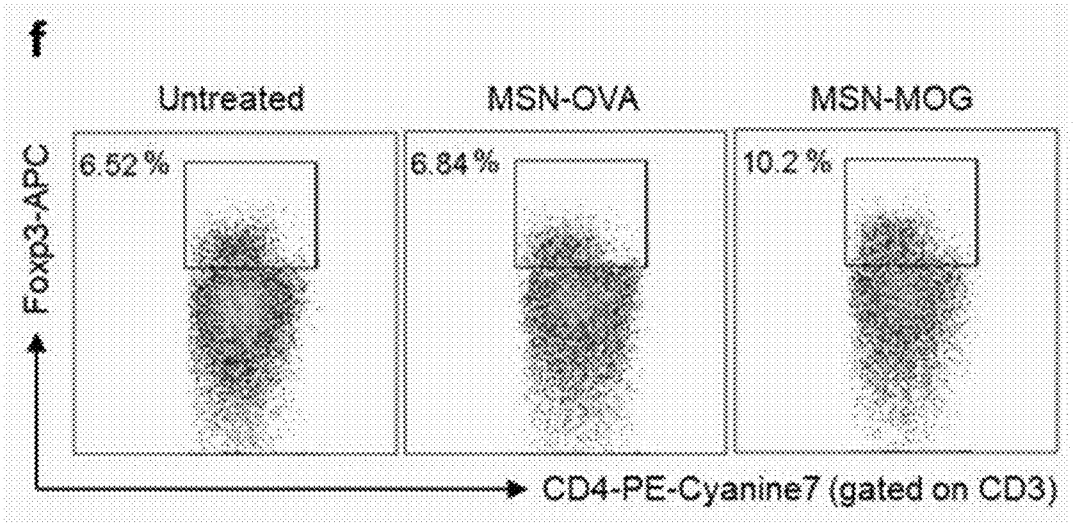
Figure 3G:
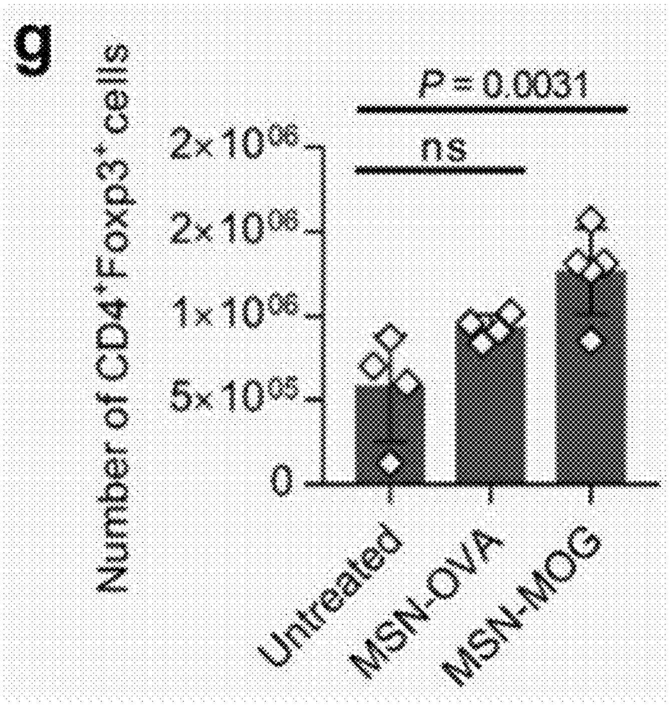

Given the inability of MSN-MOG to activate splenic APCs in EAE mice, the present inventors further examined whether MSN-MOG administration could induce $Foxp3^+$ Tregs. Following treatment with peptide-loaded MSNs, the present inventors observed a decrease in the percentage of splenic $CD4^+$ T cells on day 20 (FIG. 3*d*). In contrast, there were noticeable increases of both frequencies and numbers of $Foxp3^+$ Tregs in mice vaccinated with MSN-MOG (FIG. 3*e*, FIG. 3*f* and FIG. 3*g*). These observations suggest that the systemic delivery of self-antigen (MOG)-loaded MSNs modified the cellular composition of the spleen into more tolerogenic T cell population in the EAE mice, which is a desirable change to treat EAE.

Figure 3H:
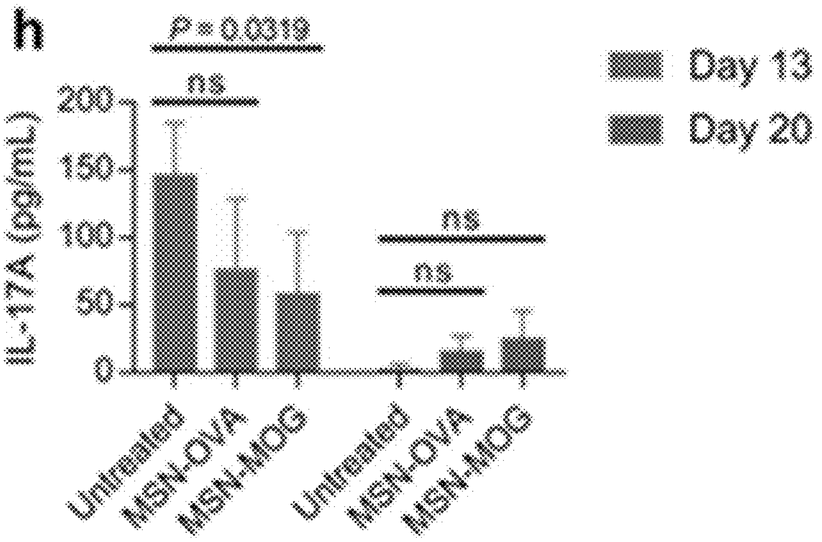
Figure 3I:
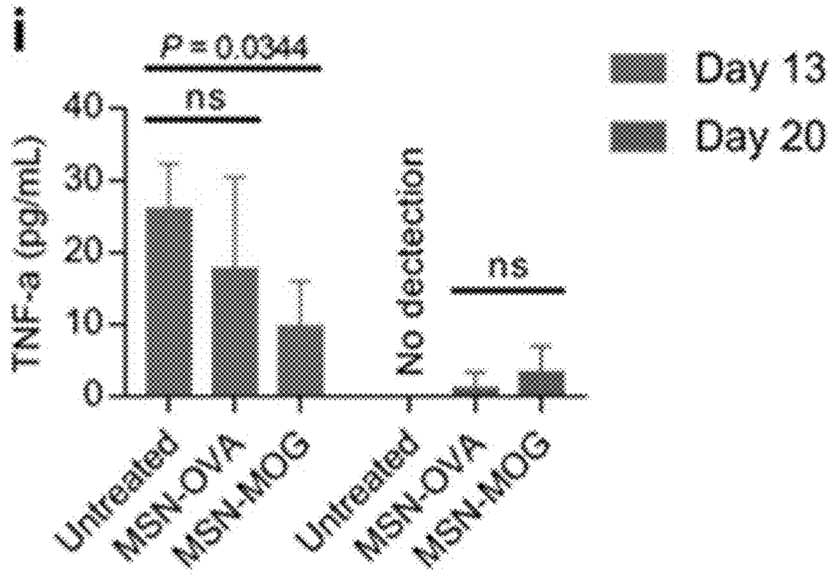
Figure 3J:
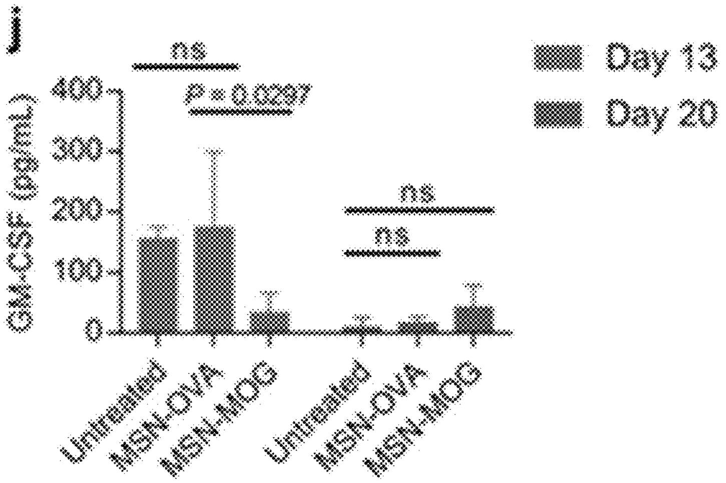
Figure 3K:
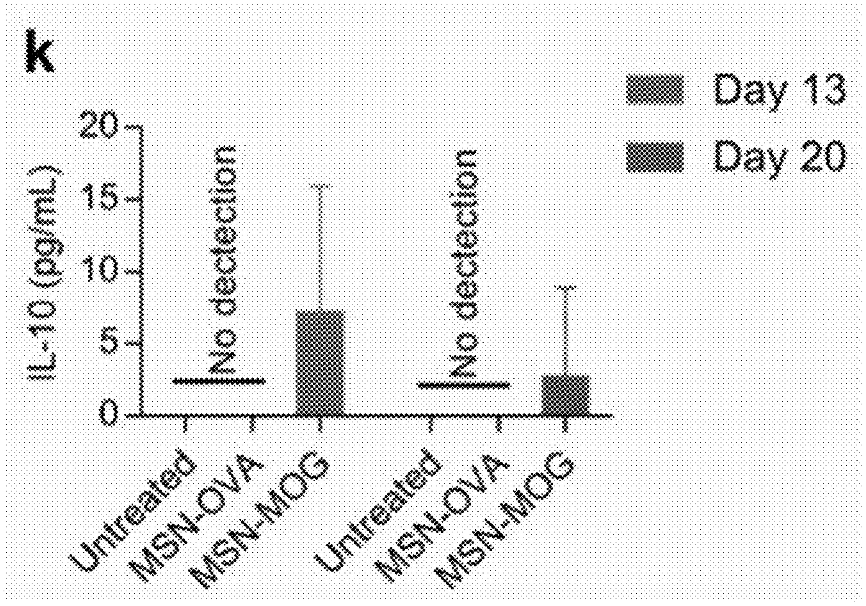
Figure 3I:
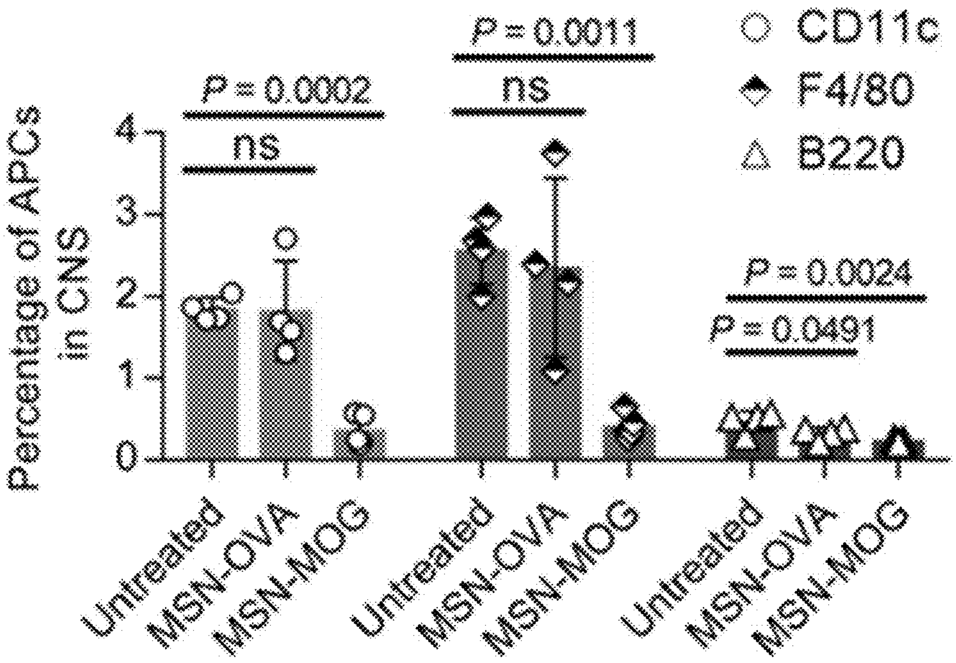

The present inventors next evaluated the responsiveness of immune cells retrieved from spleen upon re-stimulation with EAE-associated antigens (MOG) at different time points (days 13 and 20 after EAE induction, corresponding to days 3 and 10 after the last semi-therapeutic intervention) to confirm whether an antigen-specific tolerogenic environment was established. Interleukin 17A (IL-17A) and tumor necrosis factor-α (TNF-α), the central mediators of EAE and MS progression, were significantly lower in the MSN-MOG-treated group than in the untreated group (FIG. 3*h* and FIG. 3*i*). Similarly, granulocyte-macrophage colony-stimulating factor (GM-CSF) production, a key recruitment factor that attracts APCs and pathogenic monocyte-derived cells to the CNS31, was significantly inhibited in the MSN-MOG-treated group (FIG. 3*j*). The present inventors detected IL-10 in the MSN-MOG-injected group, but not in the untreated or MSN-OVA groups (FIG. 3*k*). IL-10 is a potent anti-inflammatory cytokine that plays a vital role in hampering immune responses against self-antigens.

Figure 3M:
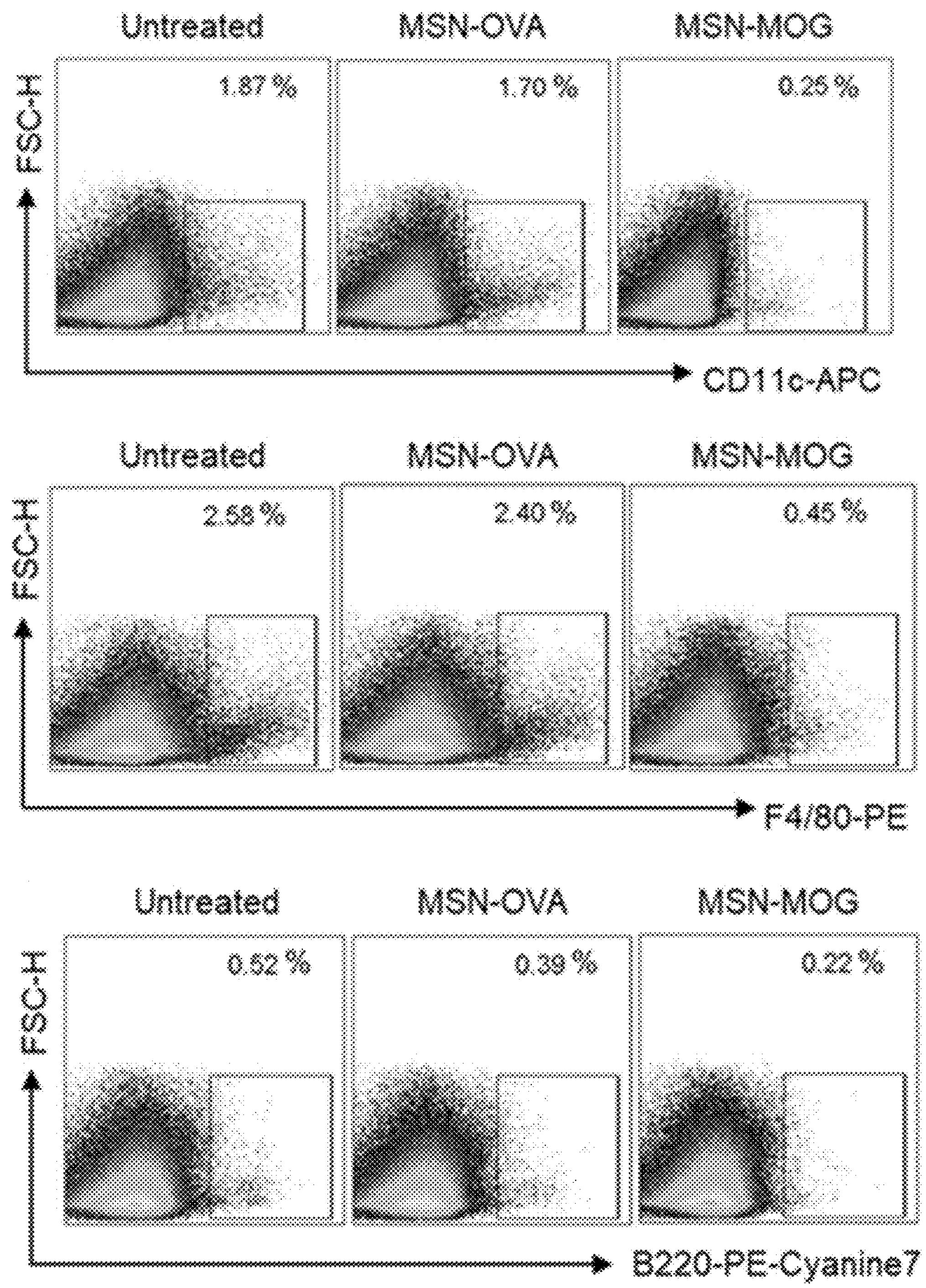
Figure 3N:
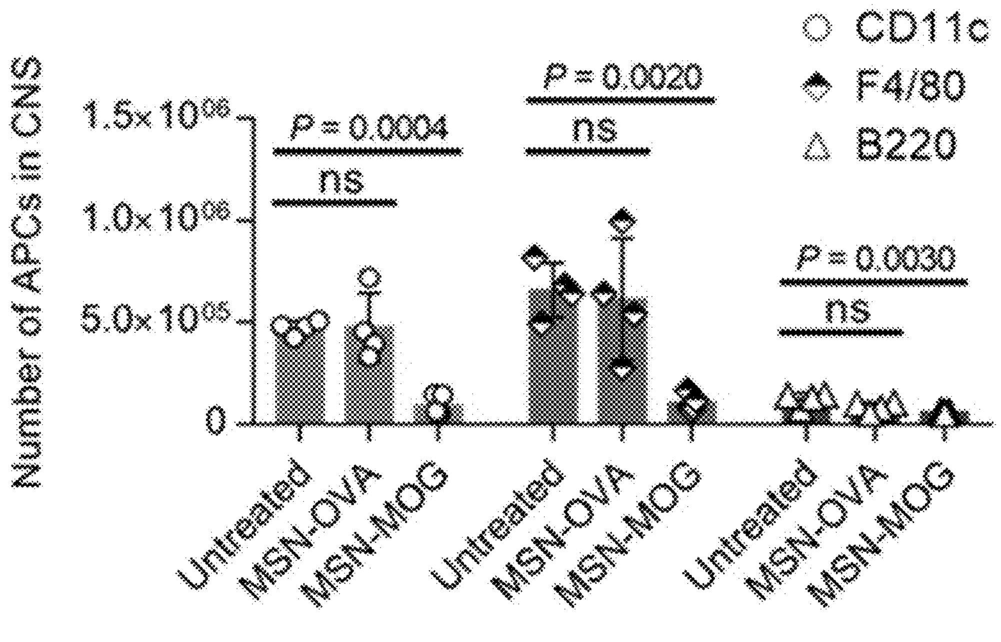
Figure 3O:
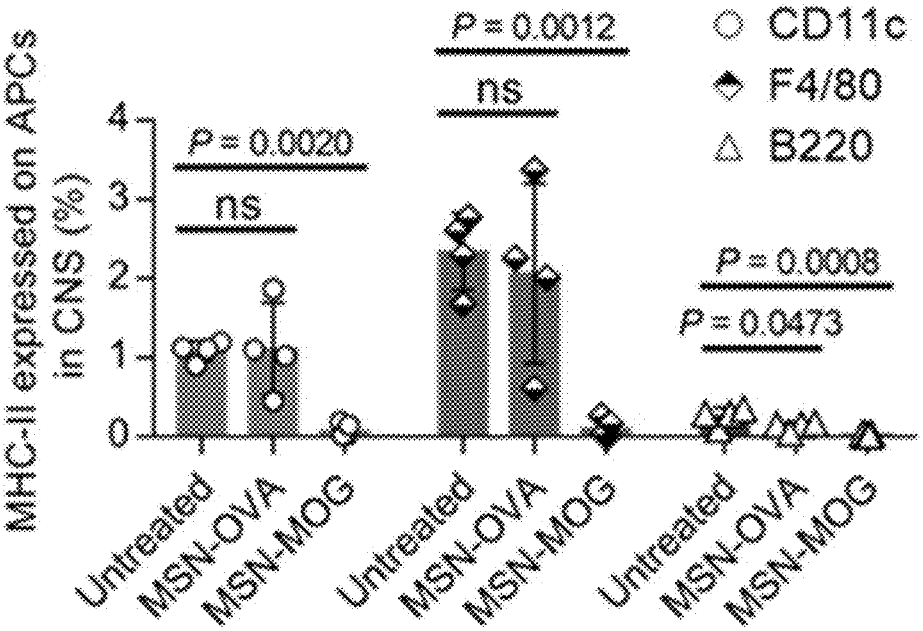
Figure 3P:
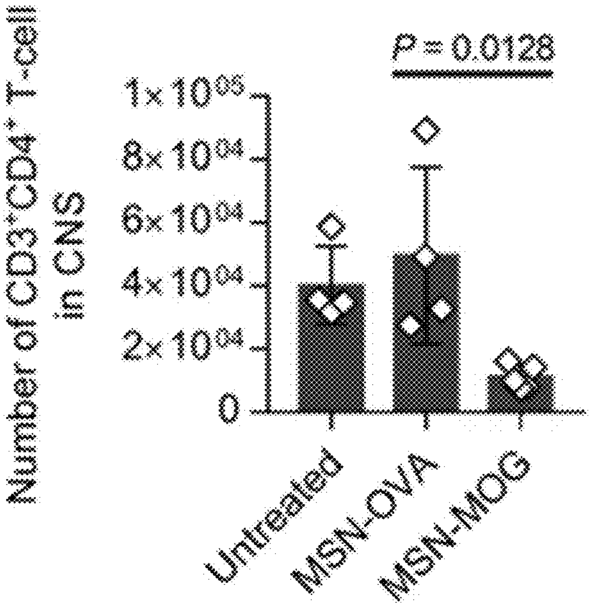
Figure 12A:
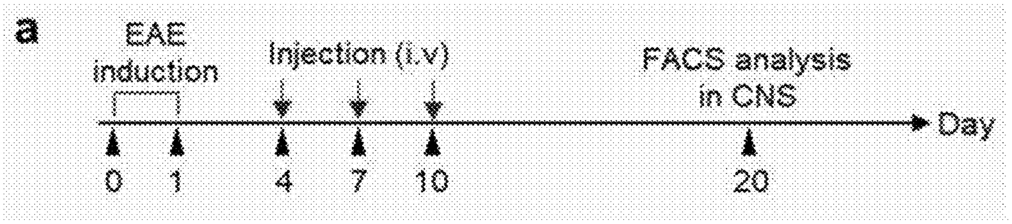
FIGS. 12*a* and 12*b* show the analysis of APCs in the CNS after administering semi-therapeutics.
Figure 12B:
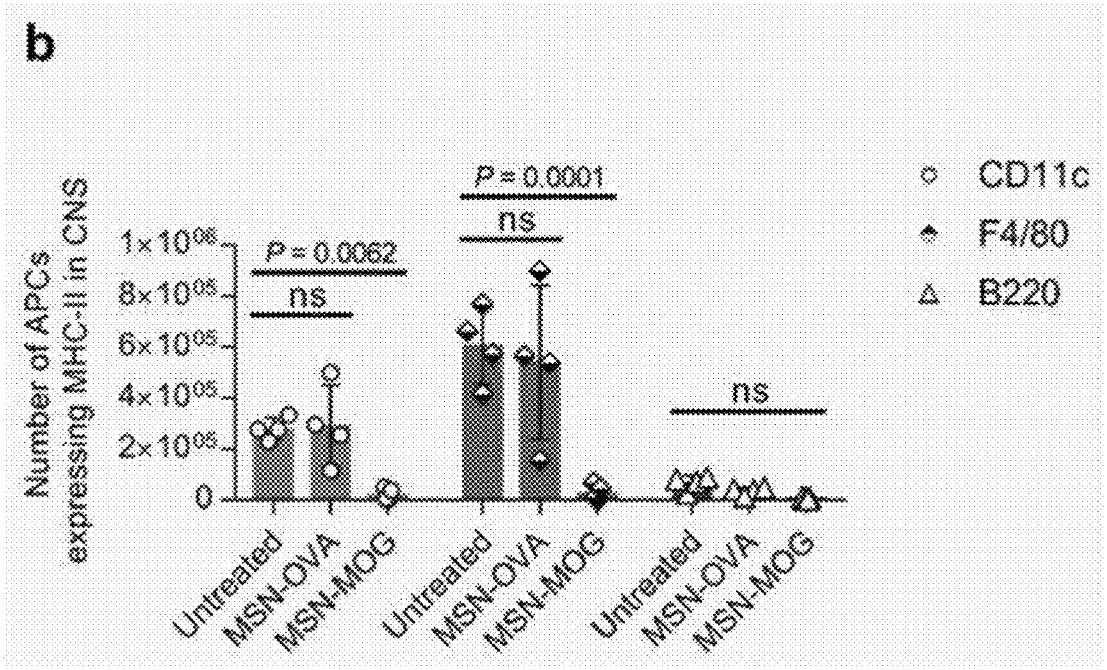
Figure 13A:
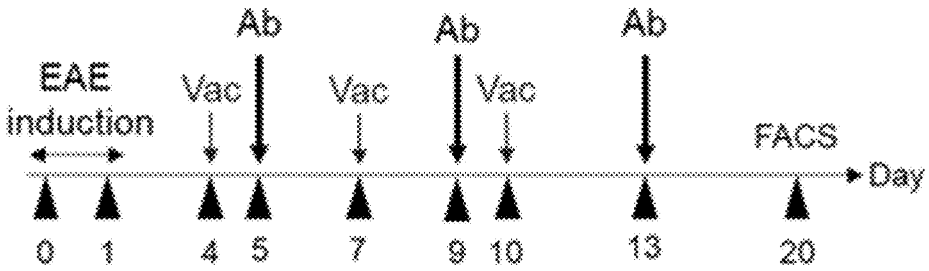
FIGS. 13*a*, 13*b*, 13*c*, and 13*d* show the analysis of immune tolerance when Treg are depleted.
Figure 13B:
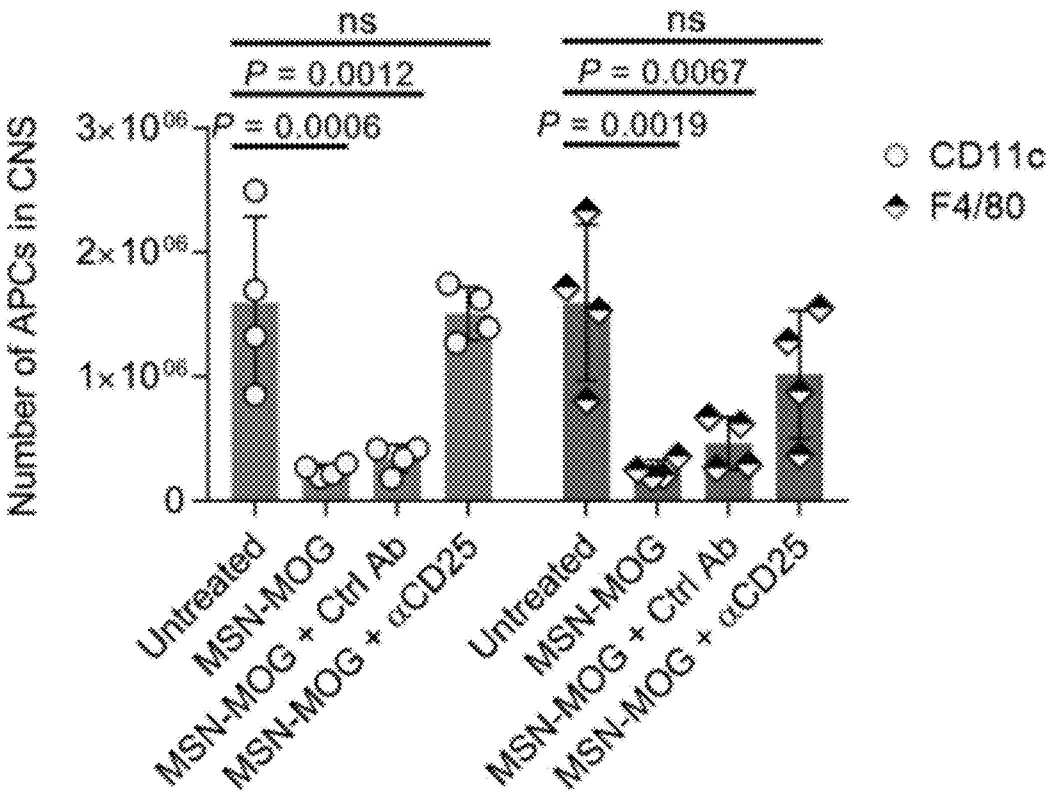
Figure 13C:
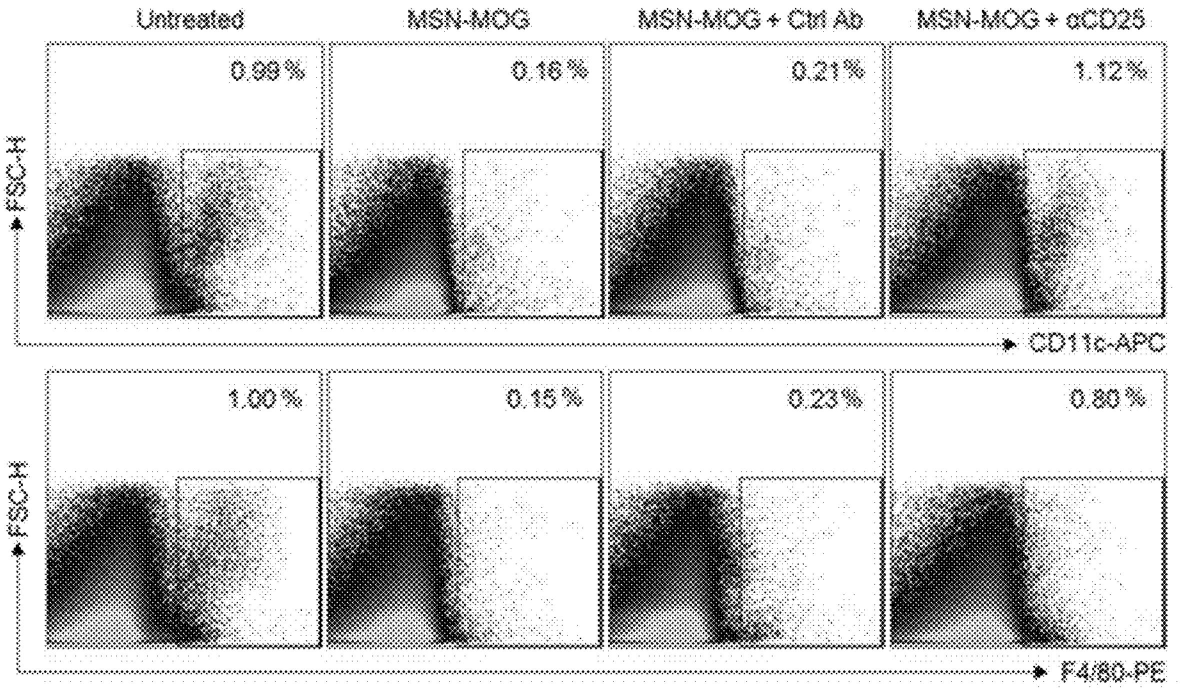
Figure 13D:
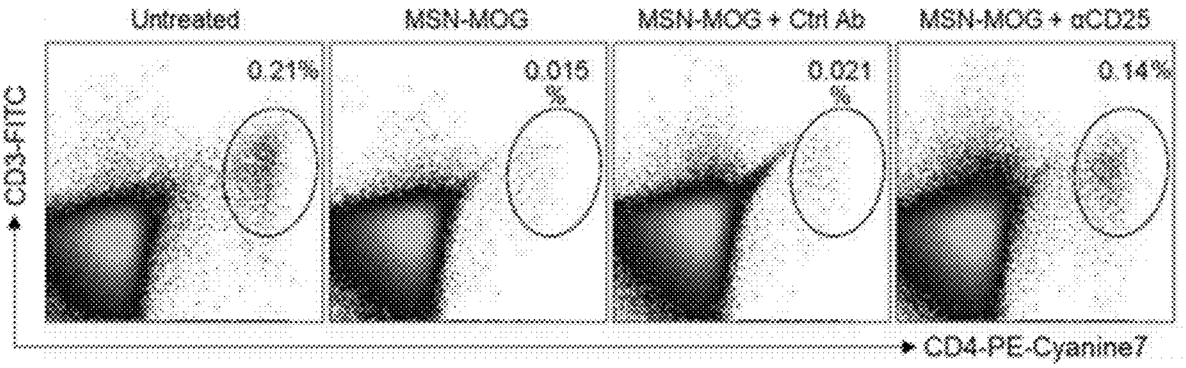

To assess immune tolerance at the disease site, the present inventors characterized the disease-associated immune cells in the CNS of EAE-induced mice intravenously injected with MSN-MOG, MSN-OVA, or left untreated. Frequencies (FIG. 3*l* and FIG. 3*m*) and numbers (FIG. 3*n*) of CNS-infiltrating APCs decreased in the MSN-MOG-treated group. The percentage (FIG. 3*o*) and the number (FIG. 12) of $CD11c^+MHC\text{-}II^+$, $F4/80^+MHC\text{-}II^+$, and $B220^+MHC\text{-}II^+$ cells in the CNS decreased in MSN-MOG-injected mice. $CD11c^+$ DCs expressing MHC-II could reactivate primed T cells and initiate EAE as DCs within inflamed CNS encounter myelin epitopes and present them to the infiltrated T cells. The resulting self-reactive T cells contribute to epitope spreading in the CNS. A decrease in the frequency and number of APCs in the CNS after MSN-MOG treatment might reduce T-cell responses in the CNS as there would be less antigen processing by APCs. Since the induced Tregs in secondary lymphoid organs (FIG. 3*e*, FIG. 3*f* and FIG. 3*g*) suppress a generation of autoreactive T cells, the number of autoreactive T cells migrating into the CNS may be decreased. Consistently, $CD4^+$ T-cell infiltration in the CNS was significantly inhibited in the MSN-MOG group (FIG. 3*p*).

Figure 3Q:
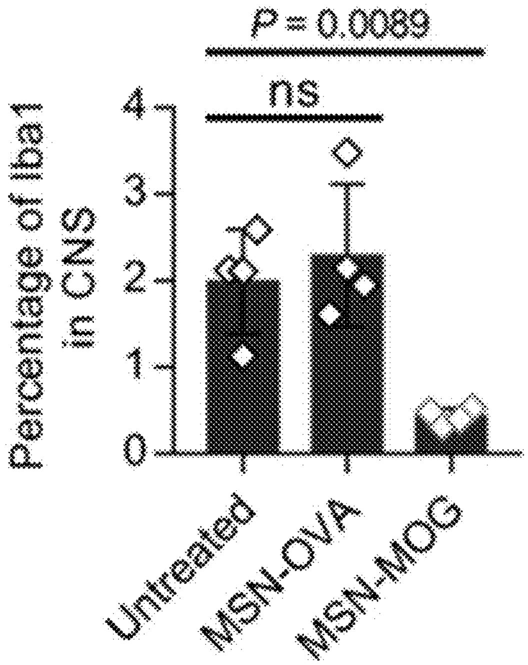
Figure 3R:
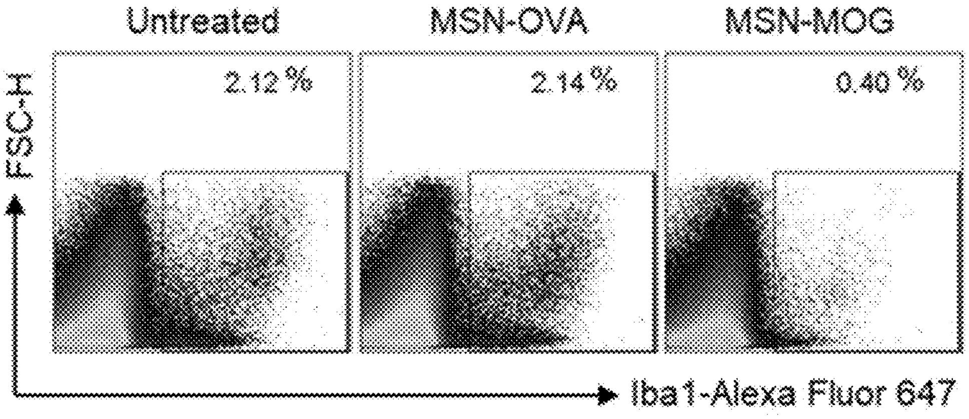

Moreover, the expression of ionized calcium-binding adapter molecule 1 (lba1), a marker of macrophage and microglia, in the cells retrieved from CNS was also notably suppressed by MSN-MOG vaccination (FIG. 3*q* and FIG. 14), presenting that the MSN-MOG vaccination could suppress the pathological cellular responses of multiple sclerosis.

Figure 3S:
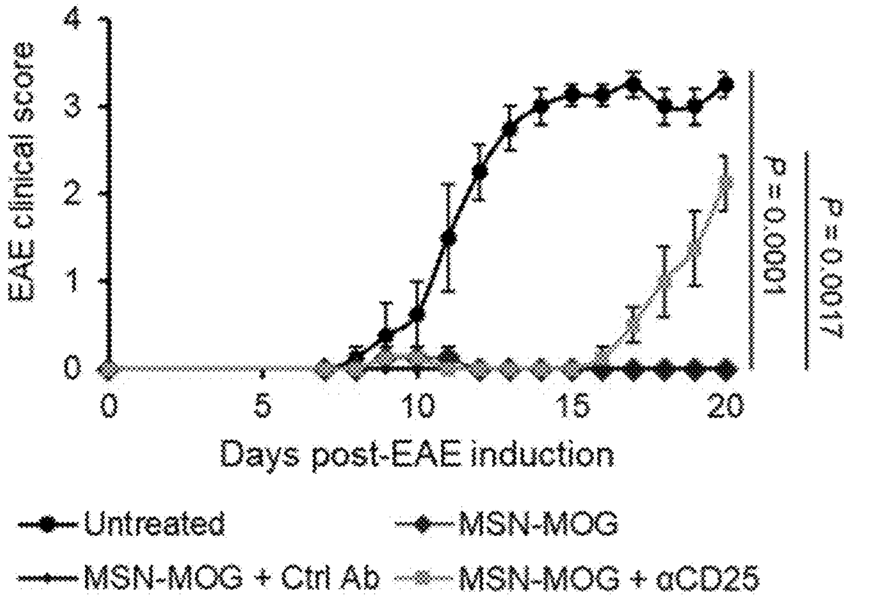
Figure 3T:
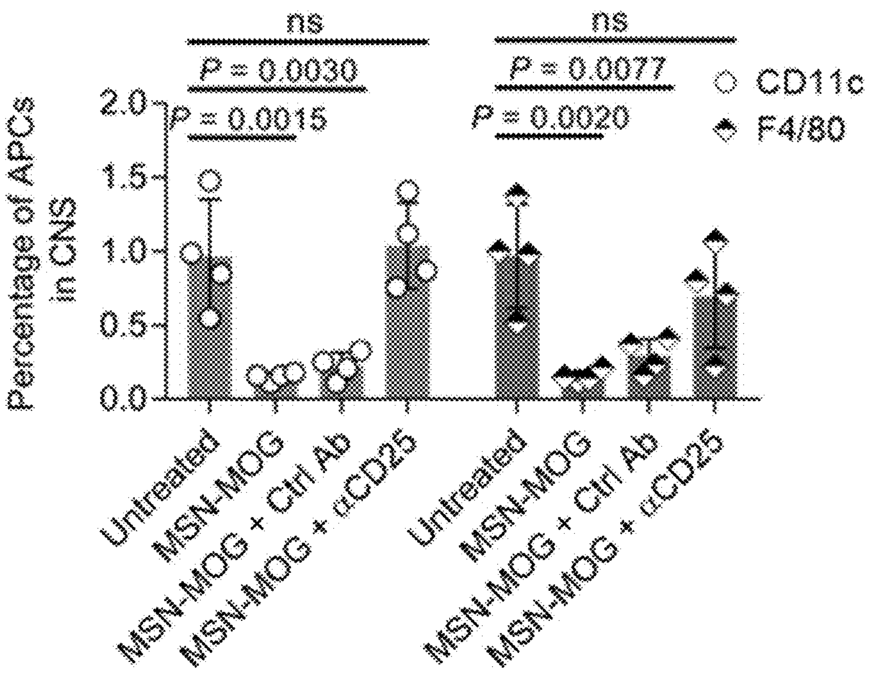
Figure 3U:
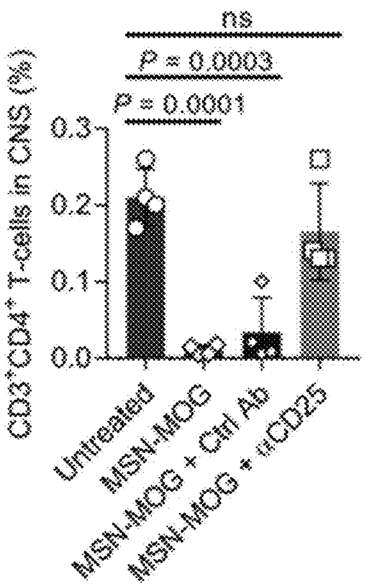

As the present inventors have observed the increase of Tregs after vaccination in EAE mice (FIG. 3*e*-3*g*), the present inventors further investigated whether the depletion of Tregs via anti-Treg antibody administration over the vaccination process would inhibit the therapeutic efficacy of MSN-MOG vaccine. The results showed that the depletion of Tregs in MSN-MOG-vaccinated mice diminished the therapeutic effect of MSN-MOG vaccine, and thus could not prevent EAE development (FIG. 3*s*). In addition, the cellular analysis revealed that depletion of Tregs led to the infiltration of $CD11c^+$ cells, $F4/80^+$ cells, and $CD4^+$ T cells into the CNS (FIG. 3*t*, FIG. 3*u* and FIG. 13).

Taken together, these data (FIG. 3*a*-31) demonstrate the potency of self-antigen-loaded MSNs in inducing systemic antigen-specific tolerance via Treg generation and reduction of Th1 and Th17-biased inflammatory cytokine secretion.

Figure 4A:
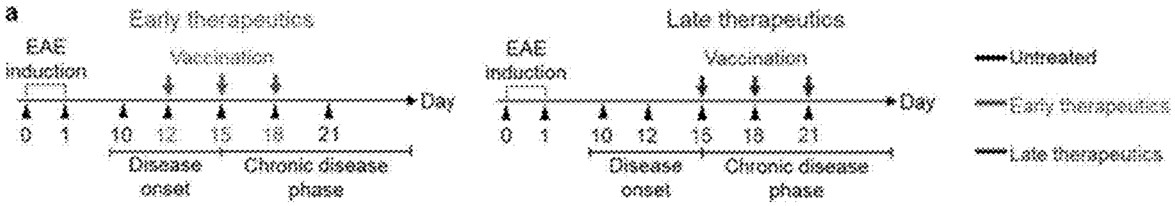
FIGS. 4*a*, 4*b*, 4*c*, 4*d*, 4*e*, 4*f*, 4*g*, and 4*h* show MSN-MOG vaccine therapeutically suppressing the developed EAE.
Figure 4B:
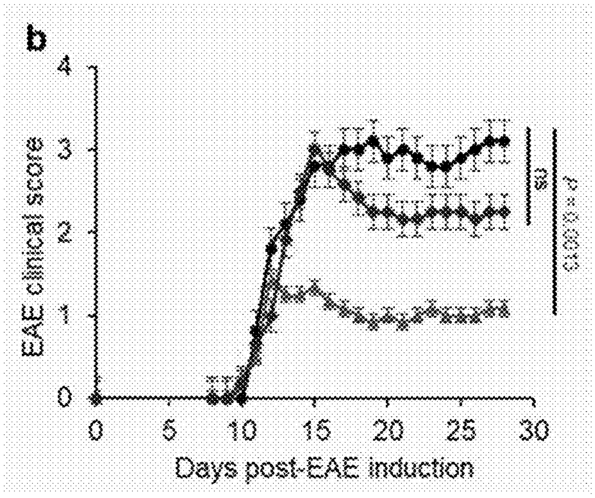
Figure 4C:
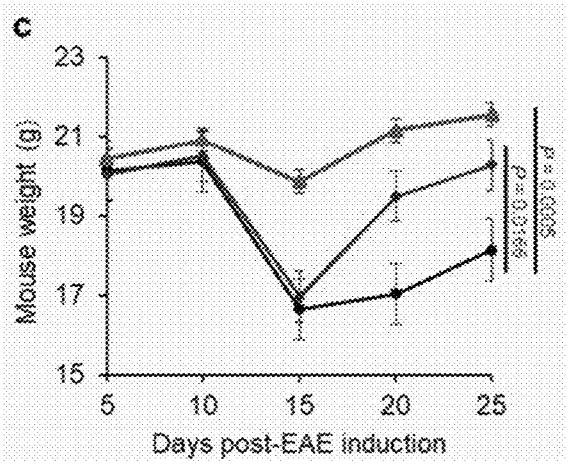
Figure 4D:
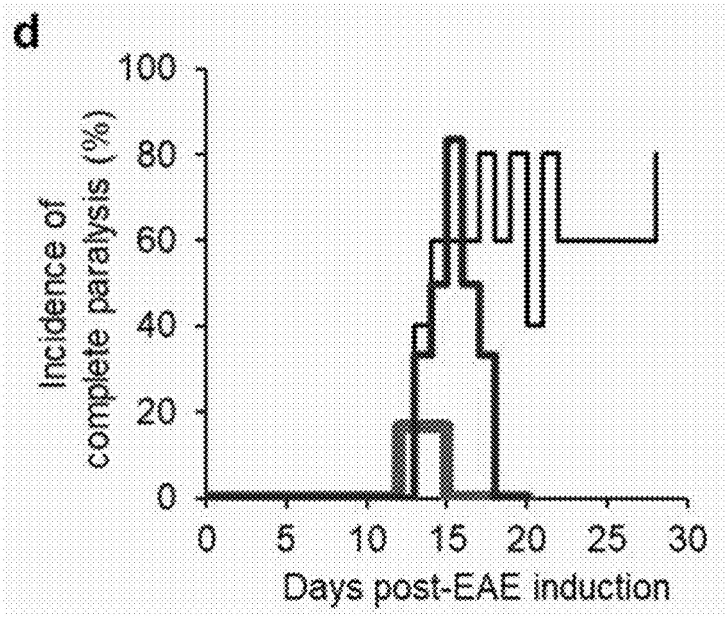
Figure 4E:
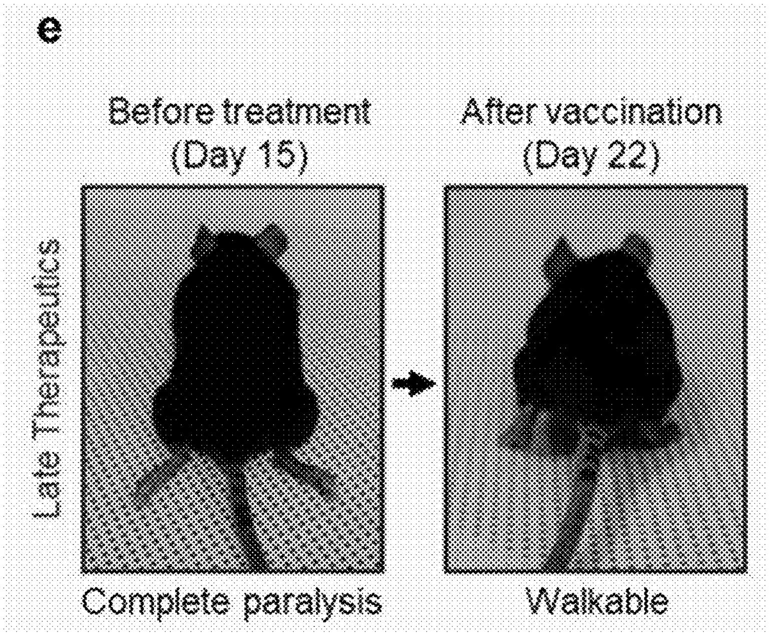

4. MSN-MOG Vaccine Reduces Disease Severity Following Therapeutic Intervention at the Late Stage of the Disease Although the present inventors have shown that MSN-MOG could suppress the development of EAE in semi-therapeutic study (FIG. 2*f* and FIG. 2*g*), MS in human is initiated before clinical symptoms appear, leading to the high demand for therapeutics to treat MS after the clinical diagnosis. Next, the present inventors investigated whether MSN-MOG suppressed EAE during the onset and chronic phases. EAE-induced mice received three intravenous MSNMOG injections at 3 days intervals, starting on day 12 (the point of intermediate disease severity, early therapeutics) or day 15 (the peak of disease severity, late therapeutics) (FIG. 4*a*). The results showed that for both treatment regimens, progression of clinical episodes was strongly hampered immediately after the first injection (FIG. 4*b*), leading to body weight recovery of the mice (FIG. 4*c*). In both treated groups, complete paralysis disappeared three days after the first injection (FIG. 4*d*). For example, mice completely paralyzed on day 15 after EAE induction were able to walk on day 22 after vaccinations on days 15, 18, and 21 (FIG. 4*e*). These data reveal that MSN-MOG mediated functional recovery from neuroinflammation in EAE.

Figure 4F:
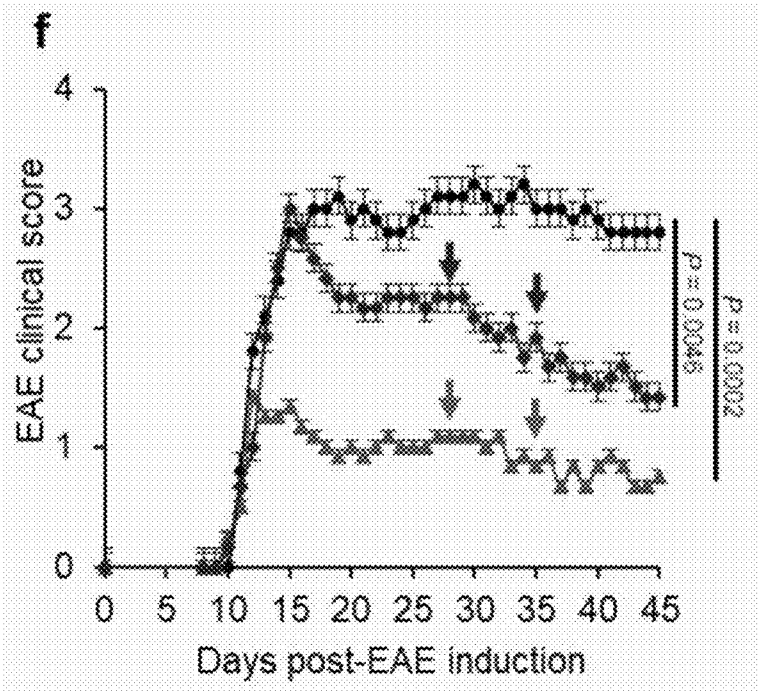
Figure 4G:
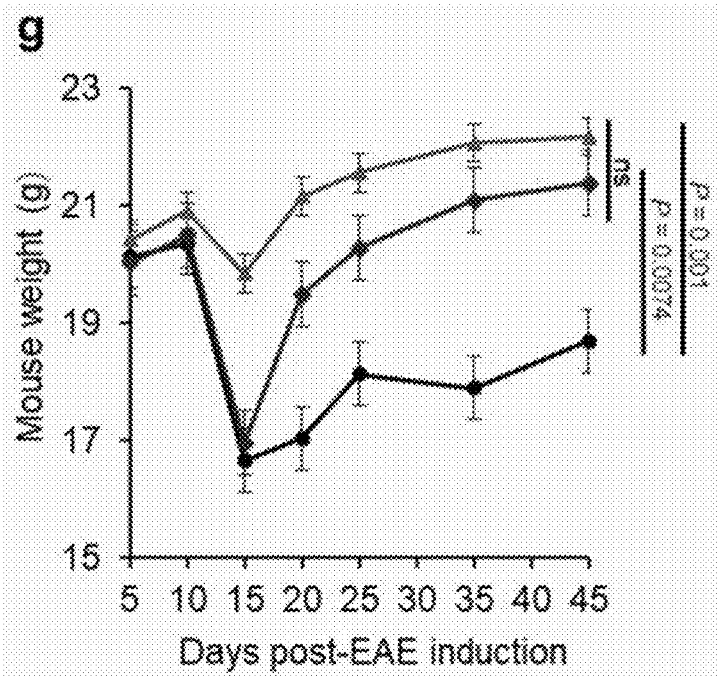
Figure 4H:
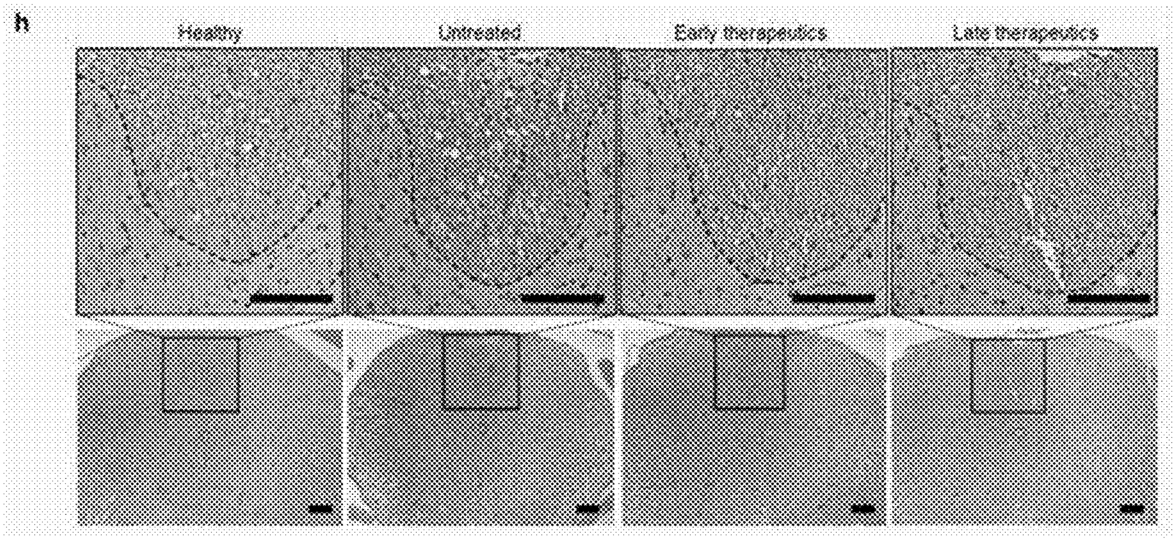

As the clinical scores remained stable after three shots in both early and late therapeutic studies (FIG. 4*b*), the present inventors examined whether motor impairment could be further ameliorated by providing additional vaccinations on days 28 and 35, to all mice except the untreated group. EAE severity in the early and late therapeutic groups reduced strongly after two more shots (FIG. 4*f*). Especially, in late therapeutics group, the clinical score became significantly lower than in the untreated group, indicating the significance of therapeutic efficacy of nanovaccine to treat the late chronic stage of EAE. At the end of the study, the body weights of mice had recovered completely, and there were no differences between the early and late therapeutic groups (FIG. 4*g*). Representative hematoxylin and eosin (H&E)-stained histological images revealed fewer inflammatory cells in the ventral area of the white matter of MSN-MOG-treated mice in both early and late therapeutics groups than that of the untreated mice, indicating that the vaccination induced an improvement of neuro-immune homeostasis comparable to the healthy mice (naive mice) (FIG. 4*h*).

Figure 5A:
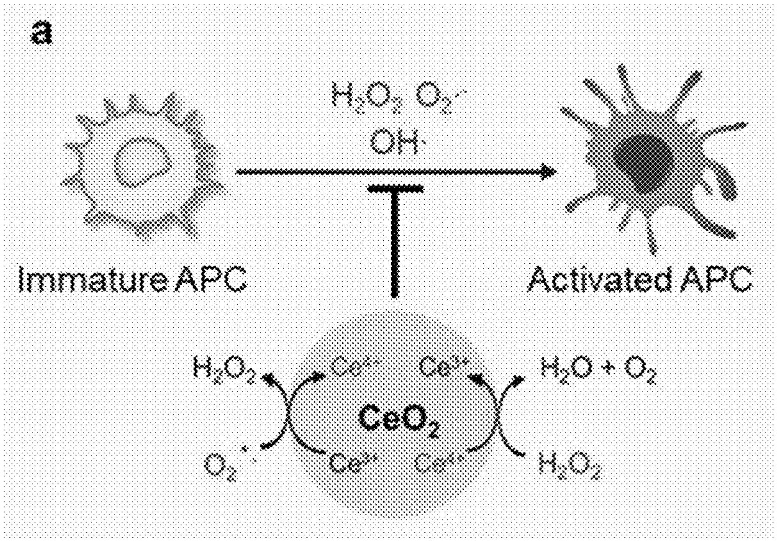
FIGS. 5*a*, 5*b*, 5*c*, 5*d*, 5*e*, 5*f*, 5*g*, 5*h*, 5*i*, 5*j*, 5*k*, 5*l*, 5*m*, 5*n*, 5*o* and 5*p* show ROS-scavenging CeNPs inducing tolerogenic APCs.
Figure 5B:
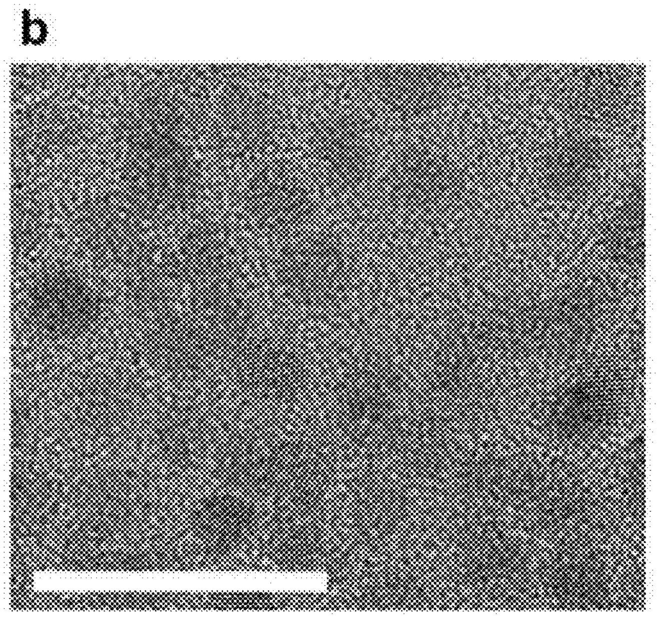
Figure 5C:
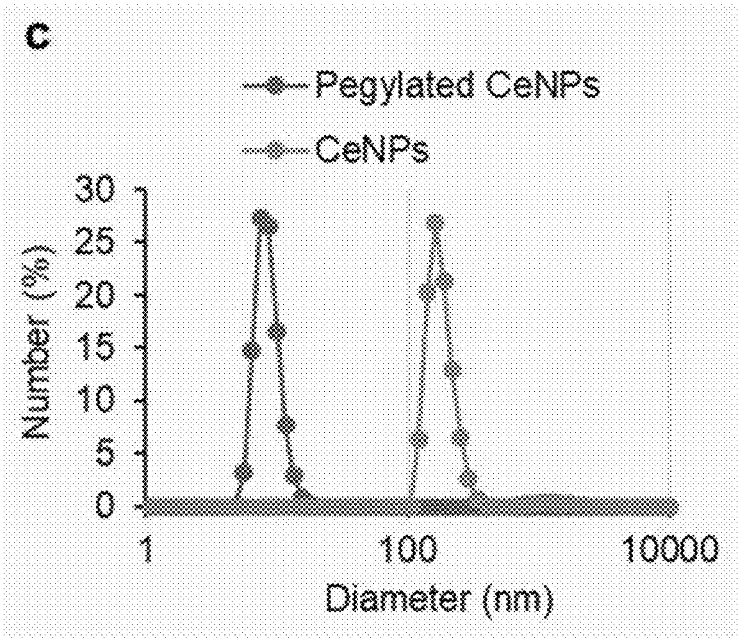
Figure 5D:
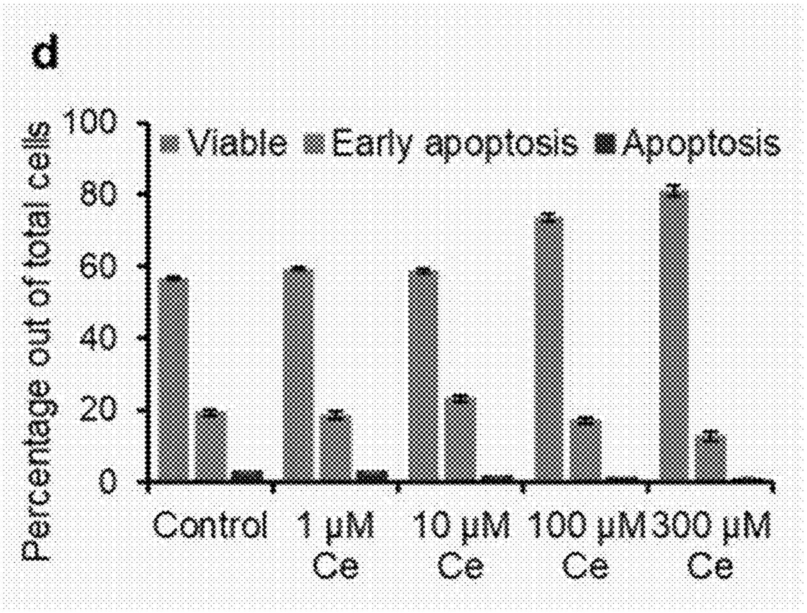
Figure 5E:
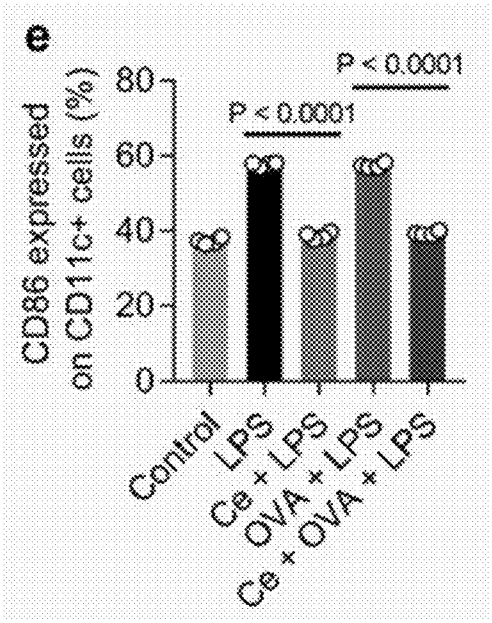
Figure 5F:
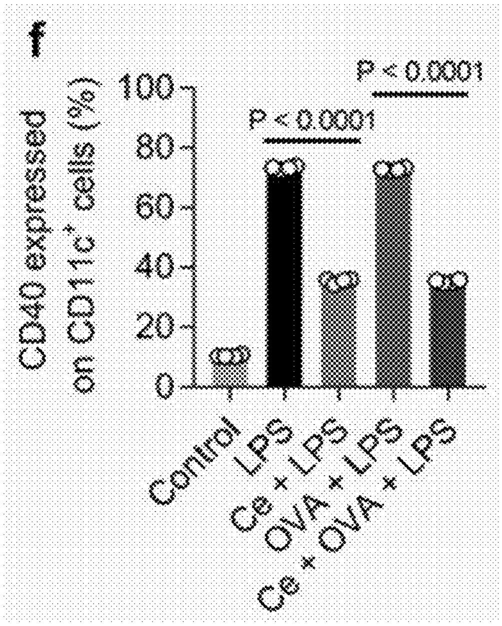
Figure 5G:
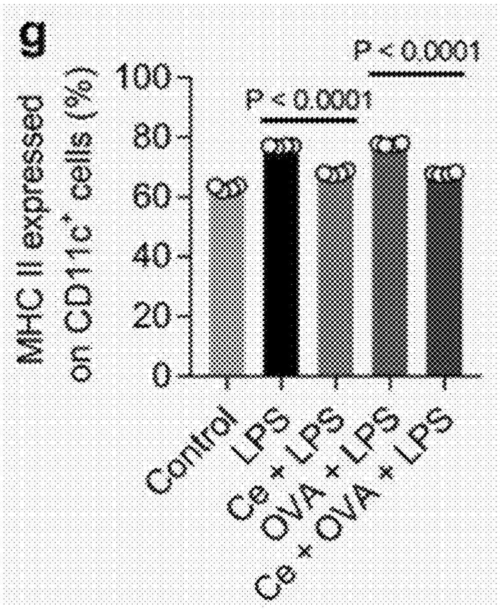
Figure 14A:
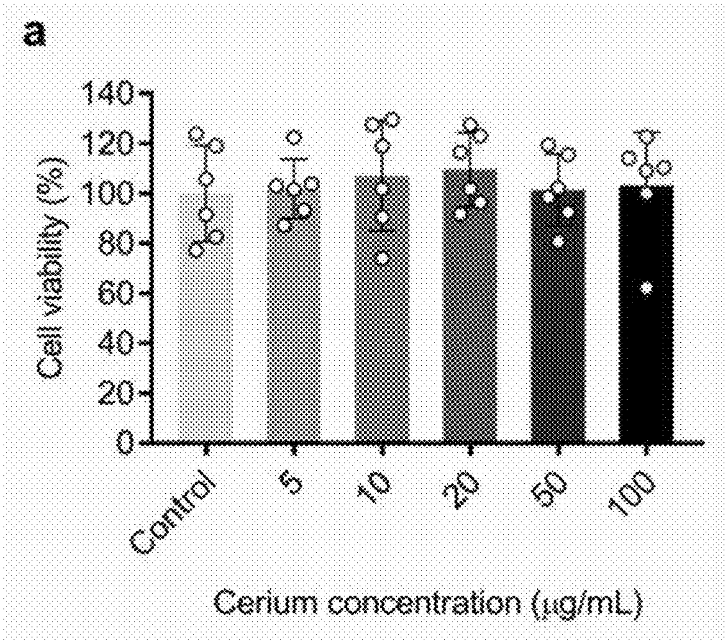
FIGS. 14*a* and 14*b* shows the results of characterization of cerium oxide nanoparticles.
Figure 14B:
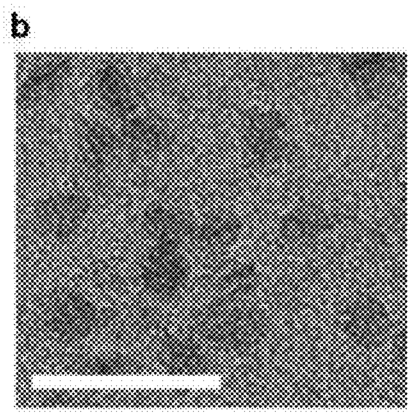

5. ROS-Scavenging CeNPs Suppresses Activation of APCs and Induces Tolerogenic APCs Since oxidative stress derived from high intracellular ROS is known to activate APC, especially in MS, the present inventors hypothesized that scavenging intracellular ROS in APCs would further suppress their activation and potentially enhance the tolerogenic phenotype of APCs (FIG. 5*a*). The ceria nanoparticles (CeNPs) were recently engineered for the treatment of ROS-associated diseases, due to their ROS-scavenging catalytic properties that mimic catalase and superoxide dismutase; however, the immunological impact of these nanoparticles has not been investigated intensively. Water-dispersible, positively charged CeNPs (4 nm) were synthesized according to our previous reports (Jeong, H. G. et al. Ceria Nanoparticles Fabricated with 6-Aminohexanoic Acid that Overcome Systemic Inflammatory Response Syndrome. Adv. Healthc. Mater. 8, 1-10 (2019)) (FIG. 5*b* and FIG. 14). To improve the dispersion of CeNPs in the cell culture medium, polyethylene glycol (PEG) was coated on the CeNPs (FIG. 5*c* and FIG. 14). The resulting CeNPs were highly biocompatible (FIG. 5*d*) and were directly used to examine the capacity to suppress the activation of bone marrow-derived dendritic cells (BMDCs). BMDCs were cultured with CeNPs and treated with lipopolysaccharides (LPS), a TLR4 agonist known to induce excessive intracellular ROS production and enhance activation of APCs, resulting in a substantially decreased expression levels of costimulatory molecules (CD86 and CD40) and MHC-II (FIG. 5*e*, FIG. 5*f* and FIG. 5*g*). These data demonstrate the ROS-scavenging CeNPs could prevent activation of DCs and maintain the tolerogenic phenotype of DCs even under the presence of immune-activating TLR4 agonist.

Figure 5H:
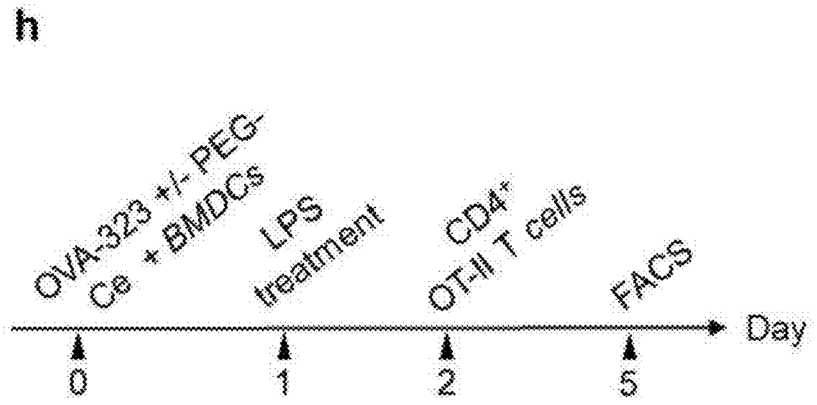
Figure 5I:
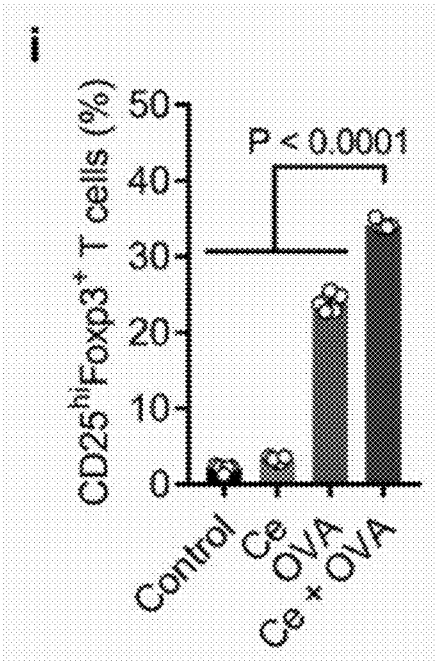
Figure 5J:
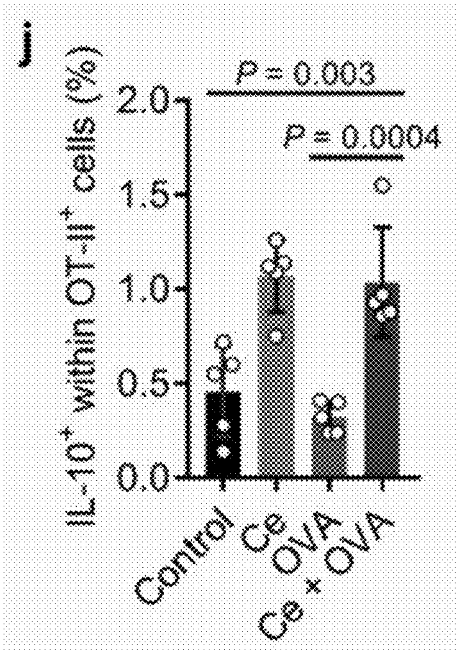
Figure 5K:
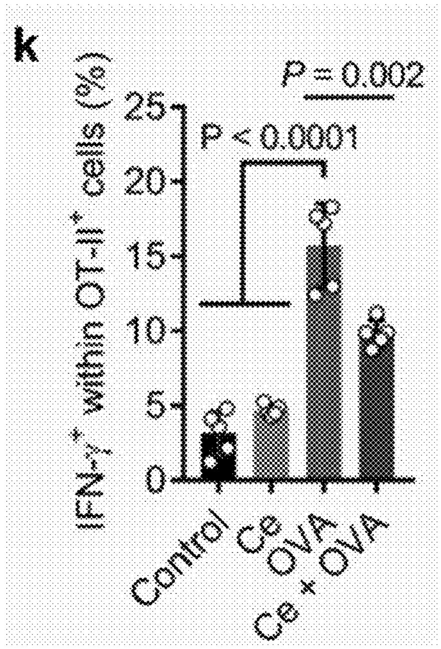
Figure 5L:
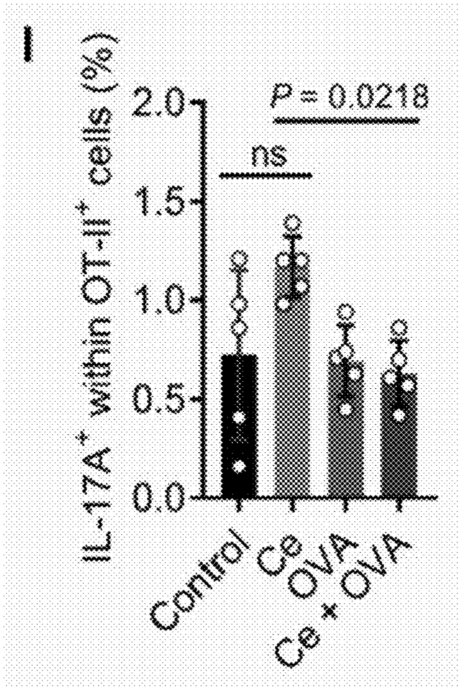
Figure 5M:
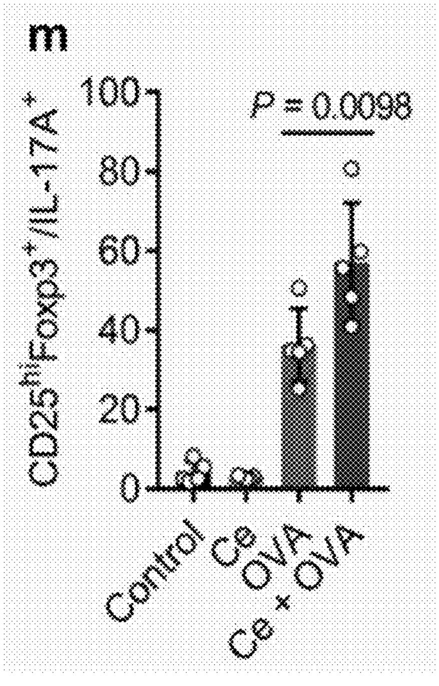
Figure 5N:
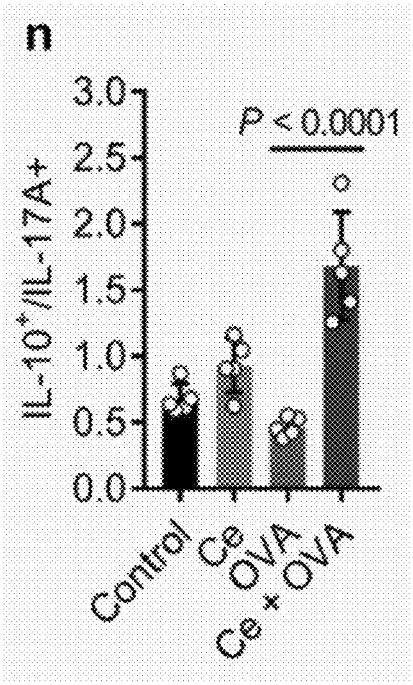
Figure 5O:
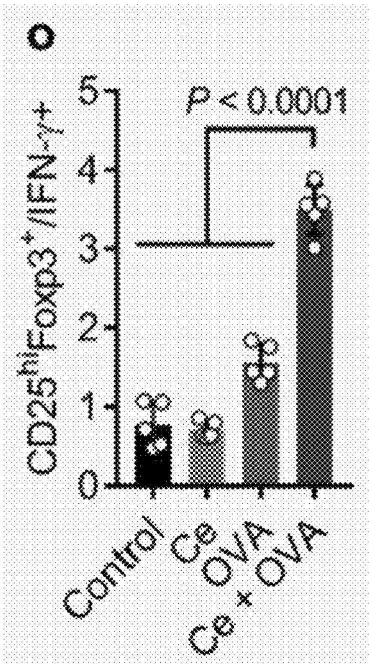
Figure 5P:
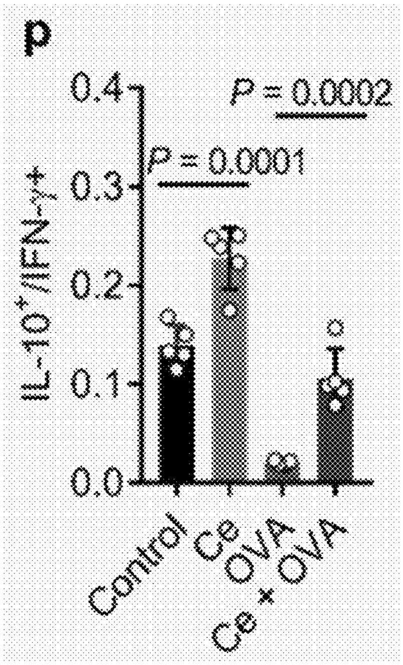
Figure 15:
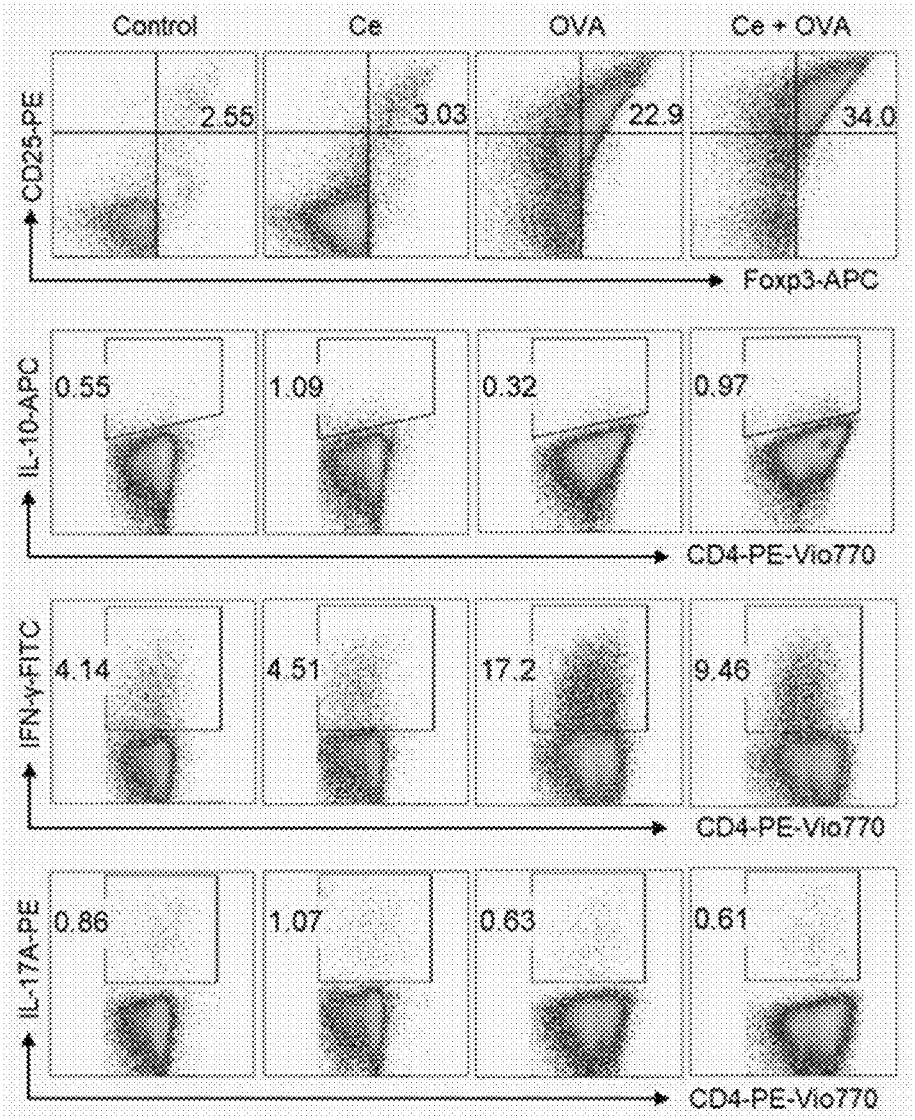
FIG. 15 shows CeNPs inducing Tregs in vitro. BMDCs were incubated with pegylated CeNPs (Ce, 50 μM cerium), $OVA_{323-339}$ (OVA, 1 μg/mL), pegylated CeNPs plus $OVA_{323}$-339 (Ce+OVA), or left untreated for 24 h; following by LPS treatment (1 μg/mL) for the next 24 h before being co-cultured with OT-II $CD4^+$ T-cells for 72 h.

The present inventors next evaluated whether the $OVA_{323-339}$ peptide-experienced semi-mature DCs induced by CeNP could trigger the $CD4^+$ T-cell differentiation to Tregs by co-culturing these DCs with $CD4^+$ T cells retrieved from OT-II transgenic mice (FIG. 5*h*). The $CD4^+$ T cells in OT-II mice have T-cell receptors that specifically recognize $OVA_{323-339}$ peptide. A significantly higher percentage of $CD25^+Foxp3^+$ Tregs appeared in the CeNP+OVA-treated group than the others (FIG. 5*i* and FIG. 15). Interestingly, the elevated population of IL-10 secreting $CD4^+$ T cells, known as type 1 regulatory T cells (Tr1) that inhibit DC maturation and establish T-cell tolerance, was observed in CeNP-treated group and the CeNP+OVA-treated group (FIG. 5*j* and FIG. 15). In contrast, the IFN-γ secreting $CD4^+$ T cells (activated Th1 cells) was significantly suppressed in CeNP+OVA-treated group compared to OVA-treated one (FIG. 5*k* and FIG. 15). Although there was no difference in IL-17A secretion within $CD4^+$ T cells between the OVA-treated group and the CeNP+OVA-treated group (FIG. 5*l* and FIG. 15), the ratios of $CD25^+Foxp3/IL\text{-}17A^+$ and $IL\text{-}10/IL\text{-}17A^+$ in CeNP+OVA-treated group were highest among groups (FIG. 5*m* and FIG. 5*n*). In addition, the bias of naive $CD4^+$ T cells into Tregs and Tr1 rather than Th1 by CeNPs was demonstrated by the greater ratios of $CD25^+Foxp3^+/IFN\text{-}\gamma^+$ and $IL\text{-}10^+/IFN\text{-}\gamma^+$ in the CeNP+OVA-treated group, respectively (FIG. 5*o* and FIG. 5*p*). Taken together, these data show that CeNPs could induce tolerogenic DCs which can skew naive $CD4^+$ T cells toward Tregs and Tr1 in vitro, representing that CeNPs could be used as an immunosuppressive agent to enhance immune tolerance.

Figure 6A:
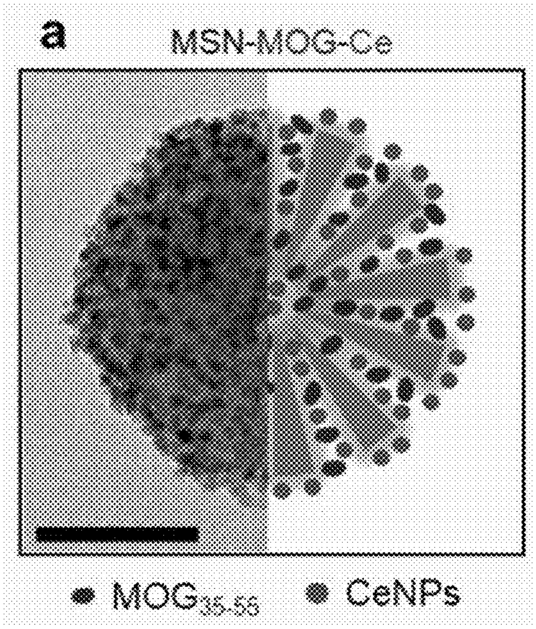
FIGS. 6*a*, 6*b*, 6*c*, 6*d*, 6*e*, 6*f*, 6*g*, 6*h*, 6*i*, 6*j*, 6*k*, 6*l*, 6*m*, 6*n* and 6*o* show CeNPs-decorated MSN-MOG enhancing efficacy of the therapeutic vaccine against EAE at chronic phase.
Figure 6B:
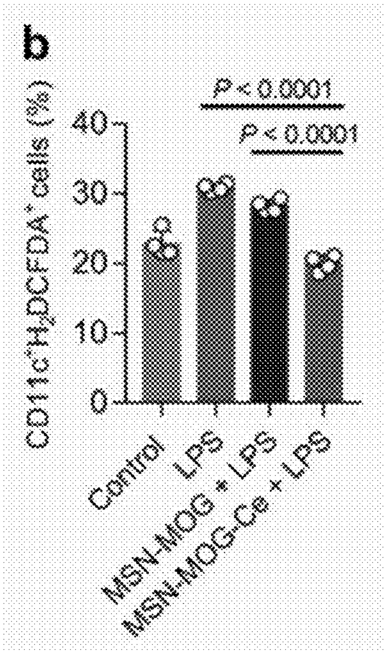
Figure 6C:
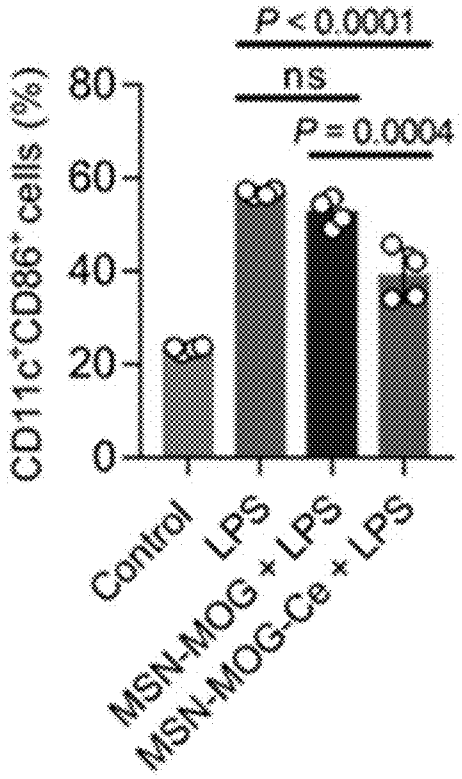
Figure 17:
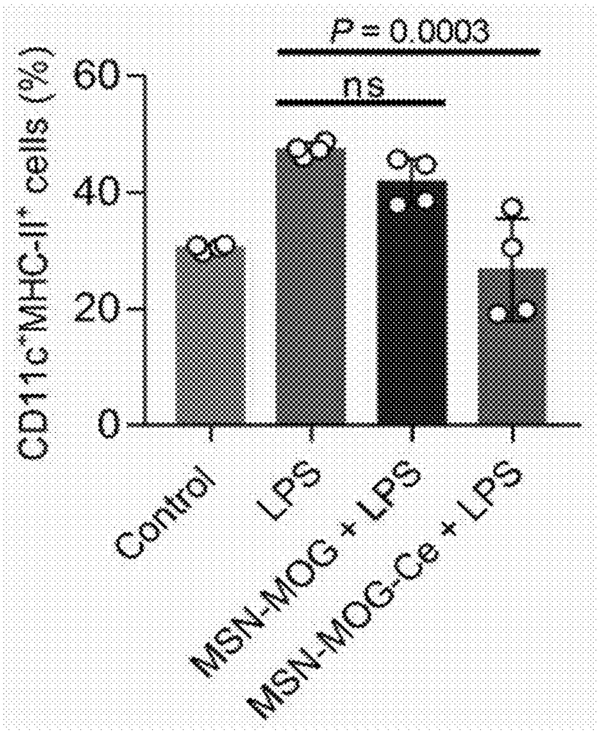
FIG. 17 shows in vitro BMDCs suppression. BMDCs were treated with MSN-MOG, MSN-MOG-Ce, or left untreated for 24 h, followed by stimulation with 100 ng/mL LPS for the next 12 h; n=4 biologically independent samples. Figure shows the percentage of $CD11c^+$ BMDCs expressing MHC-II. The data are represented as mean±SD and were analyzed by one-way ANOVA with Tukey's multiple comparisons test, ns=not significant.

6. ROS-Scavenging MSN-MOG Vaccine Enhances the Therapeutic Efficacy in the Late Chronic Phase of EAE To enhance the therapeutic efficacy of autoimmune disease nanovaccine, CeNPs were additionally attached on MSN-MOG via electrostatic interactions between the negatively charged MSN-MOG and positively charged CeNPs (FIG. 16), resulting in the ROS-scavenging MSN-MOG-Ce nanovaccine (FIG. 6*a*). The ability of MSN-MOG-Ce to scavenge intracellular ROS in BMDCs was examined in the presence of LPS. The level of intracellular ROS was significantly lower in MSN-MOG-Ce-treated BMDCs than in LPS- and MSNMOG-treated BMDCs (FIG. 6*b*), revealing that MSN-MOG-Ce attenuated oxidative stress in BMDCs under inflammatory conditions. Consistently, BMDCs treated with MSN-MOG-Ce expressed lower levels of CD86 and MHC-II than LPS-treated cells; MSN-MOG had no impact on the BMDC activation markers (FIG. 6*c* and FIG. 17). MSN-MOG-Ce could prevent oxidative stress in BMDCs and maintain their semi-maturity under an inflammatory environment, representing its potential to further aid DCs in enhancing peripheral tolerance in vivo.

Figure 6D:
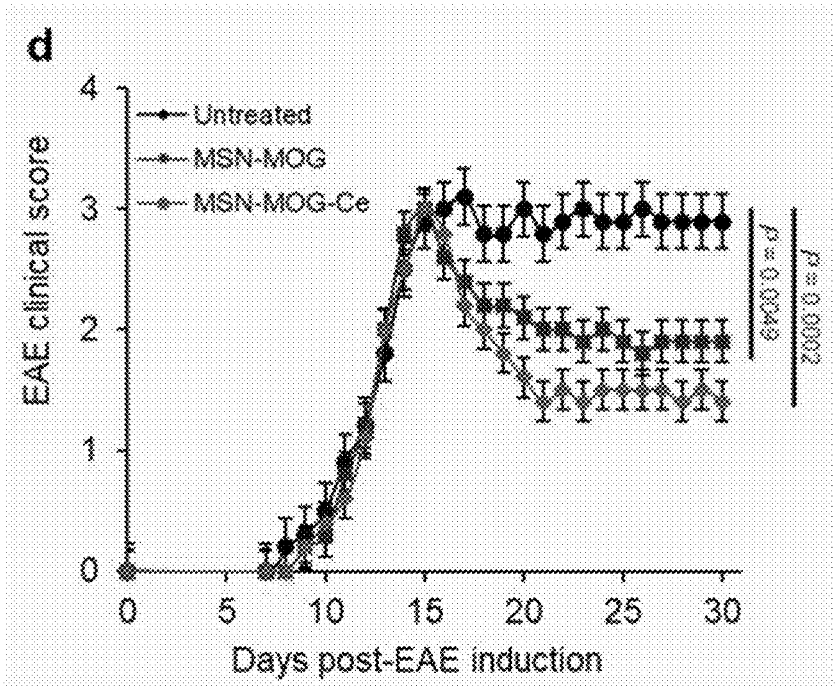
Figure 18A:
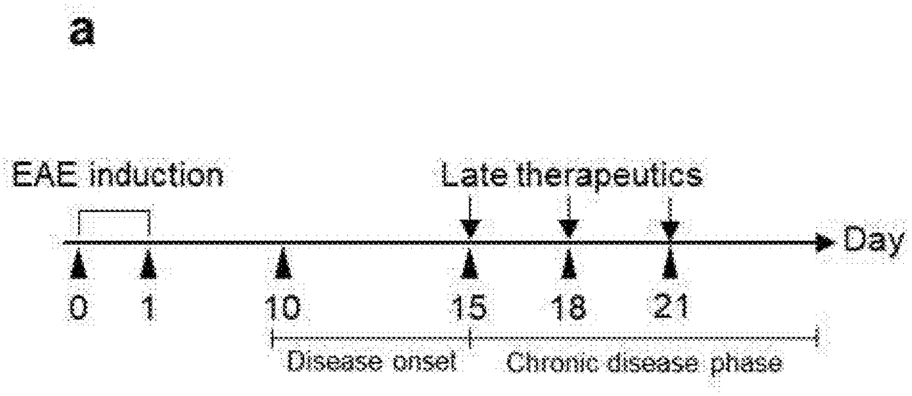
FIGS. 18*a* and 18*b* show the body weight changes during late therapeutic treatment.
Figure 18B:
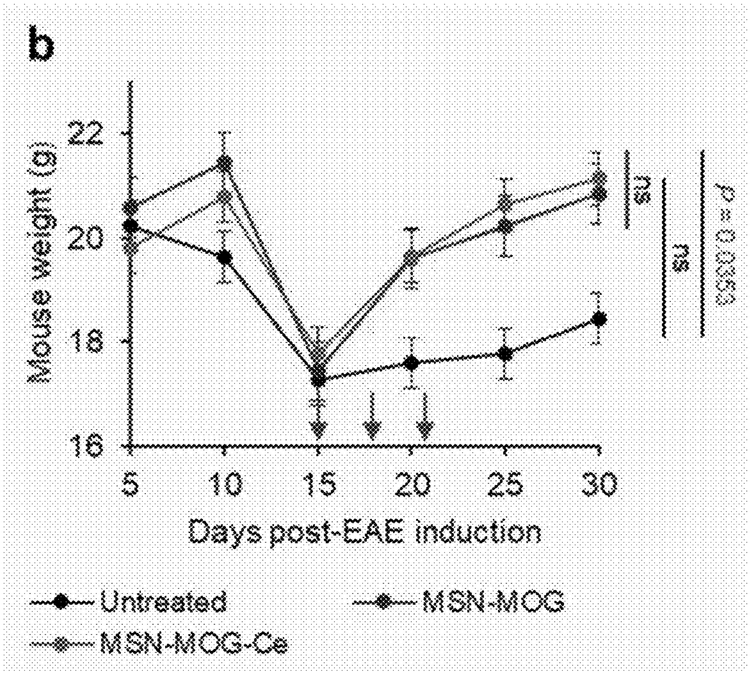
Figure 19A:
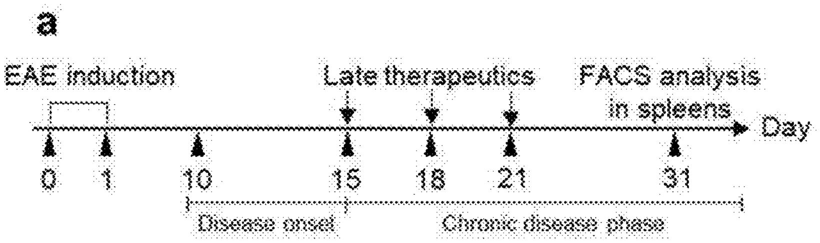
FIGS. 19*a*, 19*b*, 19*c*, 19*d*, 19*e*, 19*f* and 19*g* show the analysis of APCs in spleens after administering late therapeutics.
Figure 19B:
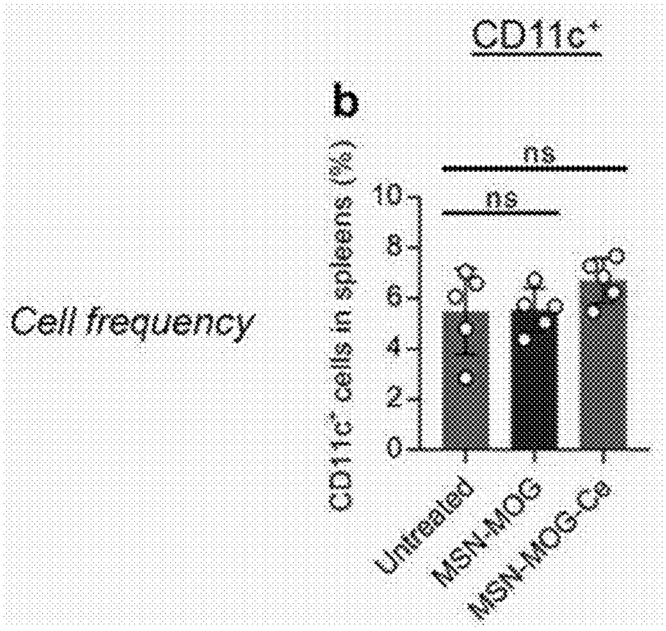
Figure 19C:
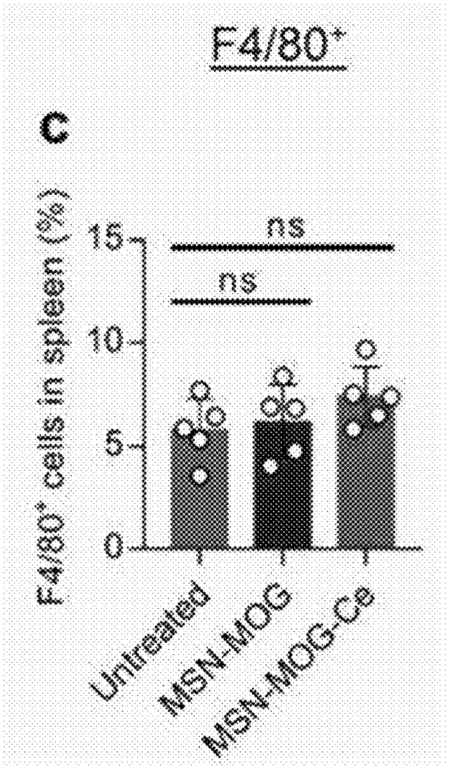
Figure 19D:
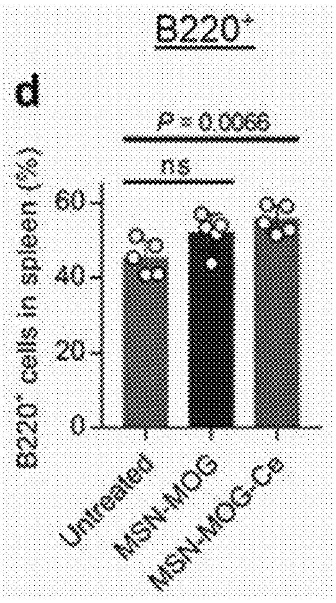
Figure 19E:
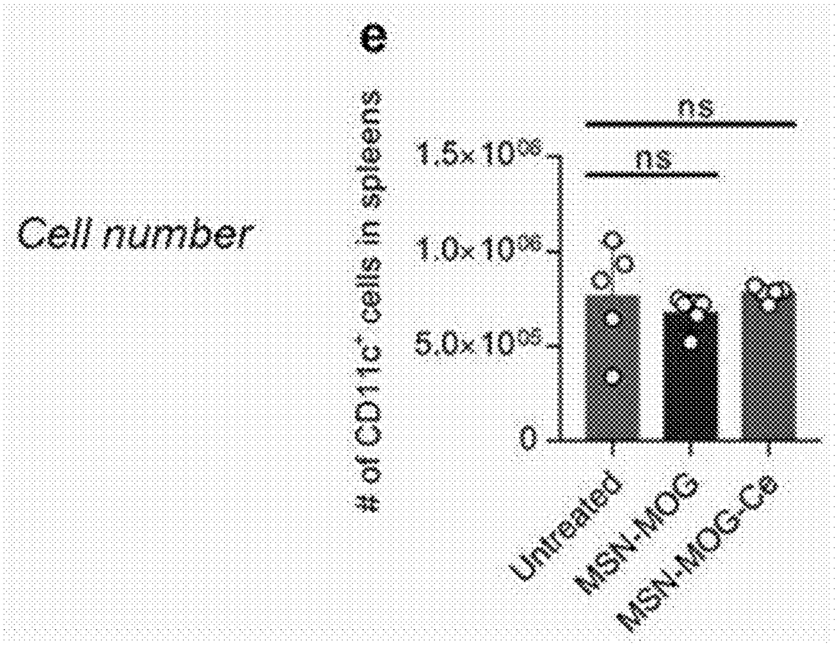
Figure 19F:
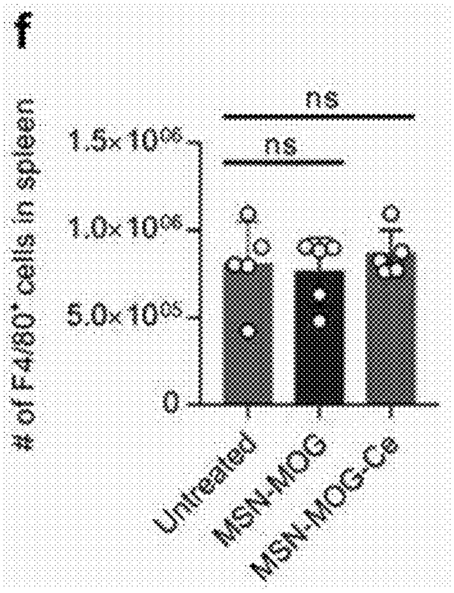
Figure 19G:
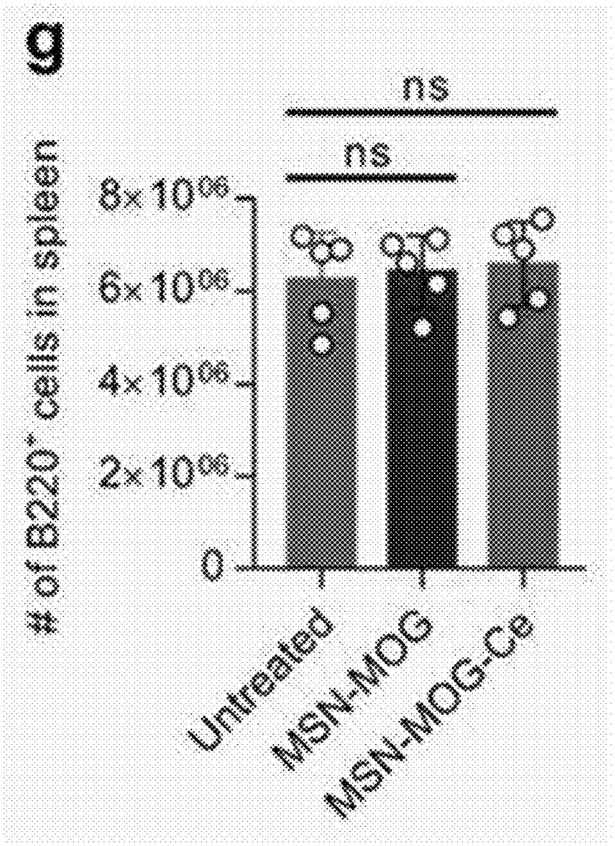
Figure 20A:
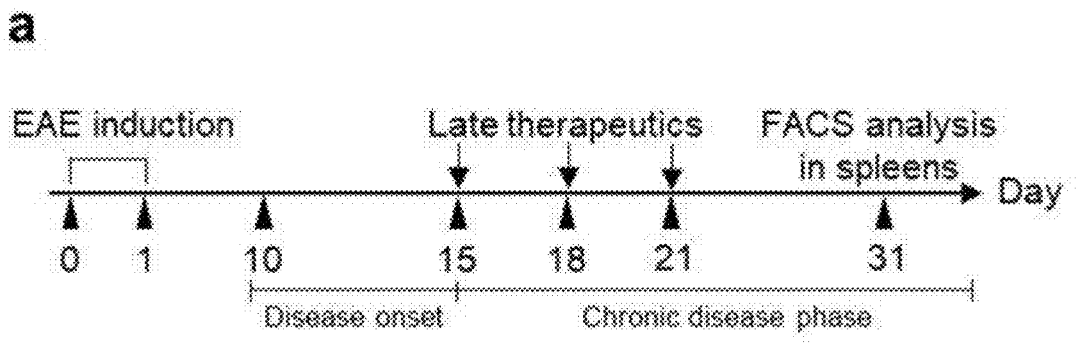
FIGS. 20*a*, 20*b*, 20*c* and 20*d* show the analysis of MHC-II expression on APCs in spleens after administering late therapeutics.
Figure 20B:
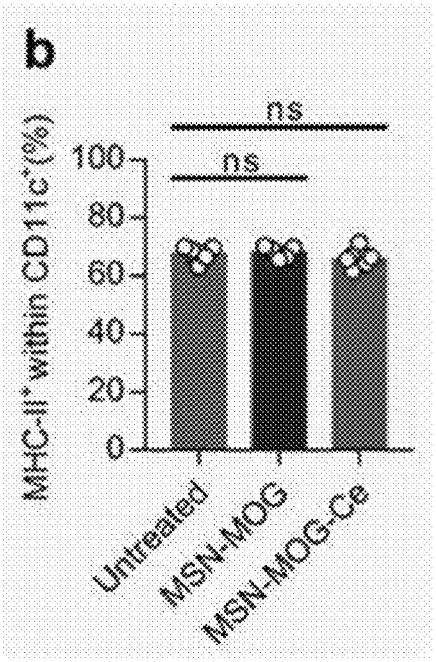
Figure 20C:
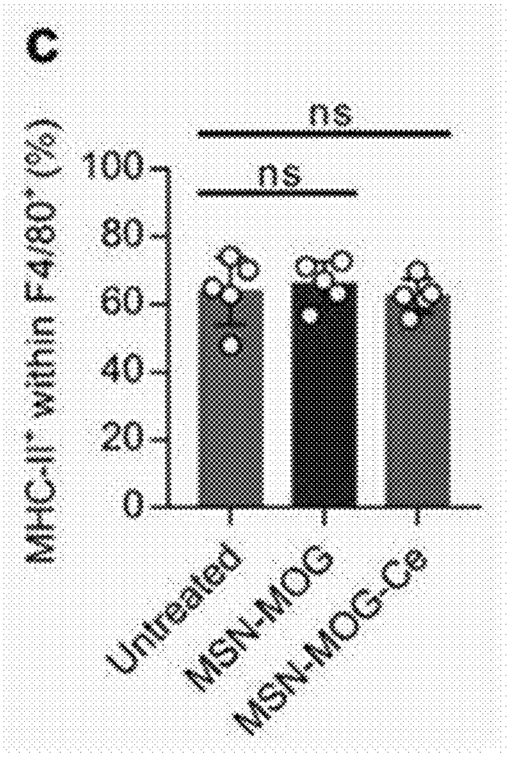
Figure 20D:
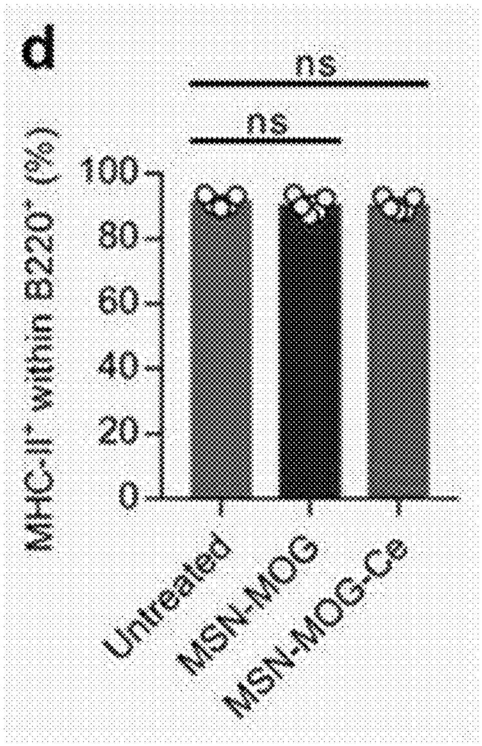

Next, to investigate the therapeutic efficacy of ROS-scavenging vaccine, EAE-induced mice in the late chronic phase were intravenously injected with MSN-MOG, MSN-MOG-Ce, or left untreated. The present inventors observed an additional reduction in the clinical score for MSN-MOG-Ce-injected EAE mice compared to that for MSN-MOG-injected EAE mice (FIG. 6*d*, see FIG. 18 for weight change). After the late therapeutic treatment (day 22), MSN-MOG-Ce-treated EAE mice could take complete coordinated strides, unlike the visibly irregular/wobble walk of MSN-MOG-treated mice.

Figure 6E:
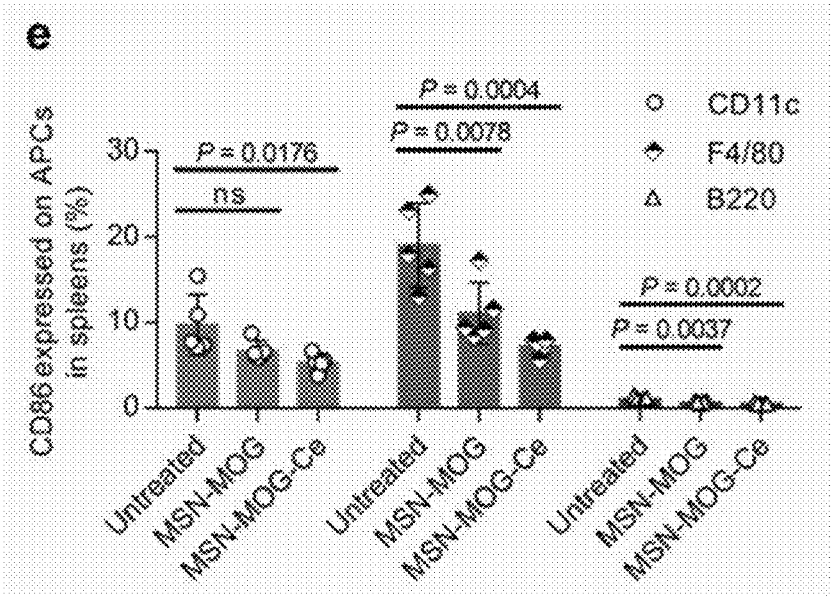
Figure 6F:
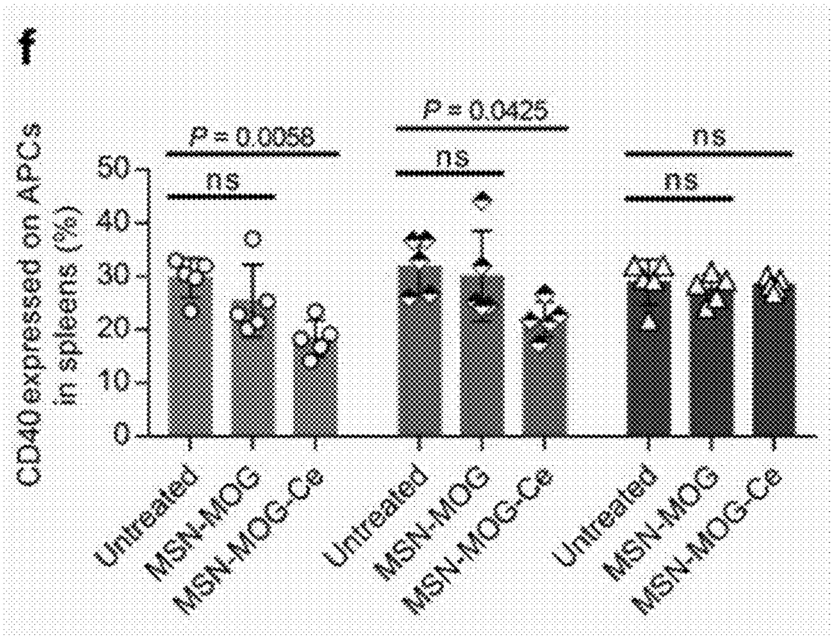
Figure 6G:
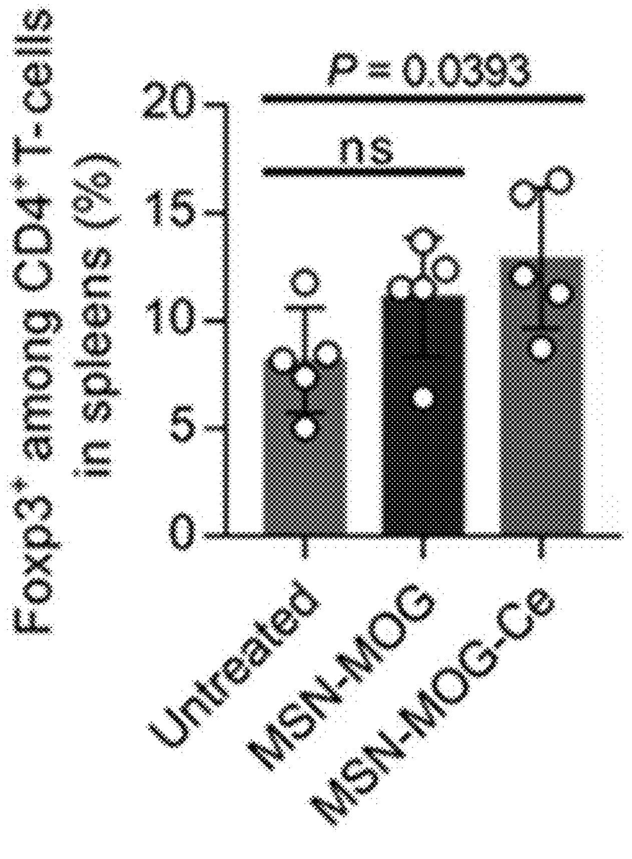
Figure 6H:
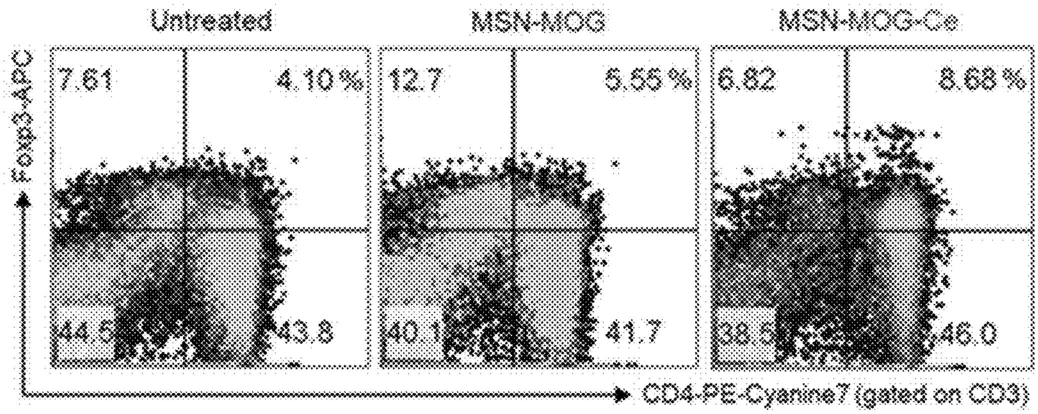
Figure 21A:
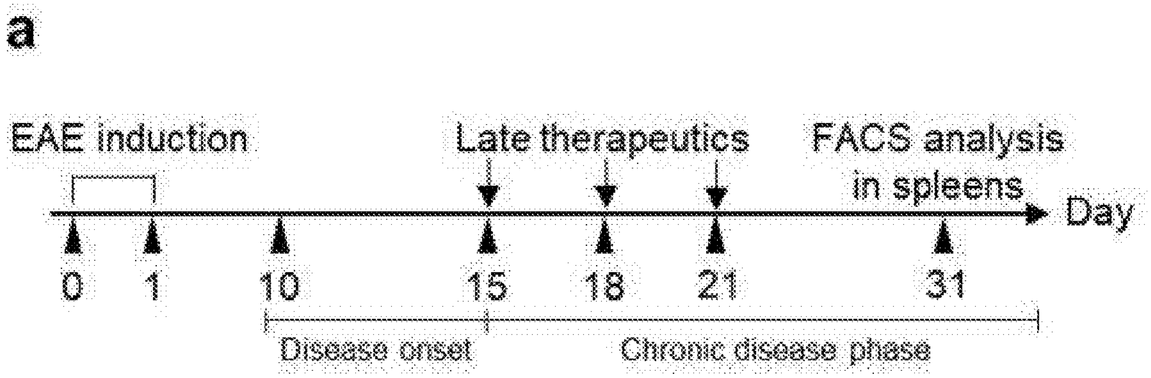
FIGS. 21*a*, 21*b* and 21*c* show the analysis of T-cells in the spleens after treatment with late therapeutics.
Figure 21B:
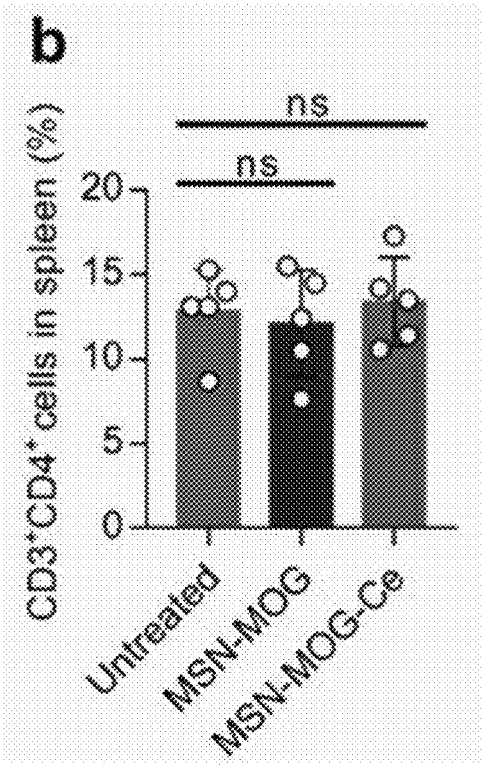
Figure 21C:
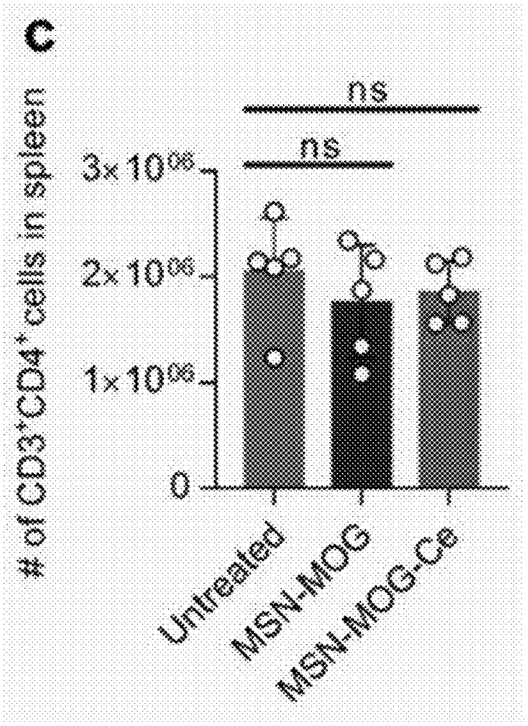

To further investigate the immunosuppressive role of ROS-scavenging CeNPs in the therapeutic autoimmune disease nanovaccine, the present inventors compared the cellular phenotypes and responses in mice with late EAE therapeutics after MSN-MOG and MSN-MOG-Ce administration. The frequency and number of splenic APCs of the treated mice showed no significant change compared to the untreated group, except for an increase in the frequency of $B220^+$ cells in the MSN-MOG-treated group (FIG. 19). CD86 expressions on $CD11c^+$ DCs, $F4/80^+$ macrophages, and $B220^+$ cells were significantly lower in the MSN-MOG-Ce-treated group than in the MSN-MOG-treated group (FIG. 6*e*). Similarly, CD40 expression on $CD11c^+$ DCs and $F4/80^+$ macrophages was significantly reduced in the MSN-MOG-Ce-treated group but not in the MSN-MOG-treated group (FIG. 6*f*). These results are consistent with the suppressive effects of CeNPs in vitro. There was no difference in MHC-II expression on APCs between groups (Supplementary FIG. 20), indicating that loading CeNPs on the nanovaccine only inhibited the expression of costimulatory molecules (CD86 and CD40) without affecting MHC-II, thus making the APCs more tolerogenic. Consequently, the MSN-MOG-Ce-treated group exhibited higher $Foxp3^+$ Tregs in the spleens of EAE-induced mice (FIG. 6*g* and FIG. 6*h*). The percentage of $Foxp3^+$ T cells among the $CD4^+$ T cells was twice as high in MSN-MOG-Ce-treated mice (day 31) compared to that in untreated mice. The frequency and number of $CD4^+$ T cells were similar among the three groups (FIG. 21). These results indicate that coating MSN-MOG with CeNPs did not elicit APC and helper T-cell proliferation in the spleen but drove the induction of $Foxp3^+$ Tregs via the immunosuppressive effects on APCs.

Figure 6I:
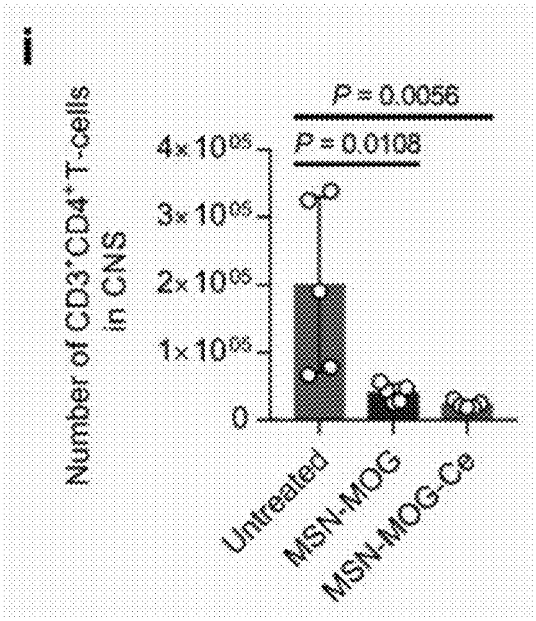
Figure 6J:
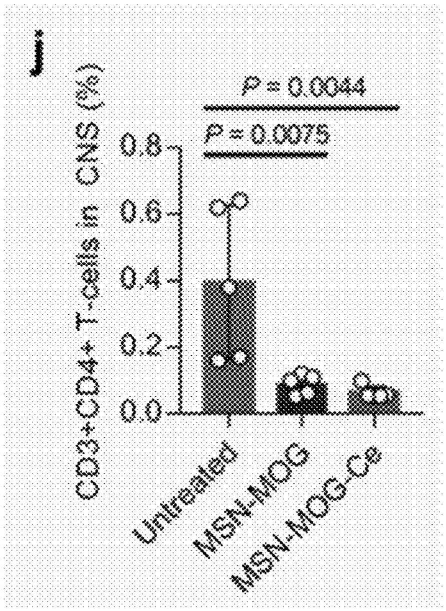
Figure 6K:
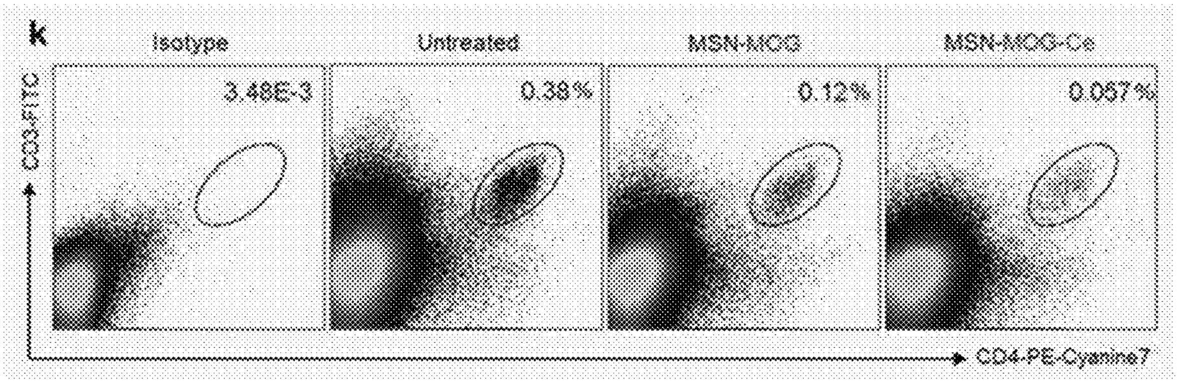
Figure 6L:
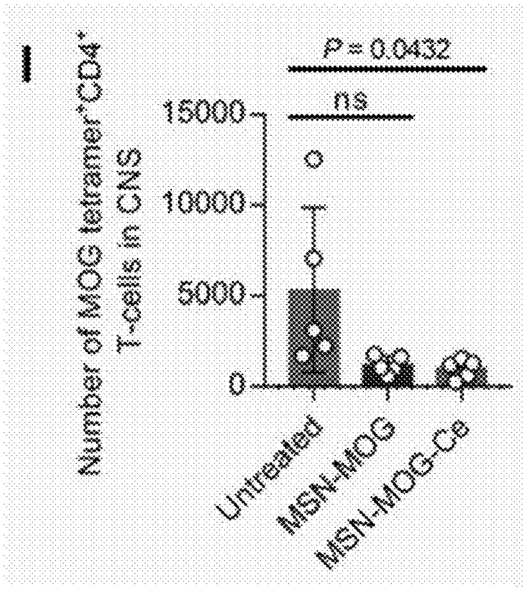
Figure 6M:
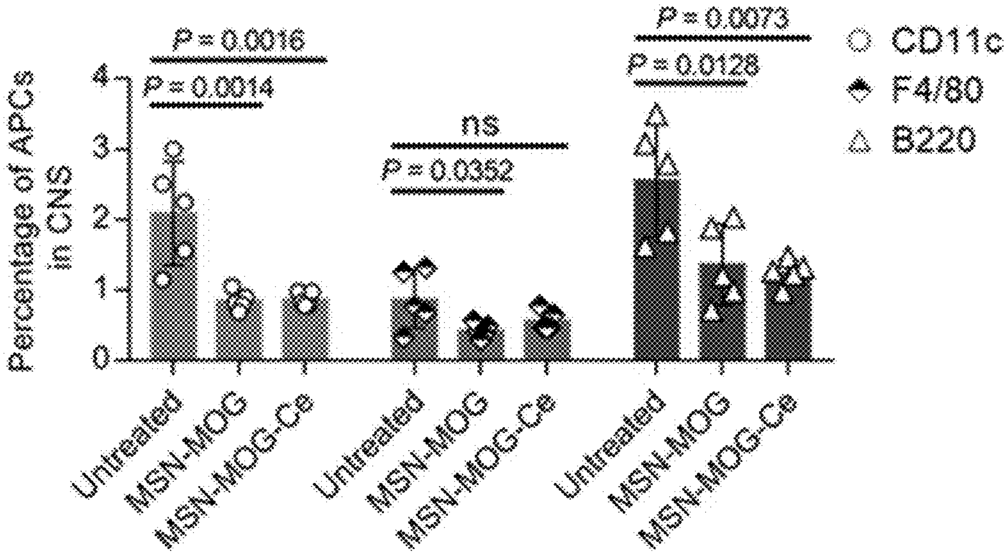
Figure 6N:
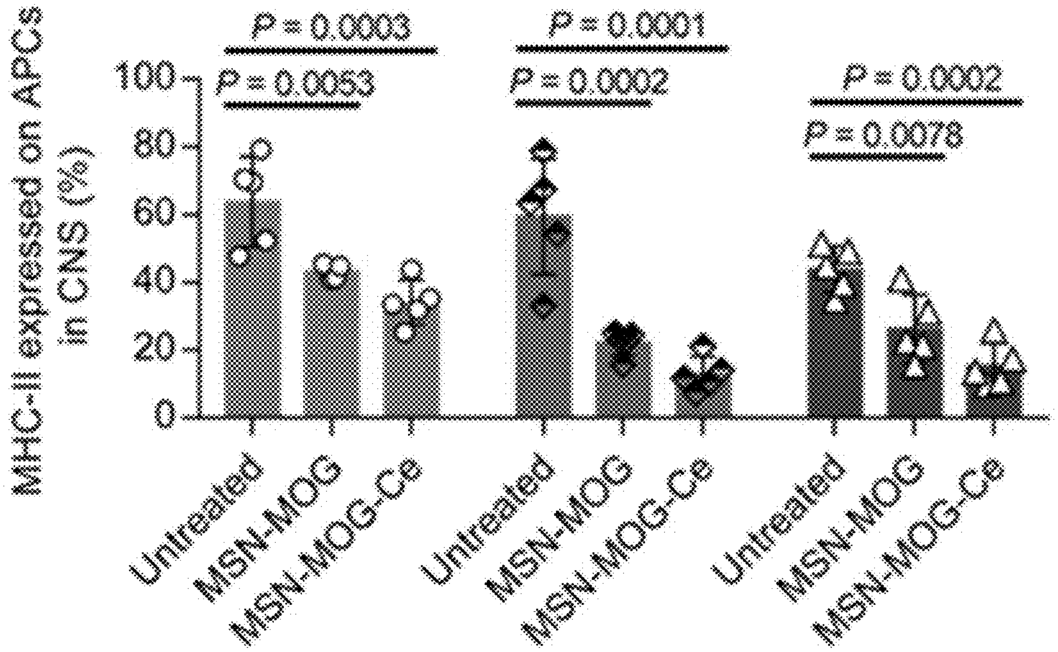
Figure 6O:
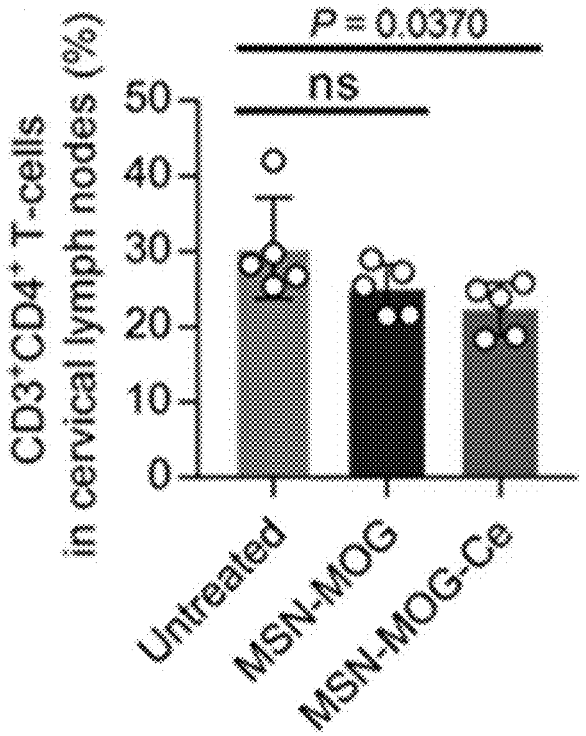
Figure 22:
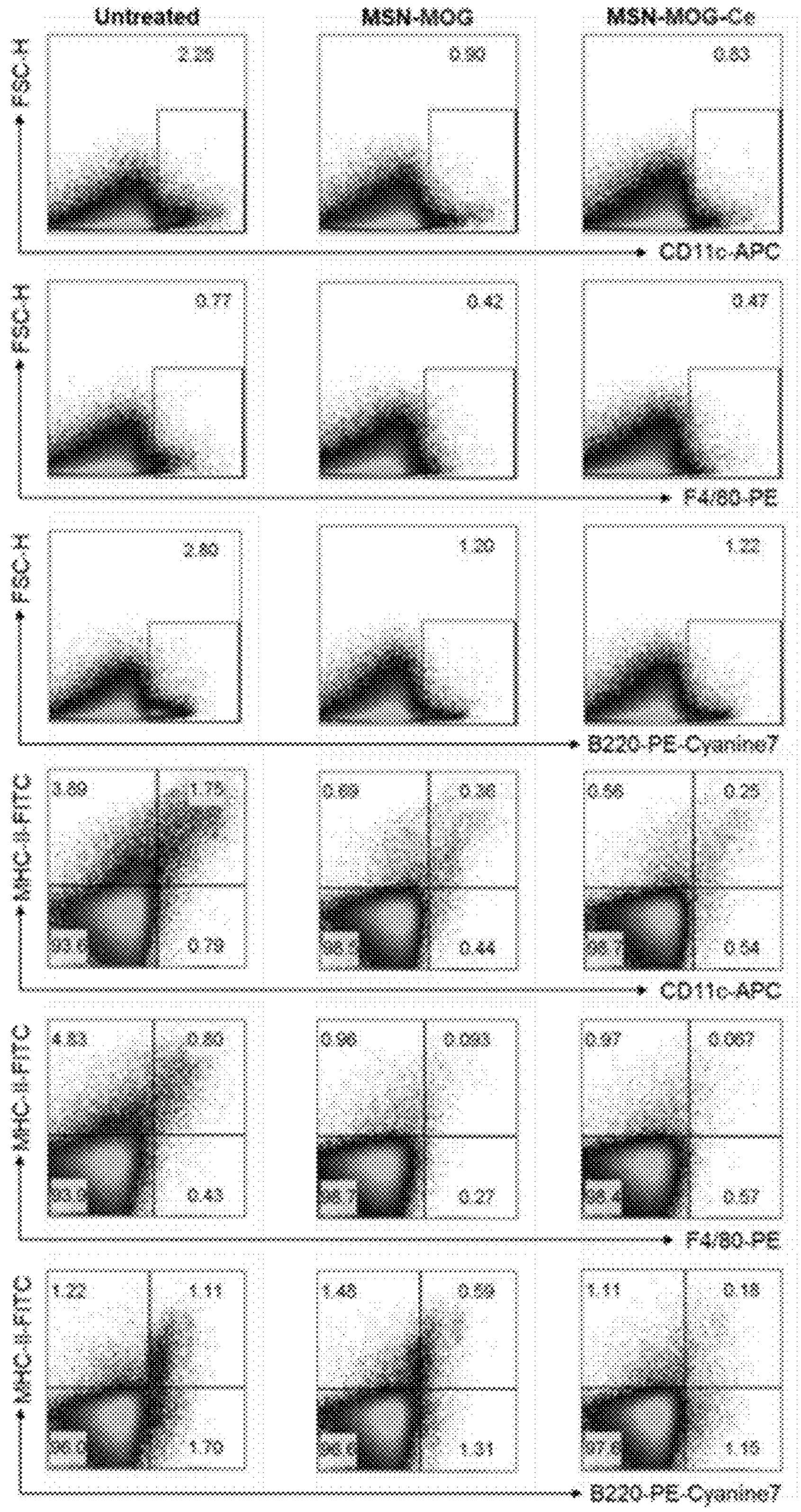
FIG. 22 shows MSN-MOG-Ce vaccine suppressing infiltration of APCs into CNS and their antigen presentation capacity in late therapeutics.
Figure 23:
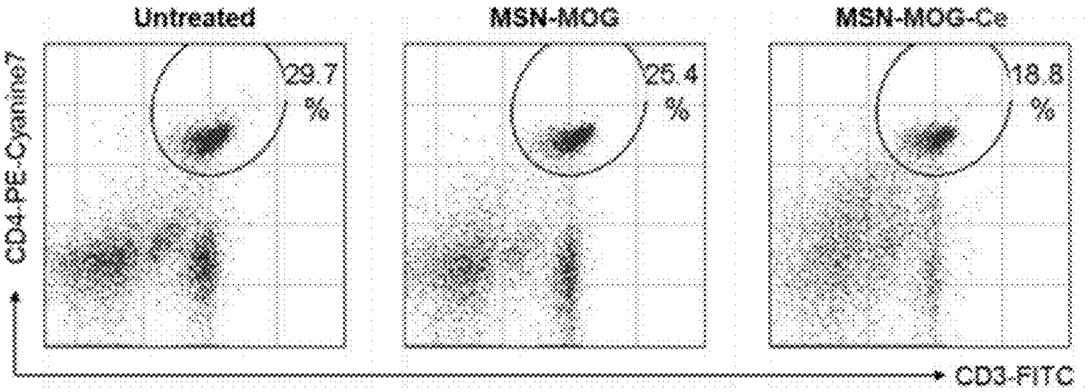
FIG. 23 shows MSN-MOG-Ce vaccine inhibiting $CD4^+$ T-cell in the CNS-draining lymph node in late therapeutics.

The infiltrated $CD4^+$ T cells in CNS is one of the indications to show severity of autoimmune response in EAE. The present inventors further examined the infiltration of autoreactive $CD4^+$ T cells into the CNS after vaccination. The numbers and percentages of $CD4^+$ T cells in the CNS in both MSN-MOG-treated mice and MSN-MOG-Ce-treated mice were significantly lower compared to the untreated group (FIG. 6*i*, FIG. 6*j*, FIG. 6*k*). Importantly, the number of MOG-specific $CD4^+$ T cells in CNS, which is the main cause of demyelination, was strongly reduced in MSNMOG-Ce-vaccinated mice (FIG. 6*l*). The enhanced peripheral tolerance induced by MSN-MOG-Ce resulted in the inhibition of CNS-infiltrating MOG-specific $CD4^+$ T cells and ameliorated disease severity in the late stage (FIG. 6*d*). Interestingly, the frequencies of $CD11c^+$ and $B220^+$ cells in the CNS were greatly suppressed by vaccination (FIG. 6*m* and FIG. 22). A diminishment in MHC-II expression on APCs was more significant in the MSN-MOG-Ce-treated group than in MSN-MOG counterpart (FIG. 6*n* and FIG. 22), probably owing to the inhibition of CNS-infiltrated autoreactive $CD4^+$ T cells. Consequently, the present inventors observed a reduction in $CD4^+$ T-cell frequencies in the cervical lymph nodes of the MSN-MOG-Ce-treated group at the late phase of MS (FIG. 6*o* and FIG. 23). Taken together, the introduction of ROS-scavenging nanovaccine did not affect the proliferation of splenic APCs but suppressed their costimulatory signals, which prevents activation of APCs and induces antigen-presenting tolerogenic APCs.

As a result, a higher frequency of peripheral Tregs could be generated in peripheral lymphoid organ and sequentially inhibit the infiltration of autoreactive $CD4^+$ T cells into CNS, which led to suppression of ongoing chronic phase MS (FIG. 1).

What is claimed is:

1. A vaccine composition for treating multiple sclerosis, the vaccine composition comprising: biocompatible porous nanoparticles; a myelin-derived self-antigen loaded in the nanoparticles, and ceria nanoparticles bound to the surface of the porous nanoparticles, wherein the myelin-derived self-antigen is myelin oligodendrocyte glycoprotein peptide, or a fragment thereof.

2. The vaccine composition of claim 1, wherein the biocompatible porous nanoparticles have mesopores with a diameter of 5 nm to 40 nm.

3. The vaccine composition of claim 1, wherein the biocompatible porous nanoparticles comprise three-dimensional radial pores.

4. The vaccine composition of claim 1, wherein the biocompatible porous nanoparticles are inorganic nanoparticles.

5. The vaccine composition of claim 4, wherein the inorganic nanoparticles are at least one selected from the group consisting of silica nanoparticles, iron oxide nanoparticles, cerium oxide nanoparticles, manganese oxide nanoparticles, platinum nanoparticles, selenium nanoparticles, and carbon nanoparticles.

6. The vaccine composition of claim 1, wherein the biocompatible porous nanoparticles are organic nanoparticles.

7. The vaccine composition of claim 1, wherein the fragment of the myelin oligodendrocyte glycoprotein peptide is 5 to 25 amino acids in length.

* * * * *